A

(12) United States Patent
Schueren et al.

(10) Patent No.: US 12,200,042 B2
(45) Date of Patent: Jan. 14, 2025

(54) COMMAND CENTER

(71) Applicant: IntegenX Inc., Pleasanton, CA (US)

(72) Inventors: Robert A. Schueren, Los Altos, CA (US); David King, Menlo Park, CA (US); Chungsoo Charles Park, Redwood City, CA (US); Arnaldo Barican, San Ramon, CA (US); Charles David Troup, Livermore, CA (US)

( * ) Notice: Subject to any disclaimer, the term of this patent is extended or adjusted under 35 U.S.C. 154(b) by 1092 days.

(21) Appl. No.: 17/039,647

(22) Filed: Sep. 30, 2020

(65) Prior Publication Data

US 2021/0021670 A1    Jan. 21, 2021

Related U.S. Application Data

(63) Continuation of application No. 15/910,743, filed on Mar. 2, 2018, now Pat. No. 10,855,748, which is a continuation-in-part of application No. PCT/US2016/054994, filed on Sep. 30, 2016.

(60) Provisional application No. 62/467,050, filed on Mar. 3, 2017, provisional application No. 62/264,314, filed on Dec. 7, 2015, provisional application No. 62/235,127, filed on Sep. 30, 2015.

(51) Int. Cl.
| | |
|---|---|
| *H04L 67/10* | (2022.01) |
| *G01N 27/447* | (2006.01) |
| *G06F 3/01* | (2006.01) |
| *G06F 3/04817* | (2022.01) |
| *G16B 20/20* | (2019.01) |
| *G16B 40/00* | (2019.01) |
| *G16B 40/10* | (2019.01) |
| *G16B 50/40* | (2019.01) |
| *H04L 67/306* | (2022.01) |
| *H04L 67/50* | (2022.01) |
| *H04L 67/52* | (2022.01) |

(52) U.S. Cl.
CPC ....... *H04L 67/10* (2013.01); *G01N 27/44704* (2013.01); *G06F 3/011* (2013.01); *G16B 20/20* (2019.02); *G16B 40/00* (2019.02); *G16B 40/10* (2019.02); *G16B 50/40* (2019.02); *H04L 67/306* (2013.01); *H04L 67/535* (2022.05); *G01N 27/447* (2013.01); *G06F 3/04817* (2013.01); *H04L 67/52* (2022.05)

(58) Field of Classification Search
None
See application file for complete search history.

(56) References Cited

U.S. PATENT DOCUMENTS

| | | | |
|---|---|---|---|
| 7,027,808 B2 * | 4/2006 | Wesby | H04W 8/245 455/423 |
| 10,210,410 B2 | 2/2019 | Schueren et al. | |
| 2002/0113707 A1 | 8/2002 | Grunes et al. | |
| 2003/0228604 A1 | 12/2003 | Plastow et al. | |
| 2004/0260733 A1 | 12/2004 | Adelstein et al. | |
| 2004/0265181 A1 | 12/2004 | Noda et al. | |
| 2006/0073820 A1 * | 4/2006 | Craswell | H04W 8/245 455/419 |
| 2008/0027756 A1 | 1/2008 | Gabriel et al. | |
| 2008/0307117 A1 | 12/2008 | Muller-Cohn et al. | |
| 2010/0138374 A1 | 6/2010 | Chakraborty et al. | |
| 2010/0265068 A1 | 10/2010 | Brackmann et al. | |
| 2010/0281401 A1 * | 11/2010 | Tebbs | G16B 20/10 707/769 |
| 2013/0231258 A1 | 9/2013 | Wilde et al. | |
| 2013/0232474 A1 | 9/2013 | Leclair et al. | |
| 2015/0088772 A1 | 3/2015 | Shwartz et al. | |
| 2015/0121522 A1 | 4/2015 | Guido | |
| 2015/0154350 A1 | 6/2015 | Pritzker et al. | |
| 2017/0018007 A1 | 1/2017 | Defrank et al. | |
| 2018/0060482 A1 | 3/2018 | Nadauld et al. | |
| 2018/0262557 A1 | 9/2018 | Schueren et al. | |
| 2018/0293680 A1 | 10/2018 | Schueren et al. | |

FOREIGN PATENT DOCUMENTS

| | | |
|---|---|---|
| CN | 101919261 A | 12/2010 |
| CN | 102955331 A | 3/2013 |
| WO | 2008/067169 A2 | 6/2008 |

OTHER PUBLICATIONS

Extended European Search Report dated Apr. 5, 2019, issued in EP Application No. 16852780.2.
International Preliminary Report on Patentability dated Apr. 3, 2018, issued in PCT Application No. PCT/US2016/54994, filed Sep. 30, 2016.
International Search Report and Written Opinion dated Jan. 19, 2017, issued in PCT Application No. PCT/US2016/54994, filed Sep. 30, 2016.
Summons to attend oral proceedings issued in Application No. 16 852 780.2, dated Apr. 6, 2023.
US Department of Justice: "The Future of Forensic DNA Testing", Nov. 30, 2000.

* cited by examiner

*Primary Examiner* — John S Brusca
*Assistant Examiner* — Steven W. Bailey
(74) *Attorney, Agent, or Firm* — JONES ROBB, PLLC

(57) ABSTRACT

A command center includes at least one network communications interface configured for two-way communications with a plurality of sites remote from the command center and at least one display screen and user interface. Each of the plurality of sites includes at least one forensic field test device configured to identify individuals using DNA samples from the individuals. The display screen and user interface are configured to depict aspects of forensic field test devices of the plurality of sites, wherein the aspects include a site identifier for each of the forensic field test devices and one or more additional aspects.

6 Claims, 34 Drawing Sheets

(200) (Step A) establishing a first communication link between a command center comprising a computer and at least one biochemical, biometric or diagnostic test device comprising a computer

(202) (Step B) performing a first two-way communication over the first communication link, wherein the first two-way communication includes:
    (210) communication between the command center and a user of the test device, wherein said communication communicates an instruction or query and a response to the instruction or query; and
    (212) communication between computers in the command center and in at least one of the test devices, wherein said communication communicates: (1) information from the test device about an operating parameter of the test device, and (2) instructions from the command center controlling the operating parameter of the test device

SpecialMatchingRuns

| Sample Name | Match | |
|---|---|---|
| 2016-10-14_(18.11)_AFB | ○ | |
| 2016-10-19_(16.16)_164M_GUI_1 | ⊗ | 164M |
| 2016-10-20_(13.36)_164M | ⊗ | 164M |
| 2016-10-10_(17.53)_215M | ⊗ | 215M |
| 2016-12-16_(17.25)_16CJ854 | ○ | SED0210 |
| 2016-12-17_(12.28)_16CJ850 | ○ | |
| 2016-12-23_(12.37)_16CJ804 | ○ | |

| Match | CommonLoci | MatchingAlleles | Mismatches |
|---|---|---|---|
| 215M | 17 | 30/30 | 0 |
| SED0464 | 17 | 28/30 | 2 |
| 278M | 17 | 25/29 | 4 |
| 135F | 17 | 27/31 | 4 |
| 185M | 17 | 28/32 | 4 |
| 127M | 17 | 25/29 | 4 |
| SED0268 | 17 | 27/32 | 5 |
| SED0328 | 17 | 25/30 | 5 |
| SED0424 | 17 | 24/29 | 5 |
| SED0148 | 17 | 24/28 | 4 |
| 33M | 17 | 26/31 | 5 |
| SED0257 | 17 | 25/30 | 5 |
| SED0370 | 17 | 24/29 | 5 |
| SED0359 | 17 | 27/32 | 5 |
| SED0140 | 17 | 26/30 | 5 |

FIG. 18B

| Locus | Sample Alleles X, Y | Reference Alleles X |
|---|---|---|
| AMEL | 14, 17, 16, 13, 169.4 | 16, 17 |
| VWA | 9, 9, 6, 8, 9, 5 | 6 |
| TH01 | 13, 16, 15, 12, 14 | 13, 16 |
| D8S1179 | 24, 23, 22, 295.7, 299.6 | 20, 24 |
| FGA | 39.2, 30, 922, 29, 29 | 29, 30 |
| D21S11 | 14, 16, 13, 12 | 14 |
| D16S51 | 17, 16, 15 | 17, 20 |
| D2S1338 | 13, 12, 14 | 9, 12 |
| D16S539 | 14, 13, 12, 12.2, 13.2 | 11, 14 |
| D19S433 | 16, 15, 15.2, 14, 17 | 16 |
| D3S1358 | 16, 15, 17, 14 | 15, 16 |
| D22S1045 | 16, 13, 15, 12, 169.4 | 14, 17.3 |
| D1S1656 | 16, 17, 15, 6, 14 | 14 |
| D10S1248 | 11, 14, 10, 13, 109.3 | 10, 14 |
| D2S441 | 17, 24, 23, 16, 22 | 16, 17 |
| D12S391 | | |

| Locus | Sample Alleles X,Y | Reference Alleles X,Y |
|---|---|---|
| AMEL | 14, 17, 16, 13, 169.4 | 16 |
| VWA | 9.3, 6, 9.3, 5 | 6, 9.3 |
| THO1 | 13, 16, 15, 12, 14 | 12, 15 |
| D8S1179 | 24, 23, 22, 29S7, 299.8 | 21, 22 |
| FGA | 33.2, 30, 32.2, 29, 26 | 30, 32.2 |
| D21S11 | 14, 16, 13, 12 | 13 |
| D18S51 | 17, 16, 16 | 17, 18 |
| D2S1338 | 13, 12, 14 | 12, 13 |
| D16S539 | 14, 13, 12, 12.2, 13.2 | 13, 14 |
| D19S433 | 16, 16, 15.2, 14, 17 | 14, 16 |
| D3S1358 | 16, 15, 17, 14 | 16 |
| D22S1045 | 16, 13, 19, 12, 169.4 | 15, 17.3 |
| D1S1656 | 16, 17, 15, 6, 14 | 13 |
| D10S1248 | 11, 14, 10, 13, 109.3 | 15 |
| D2S441 | 17, 24, 23, 16, 22 | 20, 22 |
| D12S391 | | |

Reference SED0148

COMMAND CENTER

REFERENCE TO RELATED APPLICATIONS

This application is a continuation of U.S. patent application Ser. No. 15/910,743, entitled "Command Center" and filed Mar. 2, 2018, now U.S. Pat. No. 10,855,748, which claims the benefit of and priority to U.S. Provisional Patent Application No. 62/467,050, entitled "Command Center" and filed Mar. 3, 2017, and U.S. patent application Ser. No. 15/910,743 is a continuation-in-part of and claims the benefit of International Application No. PCT/US2016/054994, entitled "Command Center" and filed Sep. 30, 2016, which claims the benefit of and priority to U.S. Provisional Patent Application No. 62/264,314, entitled "Command Center", filed Dec. 7, 2015, and to U.S. Provisional Patent Application No. 62/235,127, entitled "Command Center", filed Sep. 30, 2015, each of which is incorporated herein by reference in their entireties for all purposes.

STATEMENT AS TO FEDERALLY SPONSORED RESEARCH

None.

BACKGROUND OF THE INVENTION

In a number of jurisdictions including some in the United States, a person cannot be held in custody for an unreasonable amount of time without being charged with a crime. Identification of persons of interests by law enforcement agencies may employ forensic testing, such as DNA and biometric testing. Conventionally, such tests are performed by sending biological samples to a central location for processing and analysis, which may take weeks or months.

One effort to expedite identification of persons of interest by law enforcement agencies is to provide field equipment at various locations to collect and process DNA samples, and upload the resulting forensic data for searching of a forensic database. If a match is found between a person's profile and a profile from a forensic sample in the database, there may be reason to link the person with crime associated with the profile in the database.

However, there may be various technical problems associated with the field equipment and the results generated by the field equipment. For many of these problems, time is of essence at least because the limited duration of custody and availability of the person giving the sample. For instance, data analysis results may need expert review and input to determine whether a sample has been properly processed or a further sample needs to be collected. If it is not promptly determined that an analysis of a sample is problematic, a further sample may not be available after the person is released.

Moreover, equipment hardware, software, and supply of consumables needed for testing may have technical problems or need status monitoring. However, personnel available at the field often do not have the technical expertise to solve these problems promptly or at all. Even personnel at a central location do not always have prompt access to necessary information or knowledge expertise to solve these problems. In an example, for a large scale of network of field equipment, a large amount of DNA analysis files may require review and input from human experts, which may not be immediately available at the central location. Thus, files requiring review can cause substantial delays in completing the forensic analysis. Any delay between the time a file is generated by a system and the time that file is reviewed by a forensic scientist delays the time the file can be uploaded to a DNA database and a match determined. Such delay can result in release of a person in custody for whom a match may be found in the database.

A similar situation can arise with other types of forensic data tasks that require very quick performance or review by an expert. In some situations, two different DNA samples are processed (for example one from a crime scene and one from a person of interest) and the expert review needed is to determine if the profiles are a match. Again, time can be of the essence in particular situations and situations may arise at a time or place when experts are not generally available. Other forensic situations requiring expert review might include matching or analyzing crime scene data such as fingerprints, shoe prints, tire prints, various objects or materials, etc.

Automated genetic systems at present generally indicate one or more files that require review to an operator of the system and then wait for a human operator to take action to have the file reviewed by a qualified expert such as a forensic scientist or to otherwise have the file checked or rerun to meet quality standards. The reviewed or corrected file may then be uploaded to a DNA database to determine a match. Review and correction of a file by a forensic scientist can improve the accuracy of allele calls in an STR profile, thereby improving the probability that a correct match will be found. However, law enforcement personnel may lack the expertise to run and maintain the DNA test system, and when help is needed, there is no easy way to remotely support the forensic law enforcement users and maintain the forensic equipment in the field.

BRIEF SUMMARY OF THE INVENTION

One aspect of the disclosure relates to a command center including a computer. The command center includes (a) at least one network communications interface configured for two-way communications with a plurality of sites remote from the command center, wherein each site comprises at least one forensic field test device configured to identify individuals using DNA samples from the individuals; and (b) at least one display screen and user interface. The display screen and user interface are configured to: depict aspects of forensic field test devices of the plurality of sites, wherein the aspects include a site identifier for each of the forensic field test devices and one or more additional aspects selected from the group consisting of: a current status of at least one of the forensic field test devices, a log of operations of at least one of the forensic field test devices, a status of consumables of at least one of the forensic field test devices, and operator information of at least one of the forensic field test devices. The display screen and user interface are also configured to receive input from personnel present in the command center for controlling operation of at least one of the forensic field test devices.

Some implementations provide systems including the command center and the forensic field test devices at the plurality of sites. In some implementations, the forensic field test devices include an electrophoresis device.

In some implementations, the command center includes logic for sending operation commands through the network communications interface to one or more forensic field test devices to control operation of the one or more forensic field test devices.

In some implementations, the display screen and user interface of the command center are further configured to display on the display screen a geographical map showing the site identifiers for the plurality of sites including the forensic field test devices. In some implementations, the display screen and user interface are further configured to receive user input selecting one or more of the site identifiers displayed on the geographical map. In some implementations, the display screen and user interface are further configured to display a log of operations of a forensic field test device at a site associated with a selected site identifier. In some implementations, the log of operations includes a list of instrument runs of tests using DNA data provided by the forensic field test devices at the sites.

In some implementations, the display screen and user interface of the command center are further configured to display a flag associated with an instrument run shown in the list of instrument runs, wherein the flagged instrument run includes a potentially unreliable DNA analysis. In some implementations, the command center further includes logic for providing the potentially unreliable DNA analysis to an expert at a location remote from the command center.

In some implementations, the display screen and user interface of the command center are further configured to display a DNA analysis interface for DNA data analyses performed on DNA data provided by the forensic field test devices at the sites. In some implementations, the DNA analysis interface is configured to receive user input for confirming or clearing a DNA analysis as unreliable.

In some implementations, the display screen and user interface of the command center are further configured to display the consumables monitor showing statuses of consumables of the forensic field test devices.

In some implementations, the display screen and user interface are further configured to display authorization statuses of operators of the forensic field test devices.

In some implementations, the command center also includes logic configured to send DNA test profiles to a third-party database center and/or receiving results from the third-party database center regarding whether the DNA profiles match any profiles in any DNA database of the third-party database center.

In other aspect of the disclosure relates to the command center including a computer. The computer includes: (a) at least one network communications interface configured for two-way communications with a plurality of sites remote from the command center, wherein each site includes at least one field test device, wherein the at least one field test device includes a biochemical test device, biometric test device, or a diagnostic device; and (b) at least one display screen and user interface. The display and user interface are configured to: depict aspects of field test devices of the plurality of sites, wherein the aspects include a site identifier for each of the field test devices and one or more additional aspects selected from the group consisting of: a current status of at least one of the field test devices, a log of operations of at least one of the field test devices, an instrument run list of at least one of the field test devices, a level of consumables of at least one of the field test devices, and operator information of at least one of the field test devices. The display and user interface are also configured to receive input from personnel present in the command center for controlling operation of at least one of the field test devices.

A further aspect of the disclosure relates to methods implemented on a command center computer including at least one network communications interface, at least one display screen and user interface, and one or more processors. The methods include: (a) establishing, through the at least one network communications interface, two-way communications between the command center computer and a plurality of sites remote from the command center computer, wherein each site includes at least one forensic field test device configured to identify individuals using DNA samples from the individuals; (b) displaying, using the display screen and user interface, aspects of forensic field test devices of the plurality of sites, wherein at least one of the aspects includes a site identifier for each of the forensic field test devices and one or more additional aspects selected from the group consisting of: a current status of at least one of the forensic field test devices, a log of operations of at least one of the forensic field test devices, an instrument run list of at least one of the forensic field test devices, a level of consumables of at least one of the forensic field test devices, and operator information of at least one of the forensic field test devices; and (c) receiving, using the display screen and user interface, input from personnel present in the command center for controlling operation of at least one of the forensic field test devices.

In some implementations, the forensic field test devices include an electrophoresis device.

In some implementations, the method further includes sending operation commands through the network communications interface to one or more forensic field test devices to control operation of the one or more forensic field test devices. In some implementations, the method involves displaying a geographical map showing the site identifiers for the plurality of sites including the forensic field test devices. In some implementations, the method further including receiving user input that selects one or more of the site identifiers displayed on the geographical map. In some implementations, the method further involves displaying a log of operations of a forensic field test device at a site associated with a selected site identifier. In some implementations, the log of operations includes a list of instrument runs of tests using DNA data provided by the forensic field test devices at the sites. In some implementations, the method further involves displaying a flag associated with instrument run shown in the list of instrument runs, wherein the flagged instrument run includes a potentially unreliable DNA analysis. includes a potentially unreliable DNA analysis. In some implementations, the method includes sending the potentially unreliable DNA analysis to an expert at a location remote from the command center.

In some implementations, the method includes displaying a DNA analysis interface for DNA data analyses performed on DNA data provided by the forensic field test devices at the sites. In some implementations, the method including receiving, using the DNA analysis interface, user input for confirming or clearing a DNA analysis as unreliable.

In some implementations, the method includes displaying the consumables monitor showing statuses of consumables of the forensic field test devices.

In some implementations, the method includes displaying authorization statuses of operators of the forensic field test devices.

In some implementations, the method further involves sending, through the network communications interface, DNA test profiles to a third-party database center and/or receiving results from the third-party database center.

In one aspect disclosed herein is a computer-implemented method comprising: (a) establishing a first communication link between a command center comprising a computer and at least one biochemical, biometric or diagnostic test device comprising a computer; and (b) performing a first two-way communication over the first communication link, wherein the first two-way communication includes: (i) communication between the command center and a user of the test device, wherein said communication communicates an instruction or query and a response to the instruction or query; and (ii) communication between computers in the command center and in at least one of the test devices, wherein said communication communicates: (1) information from the test device about an operating parameter of the test device, and (2) instructions from the command center controlling the operating parameter of the test device.

In one embodiment, the method further comprises: (c) establishing a second communication link between the command center and an operations service provider; and (d) performing a second two-way communication over the second communication link, wherein the second two-way communication includes transmitting a query concerning command center or test device operation from the command center to the operations service provider, and receiving a response to the query at the command center from the operations service provider. In another embodiment the method comprises initiating a help request at the command center and processing the help request at the operations service provider. An operations service provider has specialized knowledge of test devices and of the command center.

In one embodiment, the method further comprises: (c) performing a biochemical, biometric or diagnostic test on the test device to produce a test result and communicating the test result to the command center over the first communication link; (d) establishing a second communication link between the command center and at least one third party database; and (e) performing a second two-way communication over the second communication link, wherein the second two-way communication includes transmitting the test result from the command center to the third party database, and receiving at the command center a communication from the third party database, wherein the communication indicates a result of a search of the third party database of information relating to the test result. In another embodiment the method further comprises: (f) performing a communication from the command center to the test device reporting the result of the search. In another embodiment the database is a forensic database. In another embodiment the database is an STR database.

In one embodiment, the method further comprises: (c) performing a biochemical, biometric or diagnostic test on the test device to produce a test result including a report and communicating the test result to the command center over the first communication link; (d) establishing a second communication link between the command center and at least one service provider; and (e) performing a second two-way communication over the second communication link, wherein the second two-way communication includes transmitting the test result from the command center to the at least one service provider, and receiving at the command center a communication from the at least one service provider including a revised report. In some implementations, the service provider is a forensic expert trained to analyze the test result. In one embodiment the at least one service provider is crowd-sourced. In some implementations, the at least one service provider comprises multiple service providers.

In one embodiment, the method further comprises: (c) establishing a second communication link between the command center and a consumables supplier; and (d) placing an order for consumables over the second communication link, e.g., for delivery to a location of a test device.

In another embodiment the at least one test device is a plurality of test devices.

In another embodiment communication is performed over a cloud-based computing service.

In another embodiment communication is performed over radio or telephone.

In another embodiment communication is performed over the internet.

In another embodiment the method comprises encrypting prior to transmitting messages.

In another embodiment the instruction is initiated by a computer of the command center or an operator at the command center, and wherein the instruction concerns operation of the test device.

In another embodiment the query is initiated by the user of a test device and is directed to a computer of the command center or an operator at the command center, and wherein the query concerns operation of the test device. In another embodiment the query is delivered by voice or text.

In another embodiment the method comprises remotely administering a proficiency test to a user of the first device. In another embodiment the method comprises altering the proficiency test by remotely changing one or more questions.

In another embodiment the first communication link further comprises video communication between a camera in the test device and the command center. In another embodiment the instruction is based on video communication originating at the test device, or the query is delivered through video communication at the test device.

In another embodiment the method comprises processing a help request initiated at the test device.

In another embodiment the method comprises processing a help request via text, email, voice conference, video conference, or telephone call.

In another embodiment the query concerns a subject selected from the group consisting of Monitor instrument status, Data transfer, Remote help, Ordering, User management, Consumables management, User Compliance, and System QC.

In another embodiment the operating parameter is selected from the group consisting of Monitor instrument status, Data transfer, Remote help, Ordering, User management, Consumables management, User Compliance, and System quality control (QC).

The method of claim 1, further comprising displaying on one or more monitors at a location of the command center, information about status of each test device in communication with the command center.

In another embodiment the device includes one or more instruments, comprising monitoring one or more of the instruments.

In another embodiment the method comprises remotely monitoring a utilization of the first test device.

In another embodiment the test device exposes a test cartridge to a solution in a chemical cartridge, and wherein the method comprises remotely monitoring remaining solutions in the chemical cartridge.

In another embodiment the chemical cartridge comprises an assay, comprising monitoring assay performance.

In another embodiment the method comprises generating an alert to reorder one or more chemical cartridges when cartridge usage reaches a predetermined threshold.

In another embodiment the method comprises remotely detecting if a chemical cartridge is expiring and generating an alert therefrom.

In another embodiment the method comprises remotely monitoring hardware and software performance of the test device.

In another embodiment the method comprises periodically (e.g., about every week, month, quarter or year) any of performing remote quality control or diagnostics on the test device.

In another embodiment the method comprises remotely checking for correct operator usage of the test device.

In another embodiment the method comprises remotely checking if the test device is powered on.

In another embodiment the method comprises sending a reminder to a user of the test device about an upcoming quality control test.

In another embodiment the method comprises detecting if a test device supply is below a predetermined threshold and generating an order to resupply the first test device.

In another embodiment the method comprises receiving the order and generating an estimated arrival date.

In another embodiment the method comprises generating an alert when a chemical supply or a number of available reactions at the first test device is below a threshold.

In another embodiment the method comprises remotely updating software on the test device.

In another embodiment the test device performs an analysis selected from a medical diagnostic test, detection of a blood borne analyte, DNA sequence analysis, STR analysis, fingerprint analysis, retinal scan, facial recognition and voice recognition.

In another embodiment the test device performs forensic analysis.

In another embodiment the method comprises establishing a network socket connection with a first test device.

In another aspect provided herein is a system comprising: (a) a command center comprising a computer; and (b) at least one biochemical, biometric or diagnostic test device in two-way communication with the command center; and wherein the command center and the test device are configured to exchange: (i) first two-way communication between a computer in the command center or an operator at the command center and a user of the test device; and (ii) a second two-way communication between a computer at the command center one or more test devices. In one embodiment the command center further comprises at least one monitor that displays information about status of each test device in communication with the command center. In another embodiment the system further comprises a communication link with a cloud-based computing service. In another embodiment the system further comprises a communication link with a cloud-based computing service. In another embodiment the system further comprises a communication link with a third party database. In another embodiment the system further comprises a communication link with at least one test result review expert. In another embodiment the system further comprises a communication link with an operations service provider.

In another aspect provided herein is a system comprising: a central computer comprising a display having one or more display screens displaying a plurality of icons, wherein the central computer is configured to establish two-way communication with a plurality of remote test devices through a communications network; a plurality of remote test devices configured for two way communication with the central computer through the communications network, and wherein clicking on a particular one of the icons enable communication through the communications network with a particular one of the test devices; and wherein other of the icons, when clicked, enable communication with one or more other remote computers in communication with the central computer through the communications network, wherein the remote computers are selected from: (1) a computer containing a forensic database; (2) a computer providing content related to forensic science or law enforcement; (3) a computer used by an expert forensic service provider; and (4) a computer used by a supplier of consumables used in operation of the remote test devices. In certain embodiments, clicking other particular icons enables communication between a plurality of the remote computers, e.g., at least three or all four of the remote computers enumerated.

BRIEF DESCRIPTION OF THE DRAWINGS

FIGS. 2A, 2B, 2C and 2D show exemplary processes executed by a system of this disclosure.

FIG. 15 shows a graphical user interface including information of orders of consumables.

FIGS. 18A-18E show graphical user interfaces or a computer tool for comparing electrophoresis data of test samples and staff members.

DETAILED DESCRIPTION OF THE INVENTION

I. Introduction

A system of this disclosure includes a command center configured as a communications hub between the command center and a number of termini. The termini can include one or more test devices, one or more third party databases, one or more expert reviewers of test device results and one or more operations service centers.

Provided herein is a system comprising a central computer comprising a network communications interface. The central computer communicates with each of a plurality of remote computers through a two-way communication network. In some embodiments, each remote computer is comprised in a forensic field test device. Such devices can be configured to identify individuals using DNA samples from the individuals. The central computer can comprise at least one display screen and user interface configured to: depict aspects of forensic field test devices of the plurality of sites, wherein the aspects comprise a site identifier for each of the forensic field test devices and one or more additional aspects selected from the group consisting of: a current status of at least one of the forensic field test devices, a log of operations of at least one of the forensic field test devices, a status of consumables of at least one of the forensic field test devices, and operator information of at least one of the forensic field test devices; and receive input from personnel present in the command center for controlling operation of at least one of the forensic field test devices.

In certain embodiments, remote computers in communication with the central computer can include computers containing databases of information, e.g., forensic or medical databases; computers containing interfaces for communication with experts, computers of service providers and/or, computers of advertisers or content providers, e.g., content concerning forensics.

The command center can perform a number of remote functions including: Monitoring instrument status, transferring data, providing remote help, ordering supplies, managing user activity, managing consumables, managing user compliance, and providing system quality control. The control center improves efficiency Data review, Quality control, Live help, Ordering, and Linkage of regional Command Centers (command center) to centralized command center.

Figure 1:
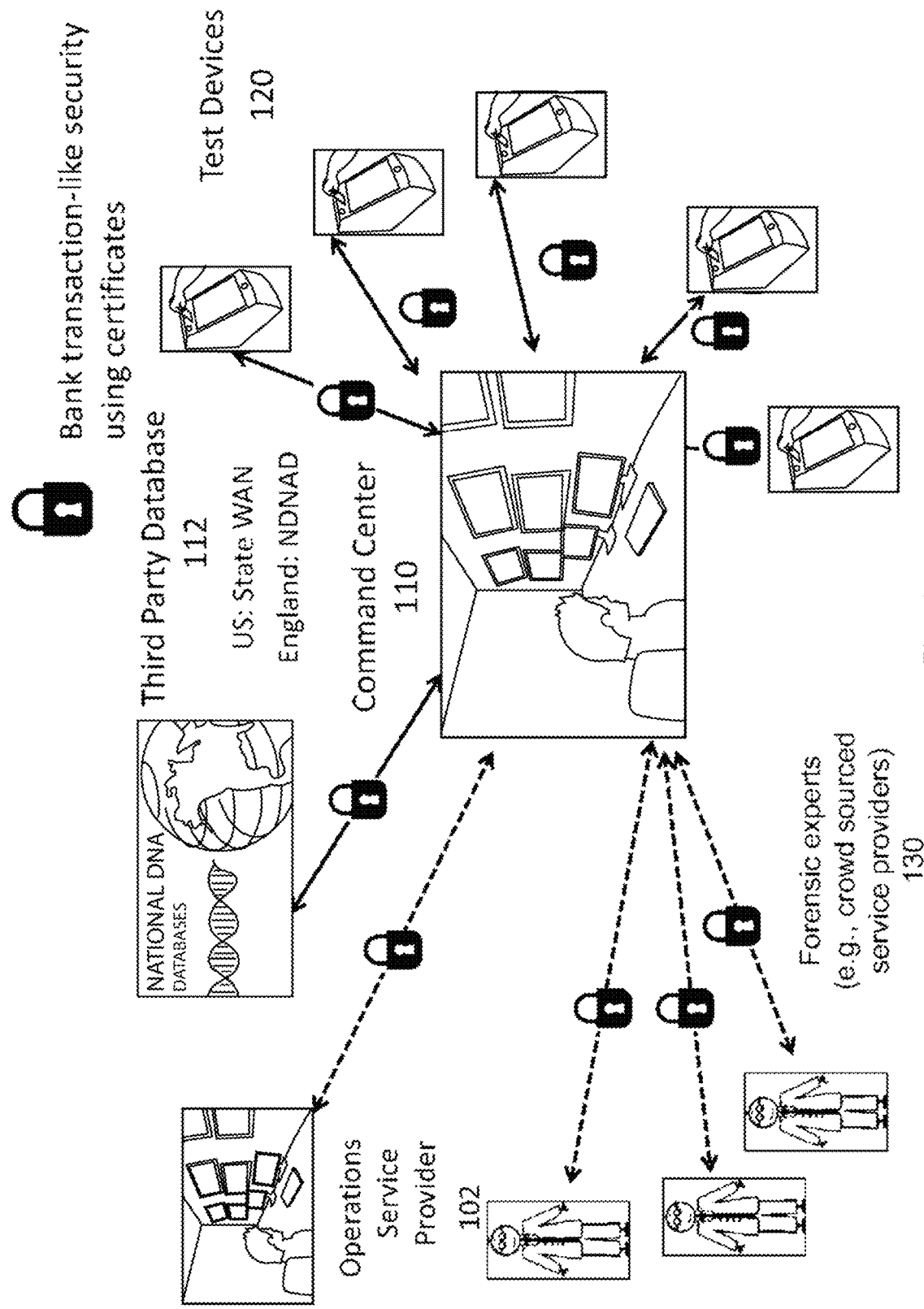
FIG. 1 shows an exemplary command center system of the disclosure.

Turning now to FIG. 1, an exemplary command center 110 provides remote support or assistance to a plurality of test devices 120, each of which can be biochemical, biometric or diagnostic test device, and which can be located in stations from which the command center is remote (e.g., "remote" test devices). A remote device can be located in another room, another building, another city, another state or another country. A remote device can be located at least 500 meters, at least 1 kilometer, at least 10 kilometers, at least 100 kilometers or at least 1000 kilometers from the command center. In one embodiment, the command center 110 can be operated by law enforcement agency such as a city, state or national police department. It can be located in department headquarters and can communicate with test devices in each of a plurality of local police stations. The command center 110 can be standalone. Command center 110 also can communicate with an operations service provider 102, which itself can function as a command center. The command center 110 can also communicate with computers used by one or more test result reviewers, e.g., forensic experts, 130 who can supply advice to any other member using the network of FIG. 1. The command center also can communicate with a third party database of test result information, 112.

II. Methods

FIGS. 2A-2D show exemplary processes executed by the command center of FIG. 1. In (200) the process includes establishing a first communication link between a command center and at least one biochemical, biometric or diagnostic test device. In (202), the process performs a first two-way communication over the first communication link with: (210) communication between the command center and a user of the test device, wherein said communication communicates an instruction or query and a response to the instruction or query; and (212) communication between computers in the command center and in at least one of the test devices, wherein said communication communicates: (1) information from the test device about an operating parameter of the test device, and (2) instructions from the command center controlling the operating parameter of the test device.

Two-way communication between the command center and a user of a test device can include a request for help by the user to either an operator at the command center or to a computer at the command center. Response can include instructions provided live by an operator or by the computer. Two-way communication also can include a query or a command from the command center to a user, such as an instruction, followed by a response from the user. The response from the user may be an automated signal from the device that an operation has been performed, e.g., that a swab has been scanned, subject identifying information has been inputted, a sample cartridge has been loaded or consumables have been loaded.

III. Communication with Test Devices

A. Devices

Systems and methods of this disclosure are useful for monitoring, from a central location, activities of instruments and users located remotely from the central location. The test device can be configured to perform, for example, a biochemical test, a forensic test or a diagnostic test. These tests are not mutually exclusive.

In one embodiment, the test device can be a forensic test device. The human genome is full of repeated DNA sequences. These repeated sequences come in various sizes and are classified according to the length of the core repeat units, the number of contiguous repeat units, and/or the overall length of the repeat region. DNA regions with short repeat units (usually 2-6 bp in length) are called Short Tandem Repeats (STR). STRs are found surrounding the chromosomal centromere (the structural center of the chromosomes). STRs have proven to have several benefits that make them especially suitable for human identification. STRs are popular DNA markers because they are easily amplified by polymerase chain reaction (PCR) without the problem of differential amplification; that is, the PCR products for STRs are generally similar in amount, making analysis easier. An individual inherits one copy of an STR from each parent, which may or may not have similar repeat sizes. The number of repeats in STR markers can be highly variable among individuals, which make these STRs effective for human identification purposes. For human identification purposes, the DNA markers need to exhibit the highest possible variation in order to discriminate between samples. It is often challenging to obtain PCR amplification products from forensic samples because either the DNA in those samples is degraded, or mixed, such as in a sexual assault case. The smaller size of STR alleles make STR markers better candidates for use in forensic applications, in which degraded DNA is common. PCR amplification of degraded DNA samples can be better accomplished with smaller target product sizes. Because of their smaller size, STR alleles can also be separated from other chromosomal locations more easily to ensure closely linked loci are not chosen. Closely linked loci do not follow the predictable pattern of random distribution in the population, making statistical analysis difficult. STR alleles also have lower mutation rates, which makes the data more stable and predictable. Because of these characteristics, STRs with higher power of discrimination are chosen for human identification in forensic cases on a regular basis. It is used to identify victim, perpetrator, missing persons, and others.

In one embodiment, using a rapid DNA testing instrument, such as the IntegenX RAPIDHIT® system, samples are collected from individuals, e.g., suspected of a crime, in custody suites, and processed by a forensic service as part of a program to run all samples from arrested suspects as part of their routine service offering. Rapid DNA profiles are completed in less than two hours from start to finish. A sample protocol includes cell lysis, DNA isolation, STR amplification through PCR and thermal cycling, product injection into a separation capillary, electrophoresis, detection of product and analysis of an electropherogram by computer.

The Rapid DNA system can fully automate and integrate all steps necessary to generate a DNA profile in less than two hours. DNA profiles generated can be completely compatible with standard databases that contain previously generated profiles from reference and crime scene sources, e.g., in a CODIS-compatible format. Combining ease of use and rapid turnaround time for DNA human identification will have a significant impact toward ensuring the safety of user communities.

In another embodiment, the device can perform a diagnostic test, such as X-ray, MRI, CAT scan, PET scan, etc. The command center can be a central medical facility such as a regional hospital.

B. Communication

One or more computers in the command center engage in two-way communication with a test device, exchanging information about an operating parameter of the device. The communication can include a query from the command center about the parameter and a response from the device indicating status of the parameter. Alternatively, the command center can receive a communication from a device about the status of an operating parameter and the command center can transmit an instruction to the device to alter the parameter. Two way communication can include, for example, communication about system status (e.g., on or off, operation error, assay in progress), assay performance (test parameters such as temperature, pressure, elevation, humidity, incubation timing, voltage), test results or status of on-board consumables.

The command center can request information about the parameter, receive a response from the device, and instruct the device to alter the parameter. For example, the parameter could involve status of a biochemical assay could include temperature, elevation, humidity, timing of thermal cycling, voltage of electrophoresis, etc. Altering the parameter could involve, for example, sending an instruction to raise or lower temperature, lengthen or decrease time of a thermal cycle, increase or decrease voltage used in electrophoresis.

Another operating parameter is status of consumables. For example, the command center can query a device about the amount of one or more consumables reagent in the device, receive a reply, and transmit an instruction to a supplier to provide supplies to the test device.

1. Monitoring Instrument Status

The command center 110 can remotely control/capture events generated at the test equipment 120. Such events can relate to data on monitor instrument status, data transfer, remote help, ordering, user management, consumables management, user compliance, and system QC. This remote ability is provided by running a daemon or a local client plug in at the test station 120 that collects user input and machine parameters in real time and communicate the data to the command center 110.

Monitoring instrument status can involve receiving communication from a test instrument regarding any of a number of operating parameters. These parameters can include (1) whether a system is on or off, (2) how often is unit being used, who is operating a device, (3) at what point a device is in carrying out a protocol.

The system can monitor any instrument on the forensic network.

2. Data Transfer and Data Review

Test results, such as forensic profiles or medical test results (e.g., X-rays, MRI, CAT scan), can be generated by test devices and reviewed at a command center. Non-flagged profiles either "pass through" automatically to database, or require review. The system provides notification schemes for requesting review (text, flashing indicator at command center). The system can flag profiles that require review with notification schemes for requesting review (text, flashing indicator at command center). The user can decide to perform "real time" review of flagged result (instrument simulates "still running" for defined time period). The system enables multiple potential reviewers of need to review, including transmission of profile to accepted reviewer, then transmission of reviewed result through command center to the remote test device, e.g., RAPIDHIT® ID (RH ID). A real time search of law enforcement (e.g. national/international) database can be done and the result can be sent back to the test station 120, for example.

3. Providing Remote Help

Remote help can be provided live from the command center. The remote user can request help from command center via text or email or any other methods. A number of notification schemes are supported by the command center for help request (text to phone, flashing indicator at command center). The response to help can come from the command center or from phone. For video support, the remote station 120 can include a camera to support real-time video communication between the equipment operator and the command center operator.

Remote help is a Web or network service that allows a supplier command center to communicate, or chat, in real time with customers from their test equipment. Live Help applications are commonly used to provide immediate customer support and information to clients and customers. Exact features and functions of live help are application specific. In one embodiment, a live chat, audio conferencing, or video conferencing application can provide real-time user monitoring, custom chat windows, background supply/consumable analysis, QC test integration and secure administration controls of the test instrument from the command center to one or more test devices, typically but not always remote from the command center. The system can be a programmable API, or can be a physical or virtual button that is activated by the test equipment user to request help in one embodiment.

4. Managing Consumables and Ordering Supplies

Command center may receive orders from the remote test equipment. The supply management process can be active, where the remote user transmits a request from a shopping cart to the command center and the command center acknowledges, e.g., with a receipt of order and expected arrival date. The supply management process can also be proactive in that the command center automatically notifies the remote user when number of forensic reactions remaining falls to a certain number and the command center in response either requests an order or automatically ships replacement. The supply management process can also be passive. In this case, when the remote station supply falls to a defined number of remaining tests, kit ships, the remote station operator is notified. Using the same process, the command center may send software upgrades to the remote machine, and the software update can be mandatory or can be opt in with user consent.

5. Quality Control

The command center can monitor test devices for quality control. This includes, for example: determining how often is unit being used, determining how many reactions are left in a reagent reservoir (e.g., a cartridge) associated with a test device and alerting an instrument user to re-order supplies, determining reagent expiration date and alerting a user when expiration is near, determining assay performance and determining hardware and software performance.

The system can also perform quality control frequency and can check if the operator is performing it as required. Reminders sent to the operator about upcoming QC run. The system can also monitor instrument performance and can alert the command center if power on the remote equipment is off. The system can also test the user by providing a proficiency quiz (e.g., after training video). The command center operator can decide on questions and communicate the tests to the remote equipment or instrument as part of the training of the remote equipment operator.

IV. Communication with Experts

Another determination that the automated system according to specific embodiments may make is to request expert review of the file by communicating with one or more service providers. Various criteria configured at the system will aid in determining whether it is desirable to request an external review and how to request the external review can include criteria such as: (1) identities and contact information of one or more service providers stored at the system; (2) performance statistics or scores of one or more service providers stored at the system; (3) other criteria, such as cost of one or more service providers stored at the system.

Figure 2B:
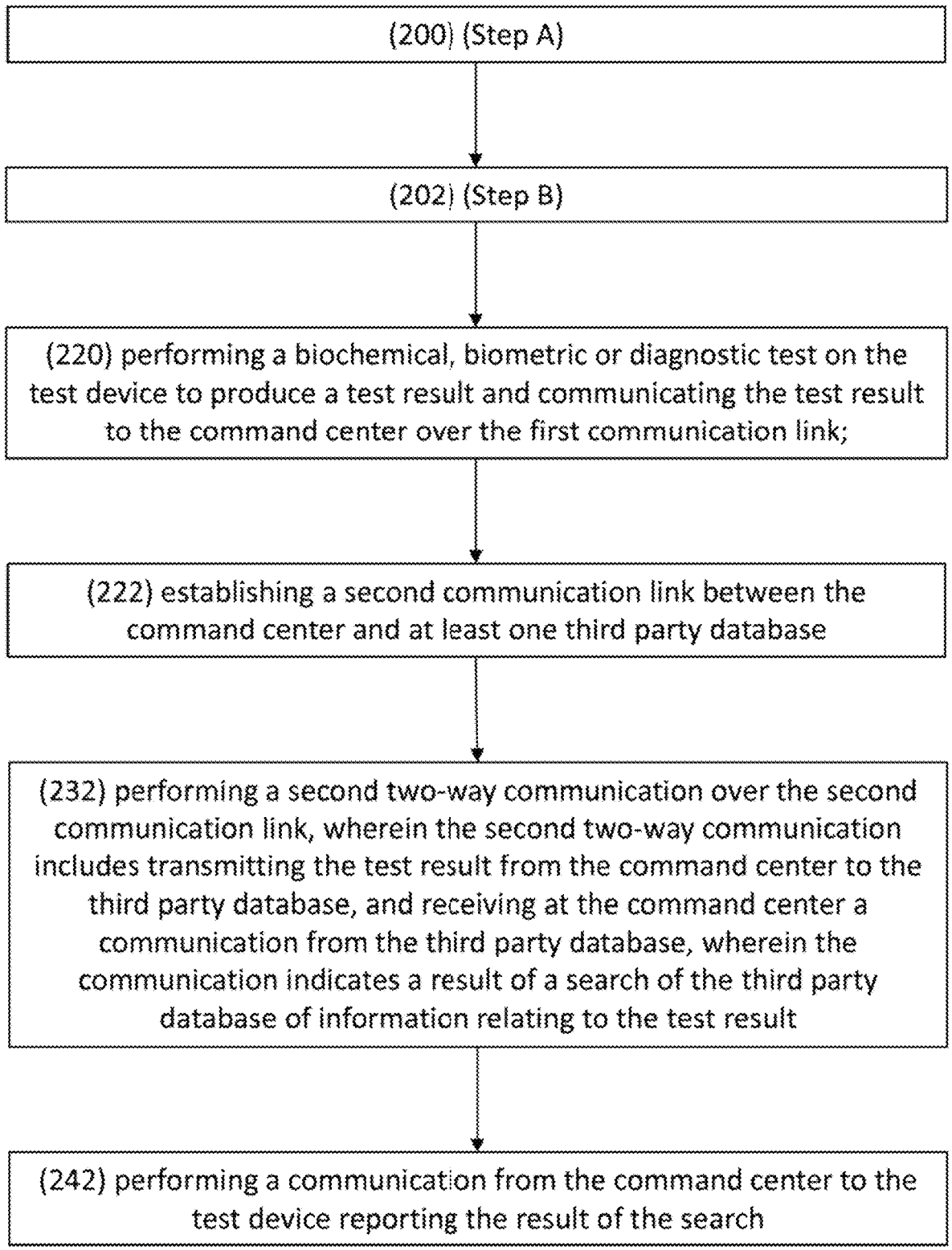
Figure 2C:
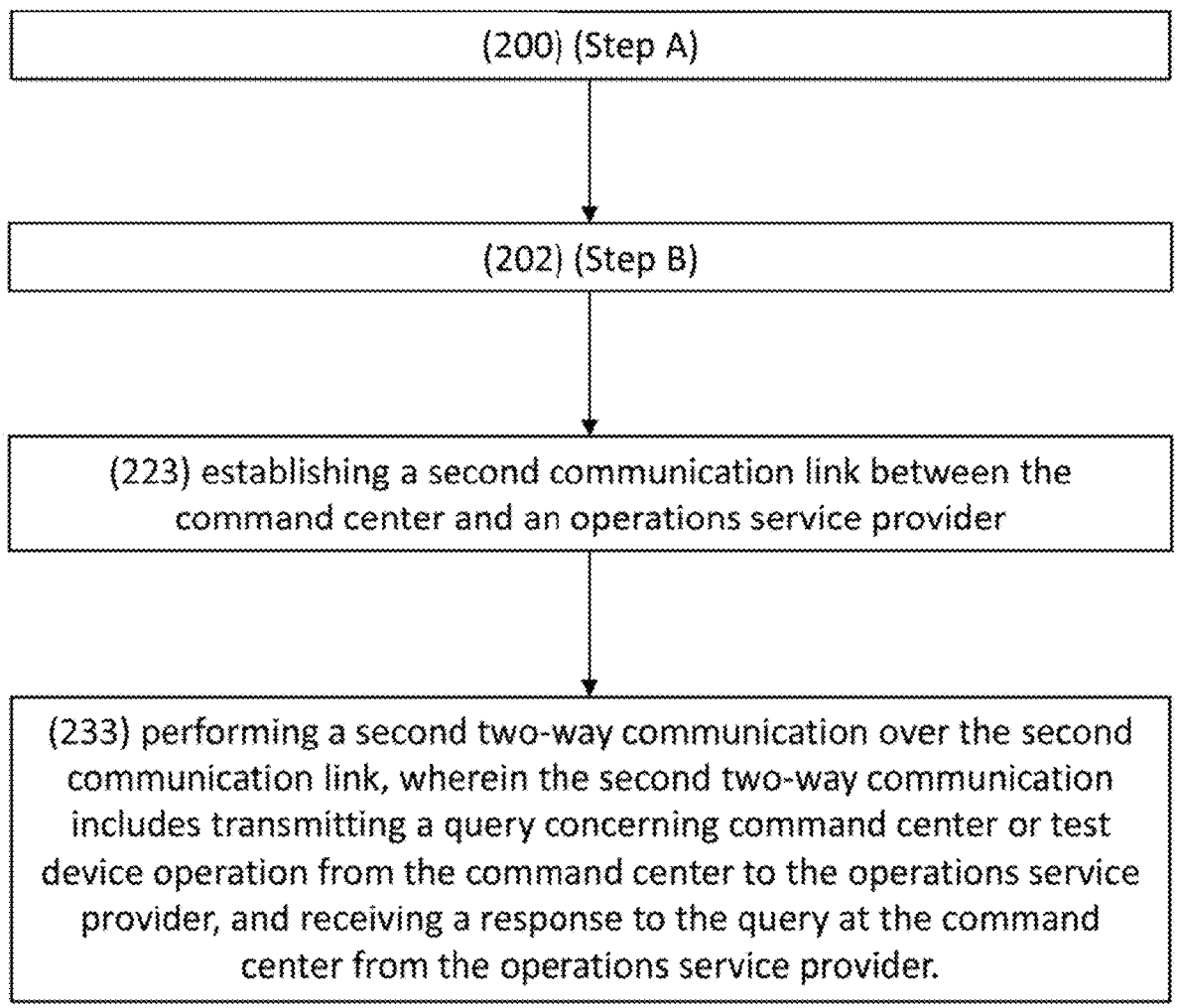
Figure 2D:
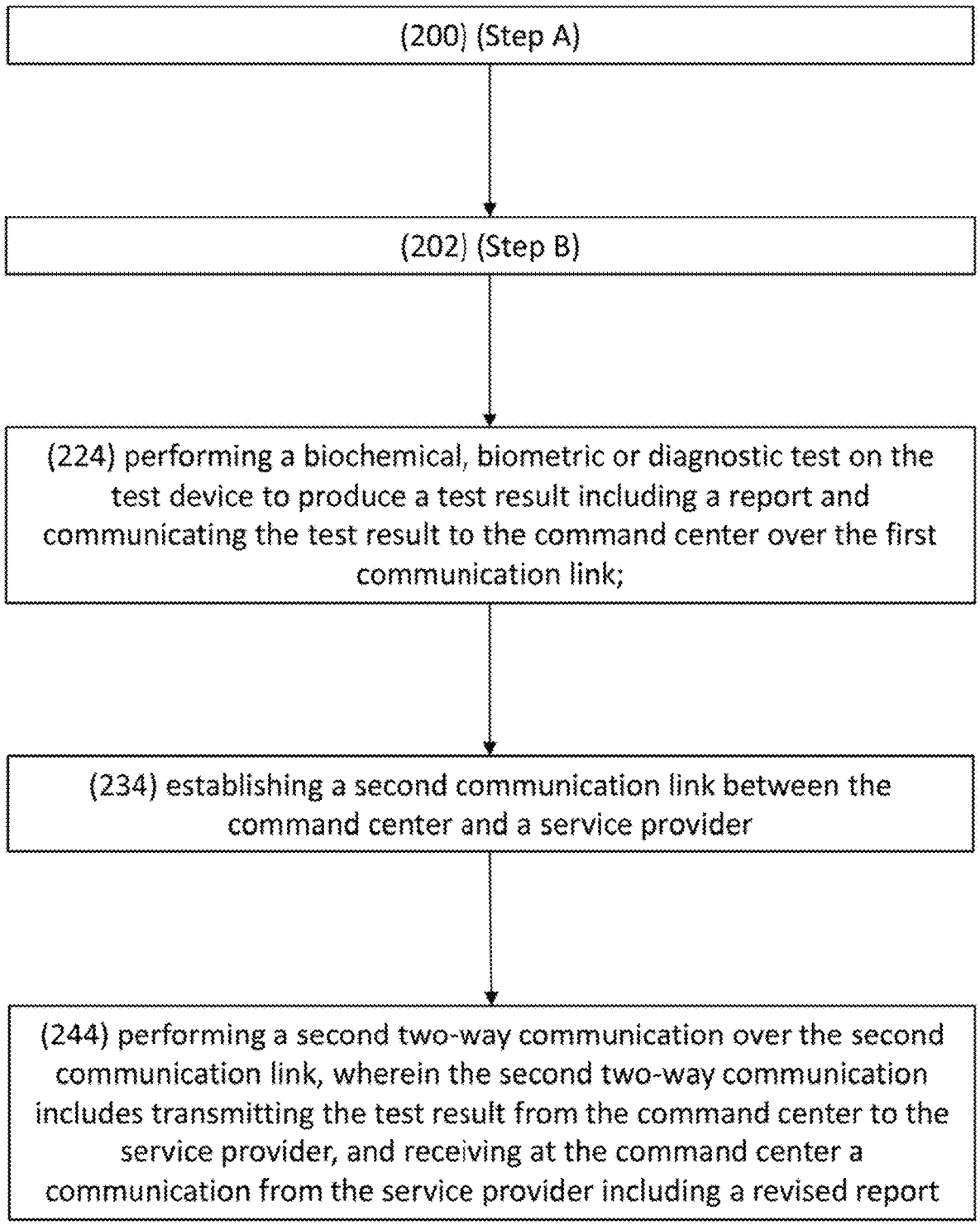

For example, referring to FIG. 2D, a biochemical test is performed and a result of the test is transmitted to the command center 224. Once the decision is made to request expert review of the file, the automated system communicates to one or more experts to have the file reviewed 234. As discussed elsewhere herein, in specific embodiments, this communication can be multi-step and send out multiple requests that service provides respond to for review of the file, where the response can include cost and respond time proposals. The automated system can receive the responses and select a reviewer.

After expert review is completed, a reviewed test result that may include revisions is transmitted back to the command center 244. If the resulting file meets criteria, it is uploaded. As discussed further below, a file may be confirmed by an outside expert or the file or part of the file may be corrected by the expert.

An automated system may have two STR profile files that require matching, that is, a determination that the profiles are consistent with having been generated from genetic material from the same person. In some jurisdictions, profiles constitute a match when at least 8 STR alleles are the same. This process is referred to herein as "profile matching". In one embodiment of the disclosure, the automated system communicates with one or more experts for profile matching of the data files. Profiles delivered to the service provider can include electropherograms that do or do not include flags, and can include files in which none, one or both files has previously been reviewed by an expert reviewer. Accordingly, in addition to determining whether the profiles constitute a match, the expert reviewer also can review the files to analyze or re-analyze flagged items, and produce a reviewed or revised file. The service provider delivers to the user a report determining a match or mismatch between the files and, optionally, reviewed and/or revised profiles.

In one example, once a system has generated an STR profile file, one or more further actions are taken with the file. As described herein, these further actions can be entirely automated, using one or more software components to decide on an action, or alternatively, one or more actions can include options for human intervention or human confirmation. In either case, further actions may be based on whether the file contains no flags or has one or more flags. If the file has no flags, the system can upload the file to DNA database for searching. If the file contains one or more flags, the system can decide between two options. One option, involves requesting the analysis to be performed again. This can involve, for example, the system taking another sample from a subject and analyzing it with the system, or sending a sample to another facility for analysis. Another option, involves delivering the file to a service provider for review. After the service provider has completed review and revision to the STR file, the revised file may be uploaded to a DNA database for matching. This upload may be done by the service provider or the revised file may first be delivered to the automated system, and the automated system may then upload the file to a DNA database for matching.

A protocol for having an STR profile file or other forensic data file reviewed can include the following steps: The system delivers computer file bearing flagged item to service provider. A service provider in receipt of a computer file containing flags performs a review. Objects of the review include clearing flagged items and/or confirming the file meets a quality control standard. According to specific embodiments, reviewing a computer file containing a flagged peak, the service provider may do any of the following: (i) Confirm the call of the flagged peak made by the software; (ii) Change or assign a call to a flagged peek, (iii) Delete a call made by the software or (iv) Do nothing. Service provider delivers reviewed file to automated system and the automated system uploads reviewed file to a criminal justice DNA database.

A review of a forensic file may be handled by an integrated automated system that performs some or all of the functions of communicating with various service providers, receiving bids or job acceptance requests, and assigns jobs to service provides and receives results. Alternatively or additionally, a review request may be communicated to a crowd-source server as described below that handles some or all communications with service providers.

In either alternative, service providers typically will contract with the system operator to provide the service "on-demand" for certain compensation. Other arrangements to form a contract to perform services may be used, such as one-sided contracting, in which the job is broadcast for performance by anyone. Individuals who contract with the service operator are referred to herein as "service providers". Service providers can be pre-qualified to perform the file review. For example, a service provider may be required to have the requisite skills to perform a review of a forensic file or to have passed a licensing examination. Such a person may already possess such skills, or may be trained, e.g., by the person or entity, to gain such skills.

Service providers can be assigned a quality rank based on desired factors such as accuracy of review, speed of review or physical location. In certain jurisdictions, an STR profile computer file, if it is to be reviewed, must be reviewed by a person physically located in a certain jurisdiction, such as a U.S. state. In operation, the method can involve some or all of the following steps: receiving notification from a user of a job to be performed, e.g., review of an STR profile computer file; notifying service providers of a job to be performed; receiving an indication from one or more service providers of their willingness to perform the job; selecting a service provider who has indicated their willingness to perform the review; providing access to the computer file to the selected service provider; having the service provider review the file; and receiving from the service provider a reviewed file. The user can provide the computer file before or after a service provider has been selected to perform the job. The user also can specify qualities desired or necessary in the service provider, such as level of training, physical location, turn-around time, error rate, etc. The request can be made directly from an expert system that generates the profile and that accesses the communications network directly, or by a person who submits the job.

Any suitable communications network can be used, such as cell or Internet. The notification may be in the form of a phone call, a text message, a mobile device notification, etc. Notification can come through an application designed for a mobile device or a computer. The notification can include a "response time," a time within which a person selected to perform a job must complete the job. Such a time may be no more than any of 10 hours, 2 hours, 1 hour, 30 minutes, 10 minutes or 5 minutes.

V. Communication with Third Party Databases

The system can communicate with third party databases, e.g., governmental/law enforcement databases or medical records databases, 112.

Beginning in 1996, the FBI Laboratory launched a nation-wide forensic science effort to establish core STR loci for inclusion within the national database known as CODIS (Combined DNA Index System). The 13 CODIS loci are CSFIPO, FGA, TH01, TPOX, VWA, D3S1358, D5S818, D7S820, D8S1179, D13S317, D16S539, D18S51 and D21S11. These loci are nationally and internationally recognized as the standard for human identification. While the FBI database is detailed, the system works with other national law enforcement agencies as well. Similar to the FBI, the United Kingdom National DNA Database (NDNAD; officially the UK National Criminal Intelligence DNA Database) is a national DNA Database that was set up in 1995. As of the end of 2005, it carried the profiles of around 3.1 million people. In March 2012 the database contained an estimated 5,950,612 individuals. The database, which grows by 30,000 samples each month, is populated by samples recovered from crime scenes and taken from police suspects and, in England and Wales, anyone arrested and detained at a police station. Only patterns of short tandem repeats are stored in the NDNAD—not a person's full genomic sequence. Currently the ten loci of the SGM+ system are analyzed, resulting in a string of 20 numbers, being two allele repeats from each of the ten loci. Amelogenin is used for a rapid test of a donor's sex. However, individuals' skin or blood samples are also kept permanently linked to the database and can contain complete genetic information. Because DNA is inherited, the database can also be used to indirectly identify many others in the population related to a database subject. Stored samples can also degrade and become useless, particularly those taken with dry brushes and swabs.

Referring to FIG. 2B, a biochemical test is performed and the result is transmitted to the command center 220. The command center can establish a communication link with a third party database 222 and send a computer file to a third party database for review. For example, a CODIS-compatible STR profile can be communicated to a forensic database. The database can compare the profile to profiles in the database. The third party database can communicate the presence or lack of a match between the transmitted profile and profiles in the database 232. This result can, in turn, be transmitted to a user at the test device 242.

VI. Communication with Operations Service Providers

Referring to FIG. 2C, a command center can establish communication link with an operations service provider 223. An operations service provider has specialized knowledge of test devices and of the command center. The command center and the operations service provider can engage in two-way communication 233. An operation service provider can be contacted to provide assistance with test device or command center operations, or to repair command center or test devices. Return communication can include acknowledgement of receipt of a request. The command center can communicate an order for service from the operations service provider in response to an indication of need for service from a test device.

In another embodiment, two way communication can include a query from the operations service provider about command center or test device needs, with a response from the command center regarding status or details of such needs. Operations service provider also can be a source for orders of consumables of test devices and software upgrades, among other things.

VII. Communication with Centralized Command Center

In another embodiment, a command center functions as a regional command center. One or more regional command centers can be in two-way communication with a centralized command center that receives some or all communications received by or transmitted from the regional command centers.

For example, an operations service provider can perform the functions of the command center, except through the command center communications links.

VIII. Communication Methods

Communication can occur over a communications network, which can include, for example, a high-speed transmission network including, without limitation, Digital Subscriber Line (DSL), Cable Modem, Fiber, Wireless, Satellite and, Broadband over Powerlines (BPL). Remote test devices can be configured for short link communication, e.g., Bluetooth, and can connect to a receiver such as a cellular telephone which connects through a cell to a cellular telephone communications network or a computer which connects to a communications network by Wi-Fi or by a direct wire connection. Alternatively, test devices can connect by Wi-Fi to a local area network which is connected to the communications network. In another embodiment, test devices connect directly to a cellular telephone network through a cell connection. Communications network can transmit received signal to a remote server in communication with the command center.

Preferably, communications within the network is done securely with the center 110 using encrypted communication links. Strong cryptography or cryptographically strong techniques are used to communicate data that are highly resistant to cryptanalysis. The system runs an encryption method that uses a very large number as its cryptographic key. The larger the key, the longer it takes to unlawfully break the code. In one embodiment, 256 bits is considered strong encryption, but 1024 bits, 2 k, or even 4 k key can be used.

Figure 6:
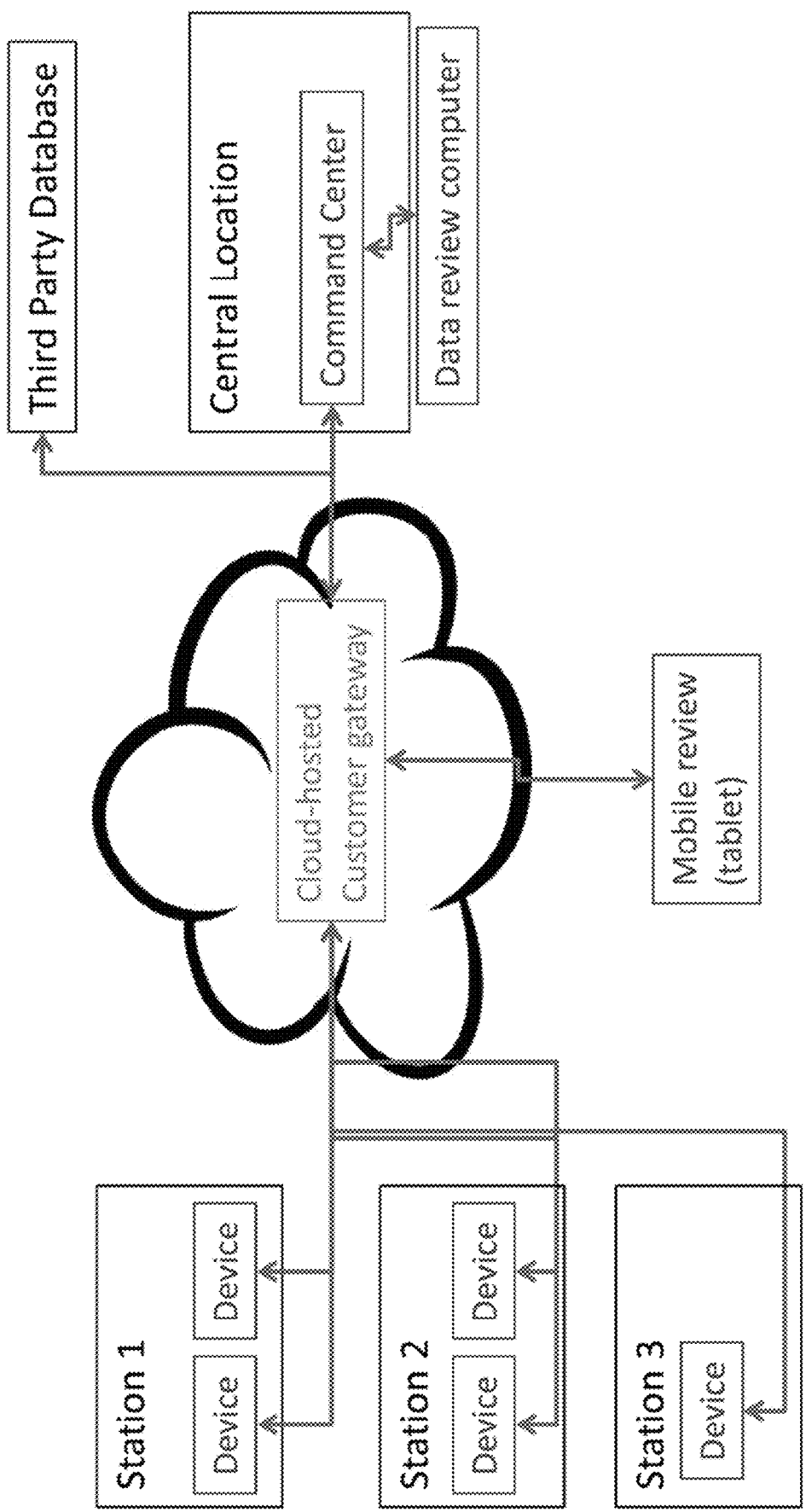
FIG. 6 shows exemplary command center connectivity architecture.

In some embodiments, a communication link is established through a cloud-based computing service, such as Microsoft Azure. As shown in FIG. 6, a central location contains the command center. The command center can communicate through a cloud-based gateway, such as Azure, with any number of remote locations. These can include, for example, stations having one or more test devices. The station can be, for example, police booking stations at a plurality of different locations. The test devices can be, for example, devices that perform rapid DNA testing. The command center also can communicate through the cloud host with one or more remote computing devices, e.g., mobile computing devices such as tablets or smart phones. The command center can communicate directly with a third party database, such as DNA profile database, such as NDNAD.

Figure 3:
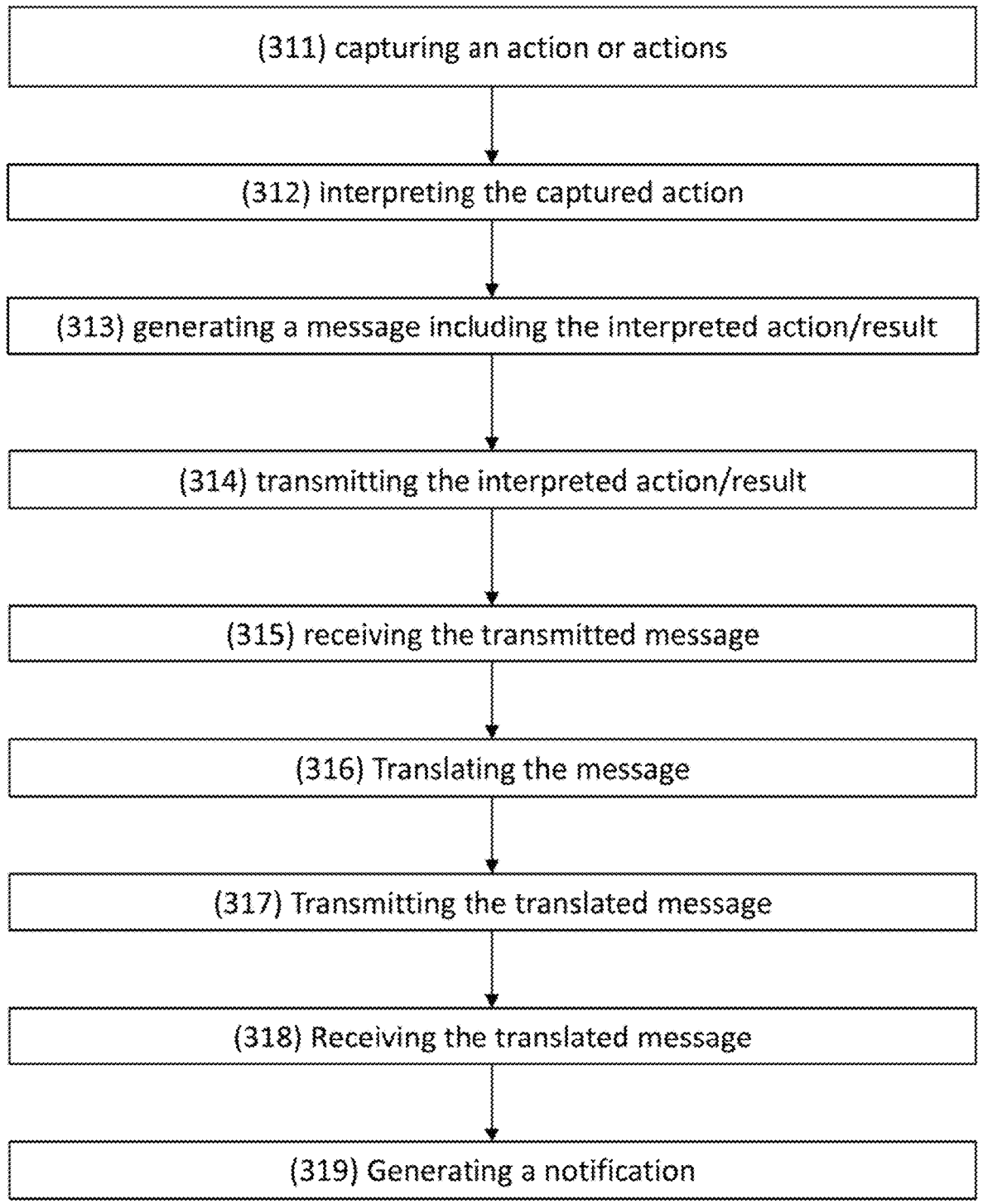
FIG. 3 shows a process flow diagram of exemplary methods to allow remote monitoring and control of a remote test equipment from a command center.

Further references will now be made to FIG. 3, which shows the process flow of a method in accordance with the present subject matter. Local test station 120 is configured for capturing an action (or actions) performed by the user on a test station 120 (e.g., using a touchscreen of the mobile device) or by the test machine on its own at 311.

Test station 120 is also configured for interpreting the captured action and the result of the action at 312, generating a message including the interpreted action/result at 313, and transmitting the interpreted actions to command center 110 at 314. In one example, the action can be machine action such as a consumable material counter that periodically sends out a report on remaining consumables. In another example, the action can be commands sent from the central command center to the test device 120 to perform self-diagnostic, report on remaining consumables, or to play a help script or video for a user, among others.

Command center 110 is configured for receiving the transmitted message from test station applications 120 at 315, translating the message at 316, and transmitting the translated message to the central command center 110 (using a client plugin, for example) at 317. Client plugin is configured for receiving the translated message at 318, and generating a notification at 319. Although only a single test station 120 and a single application are discussed in FIG. 3, it should be noted that the command center 110 can be configured to communicate among a plurality of test station applications and/or applications, e.g., to allow multiple users to access one or more applications.

In some variations, one or more (e.g., including all) of the components are independent and/or communicate with each other via internet sockets to provide high-speed communication and/or handle high traffic volumes. This ensures that the communications are timely and without errors/loss. Internet sockets can also provide acknowledgements of the transmissions.

In some variations, both test station 120 and client plugin can send and receive messages (and/or other data) through command center 110. This provides scalability in situations with a large number of users and/or applications. In some variations, each user can, for example, perform an STR test (or perform an action) and send it back to the application. Once accepted, the new information can be updated (or the relevant information can be updated) and shared with other users.

In some variations, command center 110 translates the received messages and transmits the translated messages in a First-In-First-Out (FIFO) manner. In some variations, each message can also include time-stamp data.

Figure 4:
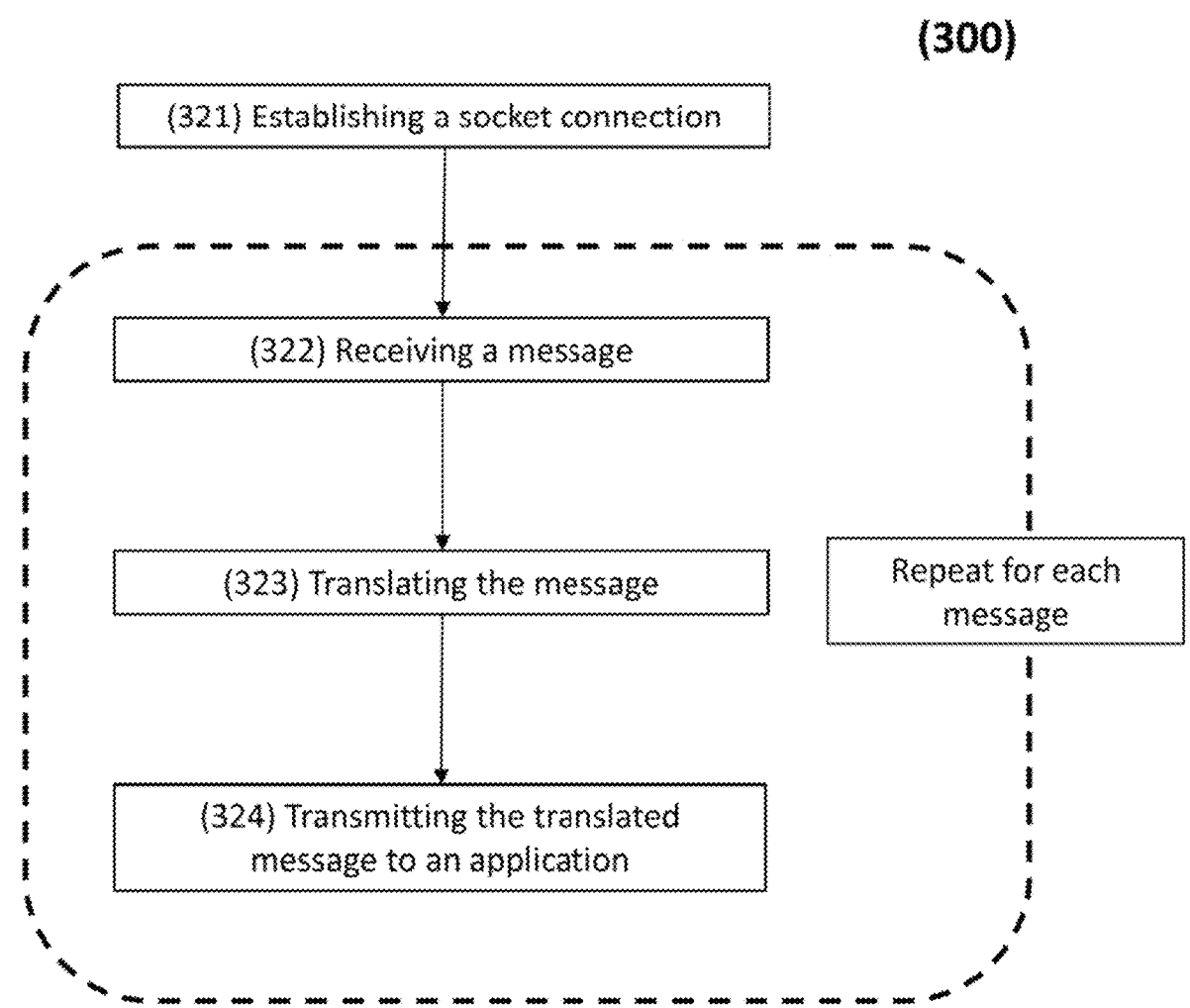
FIG. 4 shows a process flow diagram of exemplary methods to allow remote monitoring and control of a remote test equipment from a command center.

FIG. 4 is a process flow diagram of a method 300 implementing a command center 110 in accordance with the present subject matter. At 321, a socket connection is established with a mobile device. 321 is repeated for each additional mobile device(S). For each message transmitted by the test station 120 (e.g., representing a user-action such as a multi-touch gesture performed by a user using the mobile device), method 300 receives the message at 322, translates the message into a translated message including one or more predetermined parameters at 323, and transmits the translated message to an application for performing an application action corresponding to the user-action based on the translated message at 324. 322-324 are repeated for each message from each of the connected mobile devices.

In some variations, command center 110 creates a standardized translation for each received message. For example, each received message can be translated into smaller packages to be transmitted. In some variations, different actions (e.g. different gesture/action) can share as many parameters as possible to allow the messages to be compact.

In some variations, client plugin can be configured such that after the host application has loaded, it will initiate a socket connection over to command center 110. Upon a successful connection, client plugin can register itself with command center 110, which then sends a list of user details currently connected to the client plugin. When the host application closes the corresponding socket connection between client plugin and command center 110, command center 110 can disconnect from the test station 120 as well. Similarly, the severance of connection between test station 120 and command center 110 can be automatically detected by command center 110. The difference is that this information can optionally not be sent back to the connected mobile application, and/or allow automatic reconnection from test station 120 back to client plugin once it has been restarted. The client plugin can be Javascript class with websocket capabilities.

In some variations, the command center 110 can be configured to run as a daemon service, and to listen to incoming messages from both the test station application and the client plugin at designated ports. These can be run as a shared or dedicated service depending on the requirements. In some variations, the client plugin can be configured to enable remote monitoring and control of the test equipment through code.

A daemon is a computer program that runs as a background process, rather than being under the direct control of an interactive user. For example, syslogd is the daemon that implements the system logging facility and sshd is a daemon that services incoming SSH connections. In a Unix environment, the parent process of a daemon is often, but not always, the init process. A daemon is usually either created by a process forking a child process and then immediately exiting, thus causing init to adopt the child process, or by the init process directly launching the daemon. In addition, a daemon launched by forking and exiting typically must perform other operations, such as dissociating the process from any controlling terminal (tty). Such procedures are often implemented in various convenience routines such as daemon(3) in Unix. Systems often start daemons at boot time and serve the function of responding to network requests, hardware activity, or other programs by performing some task. Daemons can also configure hardware (like udevd on some Linux systems), run scheduled tasks (like cron), and perform a variety of other tasks.

IX. Computers

Aspects of the subject matter described herein can be embodied in systems, apparatus, methods, and or articles depending on the desired configuration. In particular, various implementations of the subject matter described herein can be realized in digital electronic circuitry, integrated circuitry, specially designed application specific integrated circuits (ASICs), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs, which can also be referred to programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, the subject matter described herein can be implemented on a computer having a display device, such as for example a cathode ray tube (CRT) or a liquid crystal display (LCD) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

Figure 5:
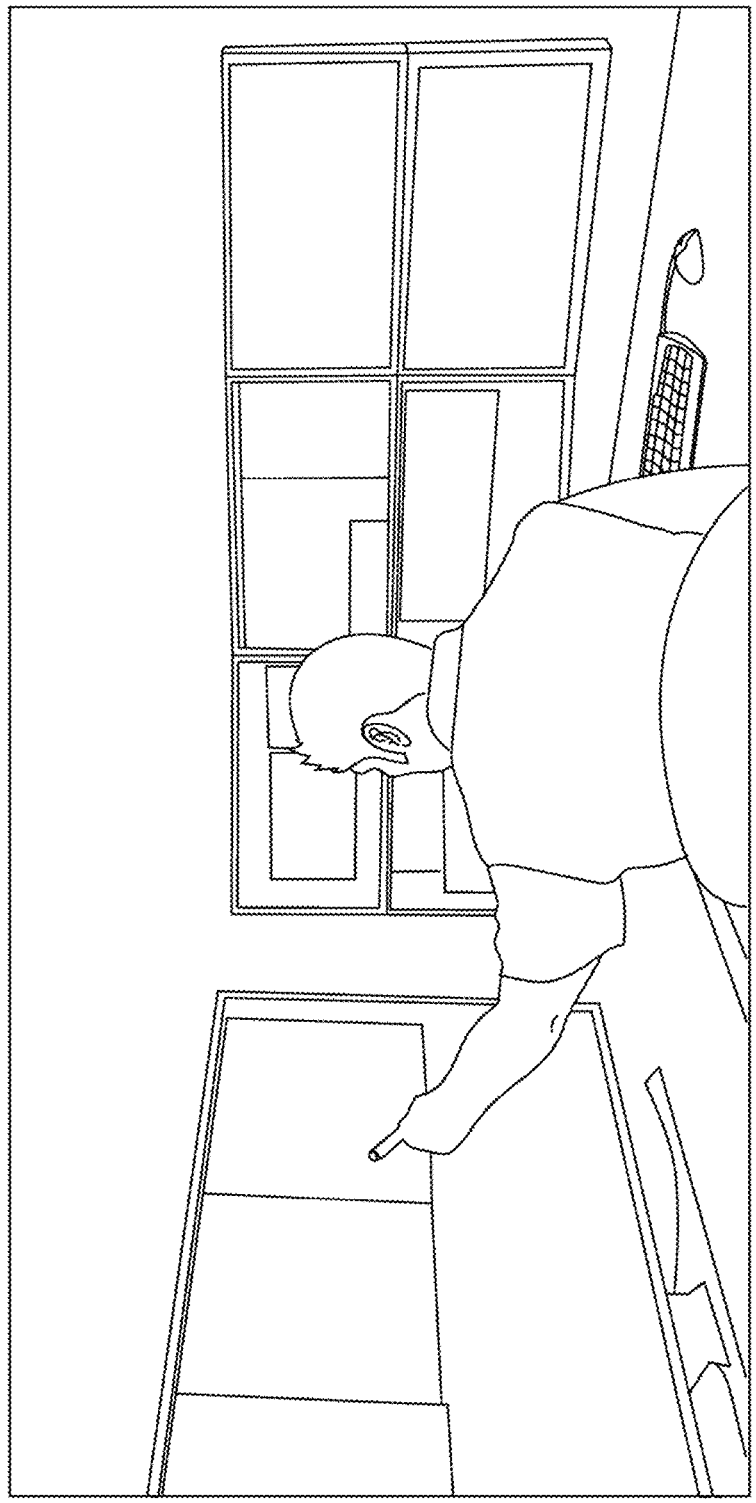
FIG. 5 shows an exemplary command center user interface.

FIG. 5 shows an exemplary command center user interface. The command center provides a plurality of screens, each controlling a remote test equipment. A central console allows one expert or trained user to help/support a number of field test equipment sites. To remove some of the manpower costs and to reduce potential security breaches, services are available that transfer some of the functionality provided by the on-premise test equipment 120 to an offsite location such as the central command center 110. Additionally, some customers may outsource their support needs to a third party provider such as the operations service provider 102. Typically, these providers set up the business or company forensic testing network, house the computers needed for the customer's forensic network, and provide the manpower necessary to keep the network supported and running. Outsourcing the forensic network may reduce the manpower and support necessary to maintain personnel and equipment typically housed on-premise, but outsourcing the entire network may result in decreased speed and efficiency to the client accessing the shared resources via the servers. The control center allows cost saving yet maintains the efficiency needed by the customer such as a city or county law enforcement agency.

The subject matter described herein can be implemented in a computing system that includes a back-end component, such as for example one or more data servers, or that includes a middleware component, such as for example one or more application servers, or that includes a front-end component, such as for example one or more client computers having a graphical user interface or a Web browser through which a user can interact with an implementation of the subject matter described herein, or any combination of such back-end, middleware, or front-end components. A client and server are generally, but not exclusively, remote from each other and typically interact through a communication network, although the components of the system can be interconnected by any form or medium of digital data communication. Examples of communication networks include, but are not limited to, a local area network ("LAN"), a wide area network ("WAN"), and the Internet. The relationship of client and server arises by virtue of computer programs running on the respective computers and having a client-server relationship to each other.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and or described herein do not necessarily require the particular order shown, or sequential order, to achieve desirable results. The scope of the following claims may include other implementations or embodiments.

X. Examples

One aspect of the disclosure provides a command center including a computer. In some implementations, the computer comprises at least one network communications interface, at least one display screen and user interface, and one or more processors. In some implementations, the at least one network communications interface is configured to establish two-way communication with a plurality of sites remote from a command center.

In some implementations, the at least one display screen and user interface includes a display device such as an LED or LCD display configured to display one or more graphical user interfaces and/or one or more text-based user interfaces. In some implementations, a display device includes a touch screen allowing user input by touching a surface (e.g., a capacitive surface). In some implementations, the user interface includes one or more physical input devices (e.g., a mouse, a keyboard, and a display device) and graphical elements shown on a screen of the display device (e.g., a mouse cursor and one or more graphical user interfaces or text-based windows or terminals).

Figure 7:
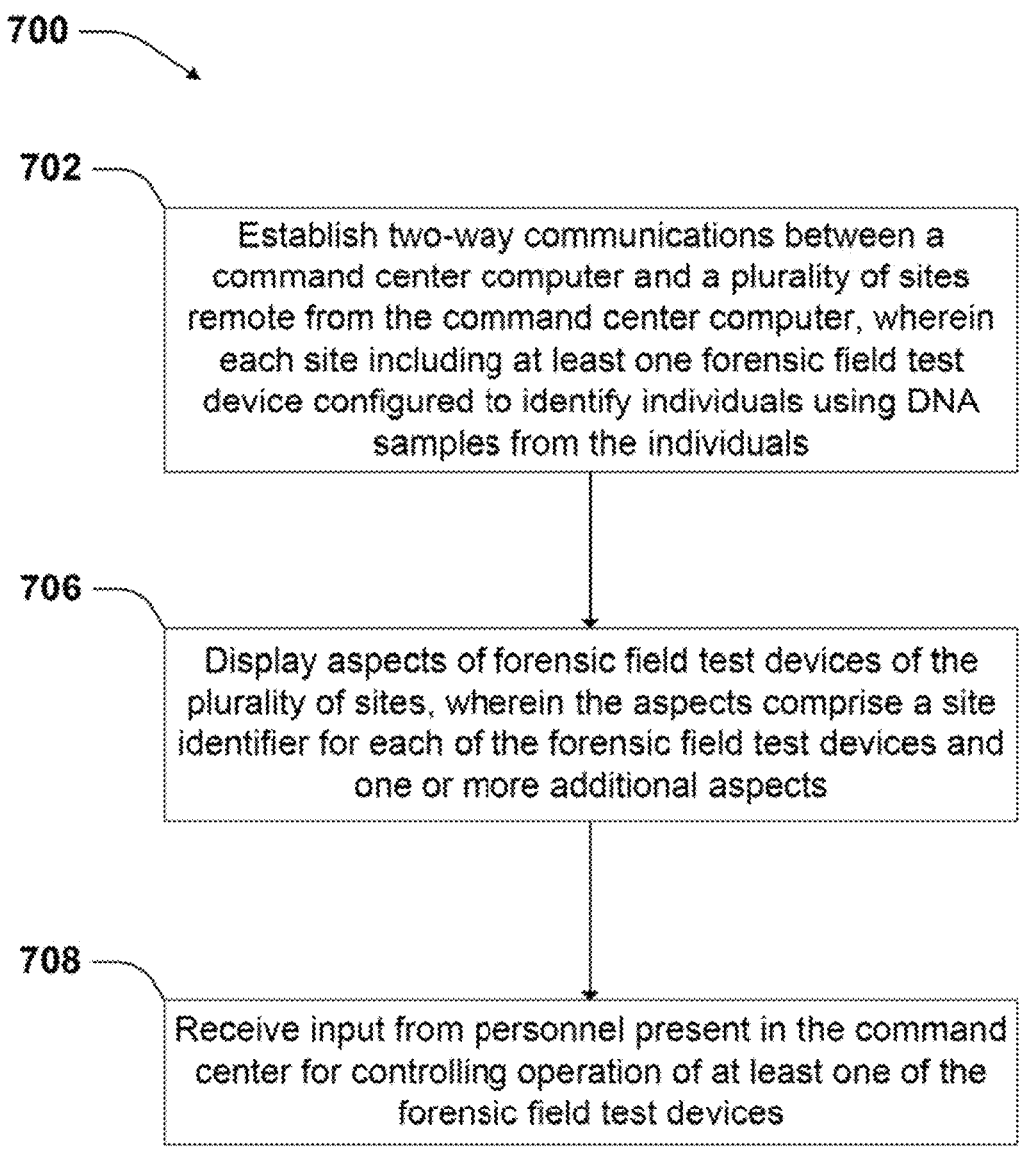
FIG. 7 illustrates a diagram of a process for operating a command center and communicating with one or more forensic field test devices.

The command center can be employed to implement a process shown in FIG. 7. FIG. 7 illustrates a diagram of a process 700 for operating a command center and communicating with one or more forensic field test devices. Process 700 involves establishing communications between a command center computer and the plurality of sites that are remote from the command center computer, with each site including at least one forensic field test device that is configured to identify individuals using DNA samples from the individuals. See block 702.

In some implementations, each site comprises at least one field test device that is selected from a biochemical testing device, a biometric testing device (e.g., a finger print analysis system), or a diagnostic device. In some implementations, each site of a plurality of sites remote from the command center includes at least one forensic field test device configured to identify individuals using DNA samples from the individuals. In some implementations, the forensic field test device comprises a biochemical testing device. In some implementations, the biochemical testing device comprises an electrophoresis device. In some implementations, the biochemical testing device includes a sequencing device. In some implementations, the biochemical device includes a next generation sequencing system. In some implementations, the field test device includes a diagnostic test device, such as an x-ray device, an MRI device, a CAT scan device, PET scan device, etc. In some implementations, the command center can be located in a central medical facilities such as a regional hospital.

Process 700 involves displaying, using the display device and user interface of the command center, aspects of forensic field test devices of the plurality of sites, wherein the aspects include a site identifier for each of the forensic field test devices and one or more additional aspects. See block 706. An aspect of the field test device refers to a property, characteristic, or attribute of the field test device, as well as data and information that are associated with or attributable to the field test device. In some implementations, the one or more additional aspects include one or more of the following: the current status of at least one of the forensic test devices, a log of operations of at least one of the forensic field test devices, an instrument run list of at least one of the forensic field test devices, a status of consumables of at least one of the forensic field test devices, and operator information of at least one of the forensic field test devices.

In some implementations, a log of operations of a forensic field test device may include a list of operations performed by the test device (e.g., sample intake, analysis, result, operator/user of device, status of sample processing or data analysis). The listed operations may be time ordered and/or time stamped. Furthermore, the log of operations may be organized according to criteria other than or in addition to time. For instance, the operations may be sorted by operators or by types of tests or statuses of tests (e.g., completed or failed tests).

In some implementations, a site identifier of a field test device includes graphical and/or textual information representing a site hosting the field test device. For instance, a site identifier may be a graphical icon associated with a site, ID or number associated with the site, a graphical name associated with the site, or combinations thereof.

In some implementations, one or more status of a test device may be displayed, wherein the statuses include but are not limited to on/off status, run time, network status, operational conditions, consumables supply conditions, and other statuses as further described herein.

In some implementations, operated information of the device may be displayed. An operator of the test device may be an authorized user of the device. Information such as the operator's name, authorization levels, devices authorized to be operated by the operator, and other information described herein may be displayed.

Process 700 also involves receiving input from personnel present in the command center for controlling operation of at least one of the forensic field test devices. See block 708. The input may be received using a display screen and a user interface of the command center computer. Operations that can be controlled include but are not limited to turning the device on and off, locking the operation of a device thereby preventing unauthorized operation, adjusting test run parameters such as test time or reaction temperatures, and other operation as described herein. In some implementations, the field test devices automatically adjust operational parameters to account for environmental parameters such as ambient temperature, atmospheric pressure, altitude, etc.

For example, at 3000 meters, the boiling point of water decreases to about 89° C. This temperature is below some DNA melting temperatures used in PCR (e.g., about 94° C.).

Some implementations provide a device for performing a biochemical reactions, the results of which reactions depend, at least in part, on an environmental condition under which the biochemical reactions are performed. The device includes a sensor that measures the environmental condition; and software that adjusts a parameter of the performance of the biochemical reaction to compensate for the environmental condition. In some implementations, the environmental condition is selected from ambient temperature, ambient humidity, ambient barometric pressure, or elevation. In some implementations, the biochemical reaction includes PCR and the adjustment includes lowering melting temperature during thermal cycling to below the boiling point of water at the ambient barometric pressure.

In some implementations, instead of or in addition to automatically adjusting operations, the device may receive information regarding operational parameters, or instructions to adjust operations or operational parameters. For example, the command center can send an instruction to the field test device to raise or lower temperature, lengthen or decrease time of a thermal cycle, increase or decrease voltage used in electrophoresis.

Figure 8:
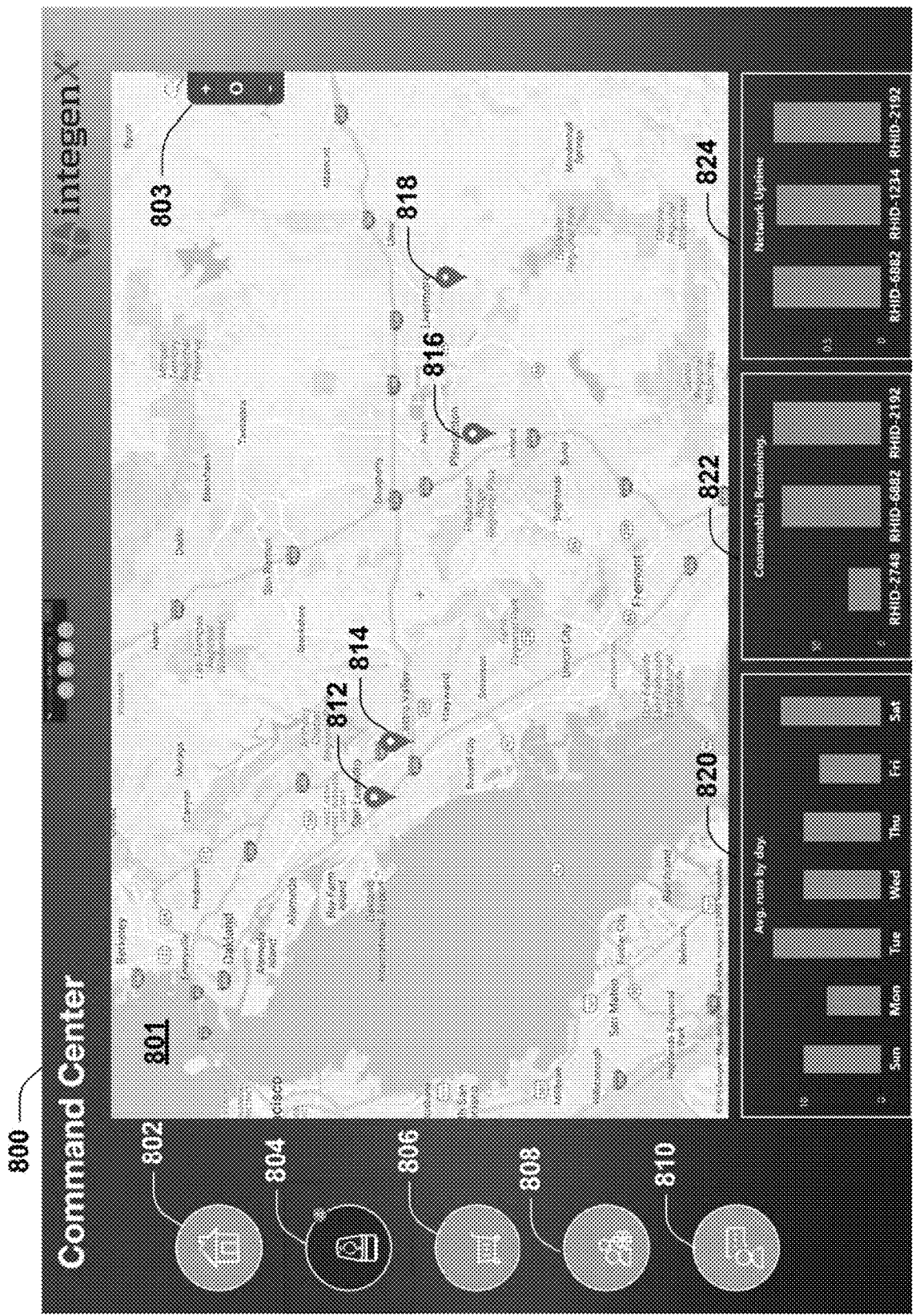
FIG. 8 is a map view activated by selecting an icon in a graphical user interface (GUI).

FIG. 8 illustrates an example of a graphical user interface as an implementation of the user interface of the command center. The graphical user interface 800 includes icons 802-810 associated with features relating to the forensic test devices or the command center. The user can select (e.g., by point and click using a mouse or touching the icon on a touch screen) one of the icons 802-810 to activate different graphical windows or elements for different features.

Illustrated in FIG. 8 is a map view 801 activated by selecting icon 804 in graphical user interface (GUI) 800. Map view 801 includes site identifiers 812-818, each of which indicates a location where at least one forensic field test device is located. In some implementations, as shown here in the figure, the map of the map view 801 may be zoomed in or out by a user e.g., by using a graphical element such as the graphical element 803.

In some implementations, the GUI 800 includes one or more elements that allow a user to direct forensic field test devices to known locations.

At the bottom of the graphical user interface 800, three graphical elements 820, 822, 824 are displayed. The graphical element 820 displays average runs of all the forensic field test devices at the sites 812, 814, 816, and 818. The average runs are displayed graphically in a bar graph, with each bar indicating the average number of runs by day of the week. In some implementations, a bar graph illustrating the runs by day may be customized to display different forensic field test devices. For instance, it can be customized to display all devices in a particular region instead of the devices located within the shown map area as illustrated. In some implementations, the bar graph may display the devices at a specific site after a user selects a site identifier representing the specific site. In some implementations, as the map area changes, the information displayed in the bar graph in boxes 802 automatically updates to reflect the forensic field test devices located in the updated map area.

Graphical user interface 800 also includes element 822 that includes a bar graph displaying consumables remaining for forensic field test devices. The bars of the graph are labeled by the device IDs of the forensic field test devices. The bar graph may indicate the number of test runs that can be carried out using the consumables remaining in the test devices. The consumables may include reagents, gel, or other consumable materials used by the forensic field test devices in performing tests.

Figure 15:
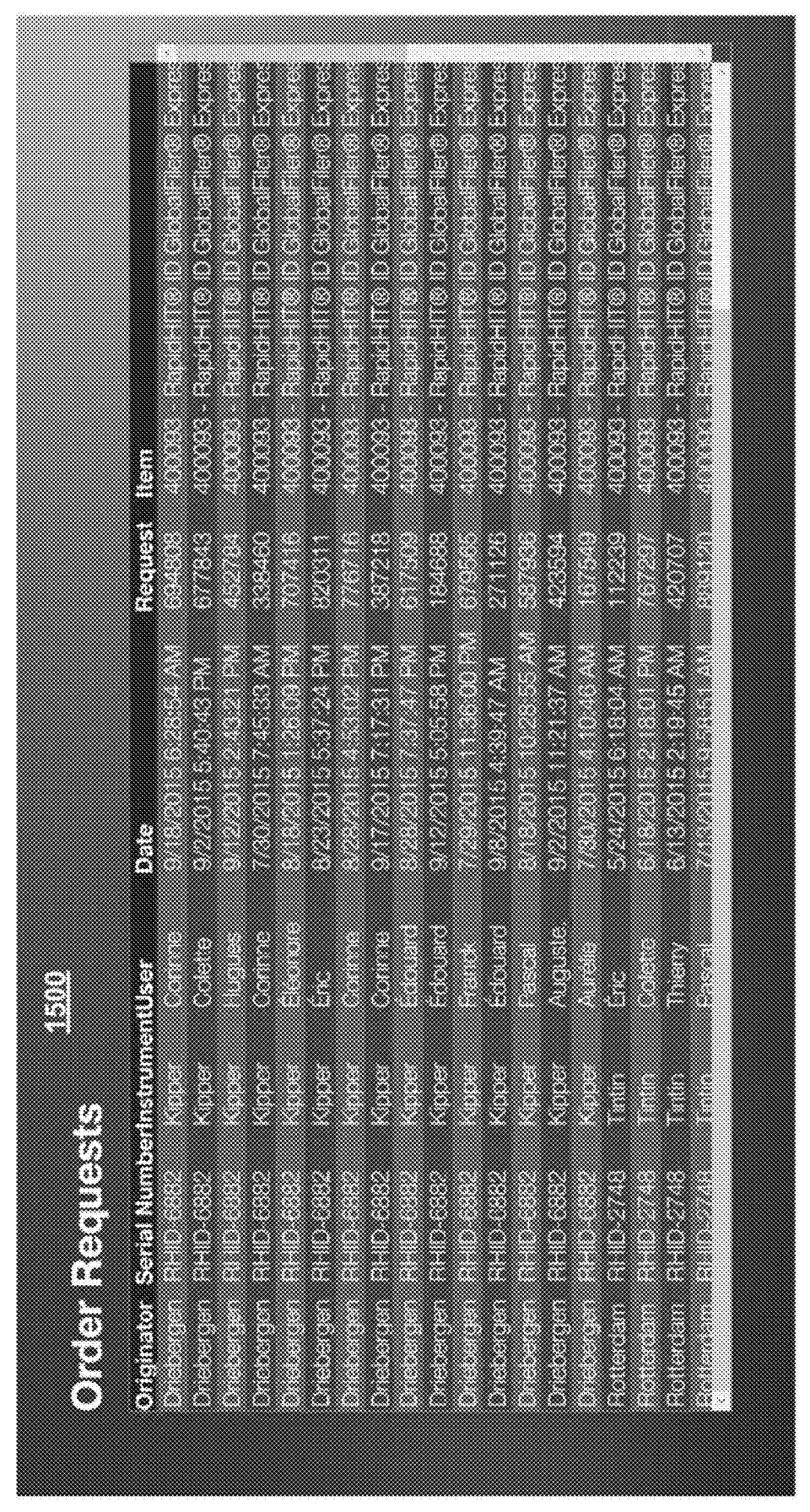

In some implementations, other information about consumables may be displayed, such as the amount left, the expiration dates of the consumables, the projected depletion time of the consumables based on the rate of use, and the conditions of the reactants. In some implementations, reminders regarding the consumables may be sent from the command center to the forensic field test devices. In some implementations, orders of the consumables may be generated manually or automatically at the forensic field test devices and sent to the command center. In some implementations, a log of the orders sent from the field test devices can be shown in a graphical user interface 1500 as illustrated in FIG. 15. FIG. 15 shows graphical user interface 1500, which can be activated by the user selecting the icon 806 in FIG. 8. In some implementations, the command center may supply or procure the consumables based on the information about the consumables of the forensic field test devices. In some implementations, as shown in FIG. 15, orders of consumables can be presented in a list that is sorted based on remaining consumables in the forensic field test devices. In some implementations, the command center can predict the depletion time of the consumables, and color code a device when the supply is predicted to be less than a particular period, e.g., two weeks. In some implementations, consumable supply management can be automated through settings, allowing the user of the command center to set the frequency of supply, the notification about supplies, etc.

Returning to FIG. 8, the graphical user interface 800 also includes element 824 that shows a bar graph indicating the status of the forensic field test devices. In the example shown, a bar graph is displayed showing the network uptime of the forensic field test devices. In some implementations, the graphical user interface can display other statuses of the forensic field test devices, such as the on and off status, the run time, the current or previous times or temperatures of reactions, pressure, elevation, humidity, and other operation parameters of the devices. The information about the statuses of the forensic field test devices can inform the user of the command center, who can then interact with the forensic field test devices or the operators thereof. For instance, the user of the command center may remotely control the forensic field test devices, provide instructions to the operators of the forensic field test devices, issue alerts, and provide supplies to the forensic field test devices.

Figure 9:
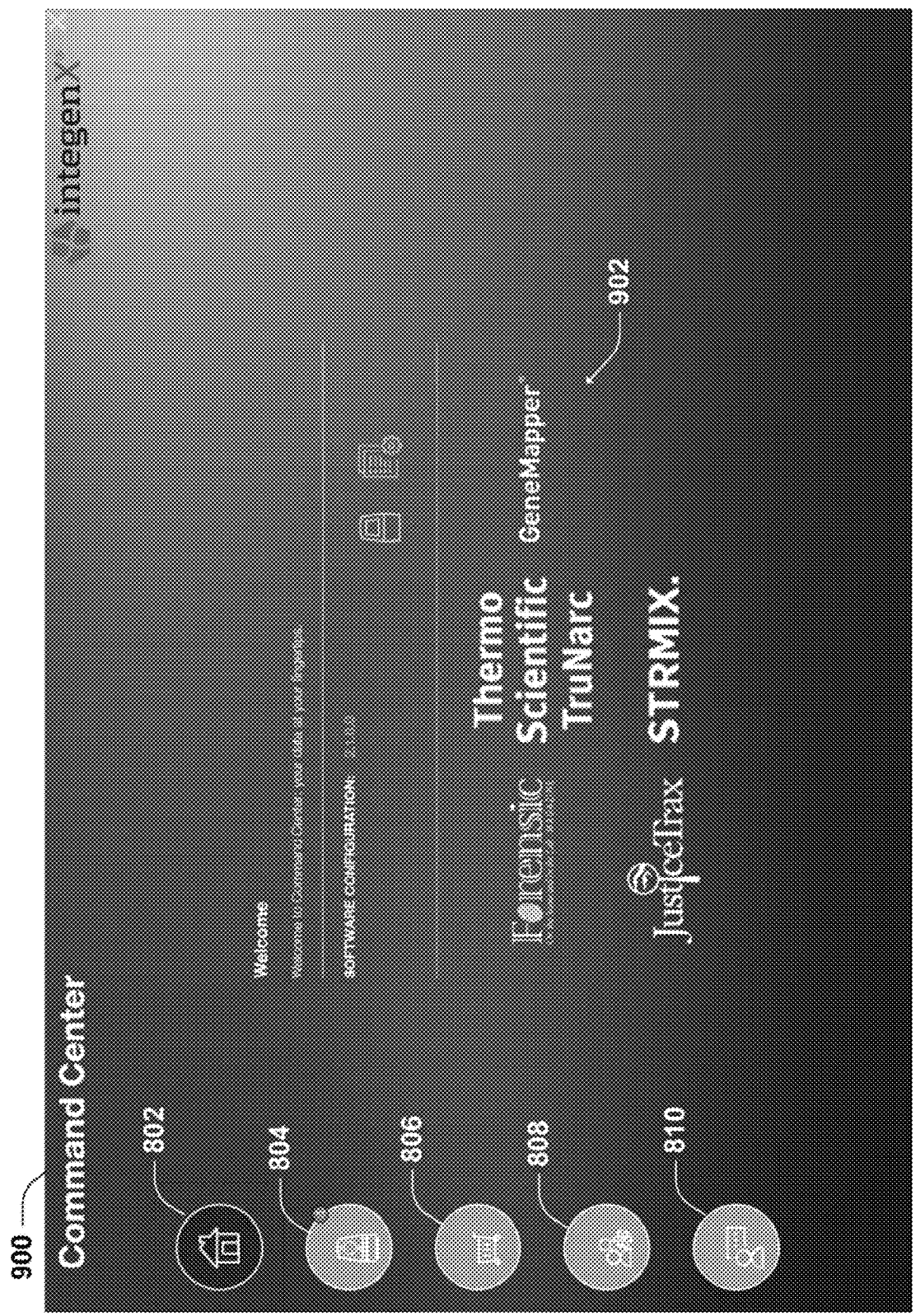
FIG. 9 illustrates a graphical user interface of the command center that appears as the default screen when the command center initiates a graphical user interface.

FIG. 9 illustrates a graphical user interface 900 of the command center that appears as the default screen when the command center initiates a graphical user interface. In some implementations, it is displayed in response to the user selection of icon 802. In some implementations, graphical user interface 900 includes one or more third-party applications. In some implementations, the applications relate to services that are of interest to personnel at the command center. In some implementations, the third-party applications relates to general forensic or law enforcement topics such as trade journals or publications. In some implementations, the third-party applications relate to forensic or legal services such as DNA fingerprinting services, DNA testing or analysis services, forensic analysis services, etc. Area 902 of graphical user interface 900 shows icons for various third-party applications. In some implementations, area 902 includes user selectable indications connecting to the one or more third-party applications services. In some implementations, referral fee or other considerations from the one or more third-party applications or services may be implemented with the command center application.

As mentioned above with reference to FIG. 8, site identifiers 812, 814, 816, and 818 shown in graphical user interface 800 and on map 801 may be selected by the user of the command center. In some implementations, the user may single click a graphical representation of the site identifier to show additional information of the site and the one or more forensic field test devices at the site. In some implementations, a new graphical user interface can be activated by performing another user gesture on the site identifier, e.g., by double-clicking a site identifier element.

Figure 10:
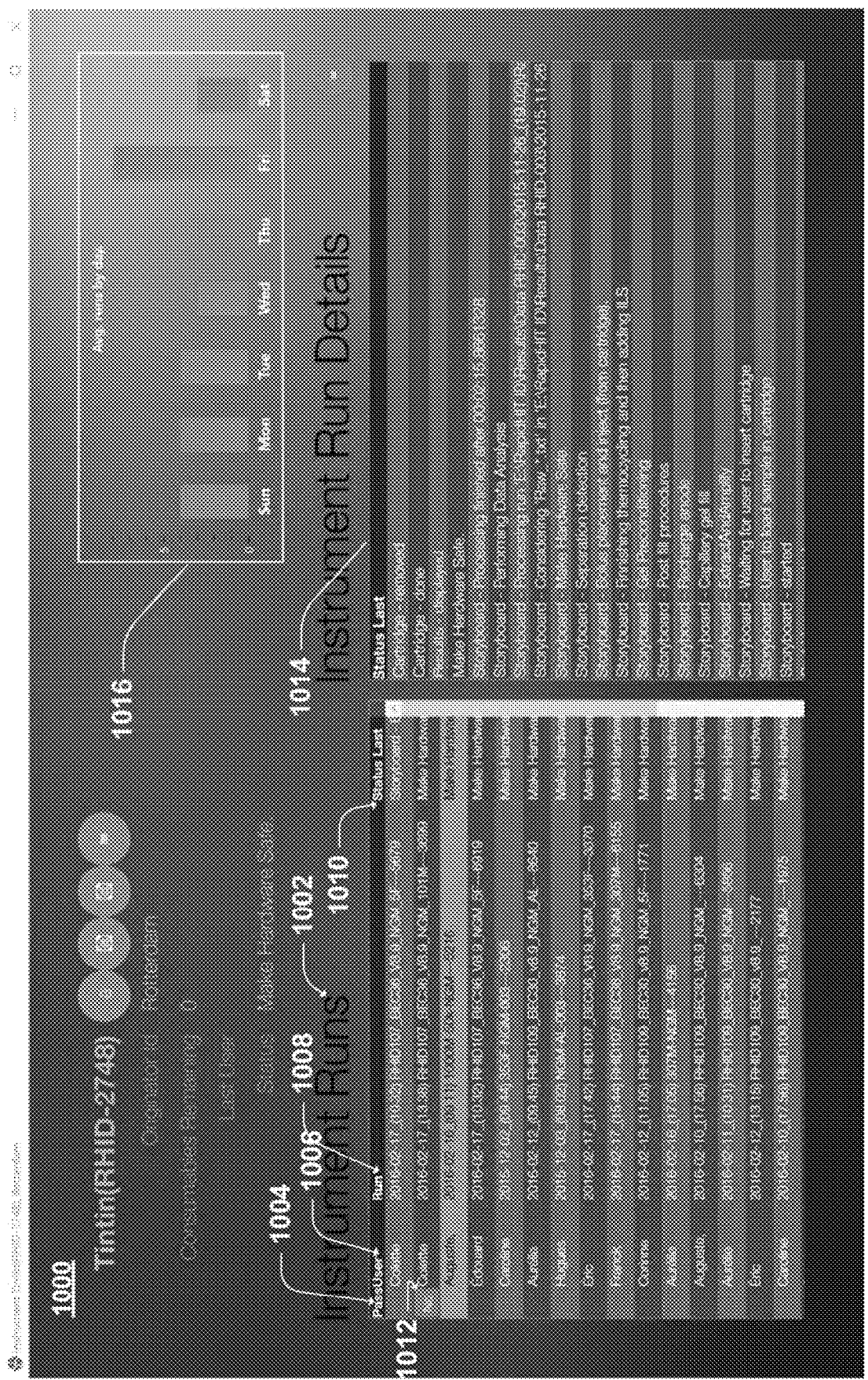
FIG. 10 shows an example of a graphical user interface activated in response to a user gesture performed on a site identifier.

FIG. 10 shows an example of a graphical user interface 1000 activated in response to a user gesture performed on the site identifier. In some implementations, graphical user interface 1000 is displayed in response to the user selecting a site identifier on map 801. The graphical user interface 1000 includes an element 1016 that shows the average runs by day for a forensic field test device at a site associated with the site identifier selected by the user. In this example, one forensic field test device is shown in the graphical user interface 1000. The graphical user interface 1000 includes an element 1002 that shows a log of operations of the forensic field test device. The log shows instrument runs at the forensic field test device. The instrument runs comprise genetic profiling tests performed at the device.

Display element 1002 shows four columns 1004, 1006, 1008 and 1010 of information associated with the instrument runs. Column 1004 indicates whether the instrument runs completed properly or passed. In some implementations, if the physical operations of the test did not complete properly, the run is flagged by an indicator. See indicator 1012. In some implementations, a run is flagged if the biochemical reactions of the test failed to complete. In some implementations, the run is flagged as not passed if the data analysis of the test is potentially unreliable or inaccurate.

Display element 1002 also includes column 1006 showing the names of the users that operate the runs of the tests, information labeling the runs at column 1008, and run status information of the device at column 1010.

In some implementations, graphical user interface 1000 also includes a display element 1014 that shows more details of an instrument run. In some implementations, display element 1014 is activated in response to the user selecting a row indicating a run in the instrument runs log in 1002. In some implementations, display element 1014 includes operation conditions and parameters of the field test device, such as cartridges, results, sample processing, data analysis, hardware operation, reagent operation, reaction condition, hardware status, time of operations, chemical reaction preparation and status, etc.

In some implementations, the instrument runs performed by the field test device relate to biochemical reactions for testing genetic profiles of biological samples. In some implementations, a test for obtaining the genetic profile includes electrophoresis reaction for detecting different STR alleles at multiple loci.

Figure 11A:
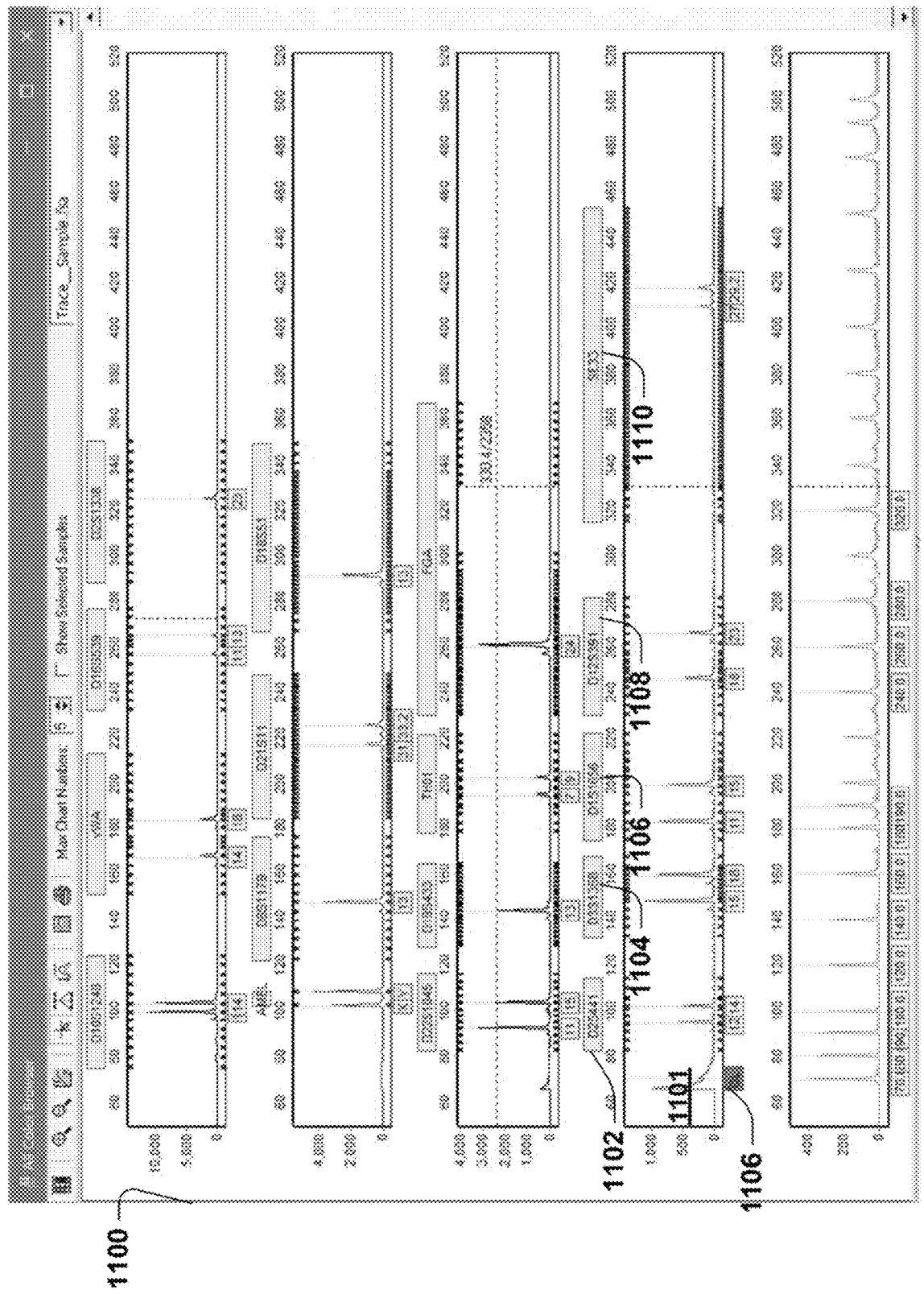
FIG. 11A shows an example of a graphical user interface for analyzing and displaying data from an instrument run.

In some implementations, further information about the data analysis from the instrument runs may be displayed by the command center. In some implementations, the user may activate a graphical user interface showing data analysis of the data collected from the instrument runs by selecting an item in the instrument runs in element 1002. FIG. 11A shows an example of a graphical user interface 1100 for analyzing and displaying data from an instrument run. Graphical user interface 1100 shows electropherograms obtained from the data of an electrophoresis test run performed by the forensic field test device. Each row in the electropherograms of FIG. 11A shows one lane of electrophoresis reaction. Each lane is multiplexed to detect multiple loci of STRs having different sizes. Plotted on the x-axis is the size of the molecule, and on the y-axis is the detected signal strength.

Row 1101 illustrates a lane for detecting STRs at loci 1102, 1104, 1106, 1108, and 1110. Shown on the X axis is the size of the STR sequences. The sizes of the loci are different, allowing multiplexing of the five loci using one lane. As is shown in FIG. 10, run 1012 is flagged as "not passed," indicating the allele calls at one of the loci in the electropherogram is potentially unreliable or inaccurate, or has another potential problem. The corresponding electropherogram in FIG. 11A is marked with an indicator 1106 showing the potentially unreliable portion of the data in the electropherogram. The data obtained from the run may or may not require a rerun of the test. In some implementations, in this situation a genetic profile may not be generated, or the genetic profile may be potentially unreliable. A further determination of the run requires review and input from a human expert.

In many situations, the field test sites do not have the personnel with the expertise to review and analyze the electropherograms. In some implementations, an expert at the command center may review and analyze the instrument runs that have been flagged as potentially problematic or unreliable. In some implementations, flagged instrument runs may be forwarded to one or more experts remote from the command center for further review and analysis. In some implementations, the flagged instrument runs may be distributed to a cloud computing platform. Cloud sourcing the analysis and review to remote experts is especially beneficial to a large network of devices producing large amount of data. In some implementations, experts remote from the command center may be provided with a user interface similar to the user interface shown in FIG. 11A, on a remote server or on a local computer.

The ability to have the test data reviewed and analyzed at a location remote from the physical location of the test device, and the ability to cloud source the data review and analysis provide technological improvements that can significantly change the efficiency of the tests. When used in many real world applications such as in the criminal justice system, these improvements can result in catching otherwise missed criminals, or saving lives that otherwise would have been lost, due to missing the critical window of opportunity.

Figure 11B:
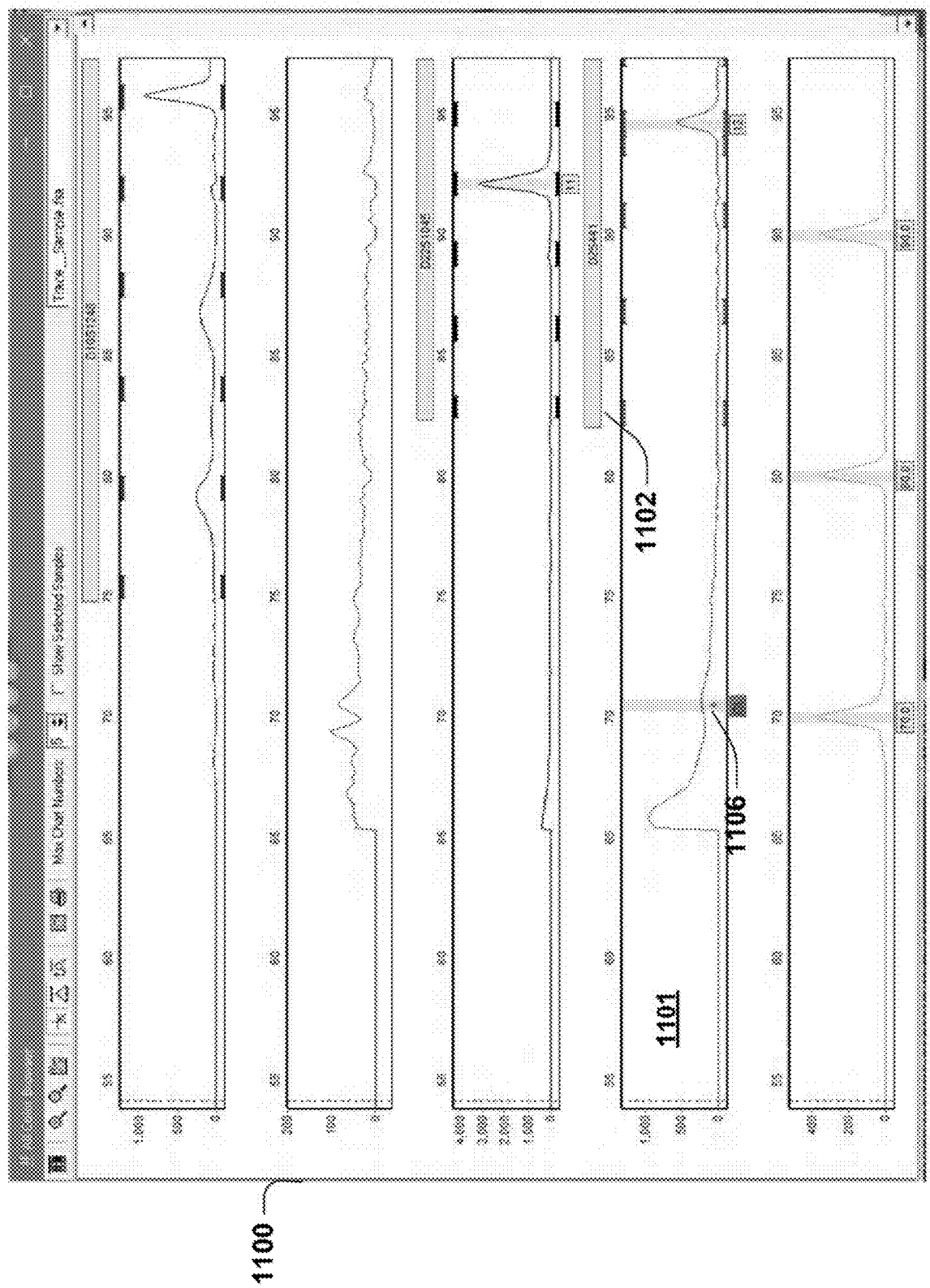
FIG. 11B shows a graphical user interface that includes a zoomed in display of the data including the data flagged at a location.

In some implementations, the reviewer of the electropherogram of the user graphical interface 1100 may zoom into various portions of the electropherogram, including a portion that has been flagged as potentially unreliable or problematic. FIG. 11B shows graphical user interface 1100 that includes a zoomed in display of the data including the data flagged at location 1106 as potentially unreliable for locus 1102. See also a portion of the electropherogram that has a small peak following a large peak at location 1106. In some implementations, an expert may provide input about the potentially unreliable portion of the electropherogram.

Figure 11C:
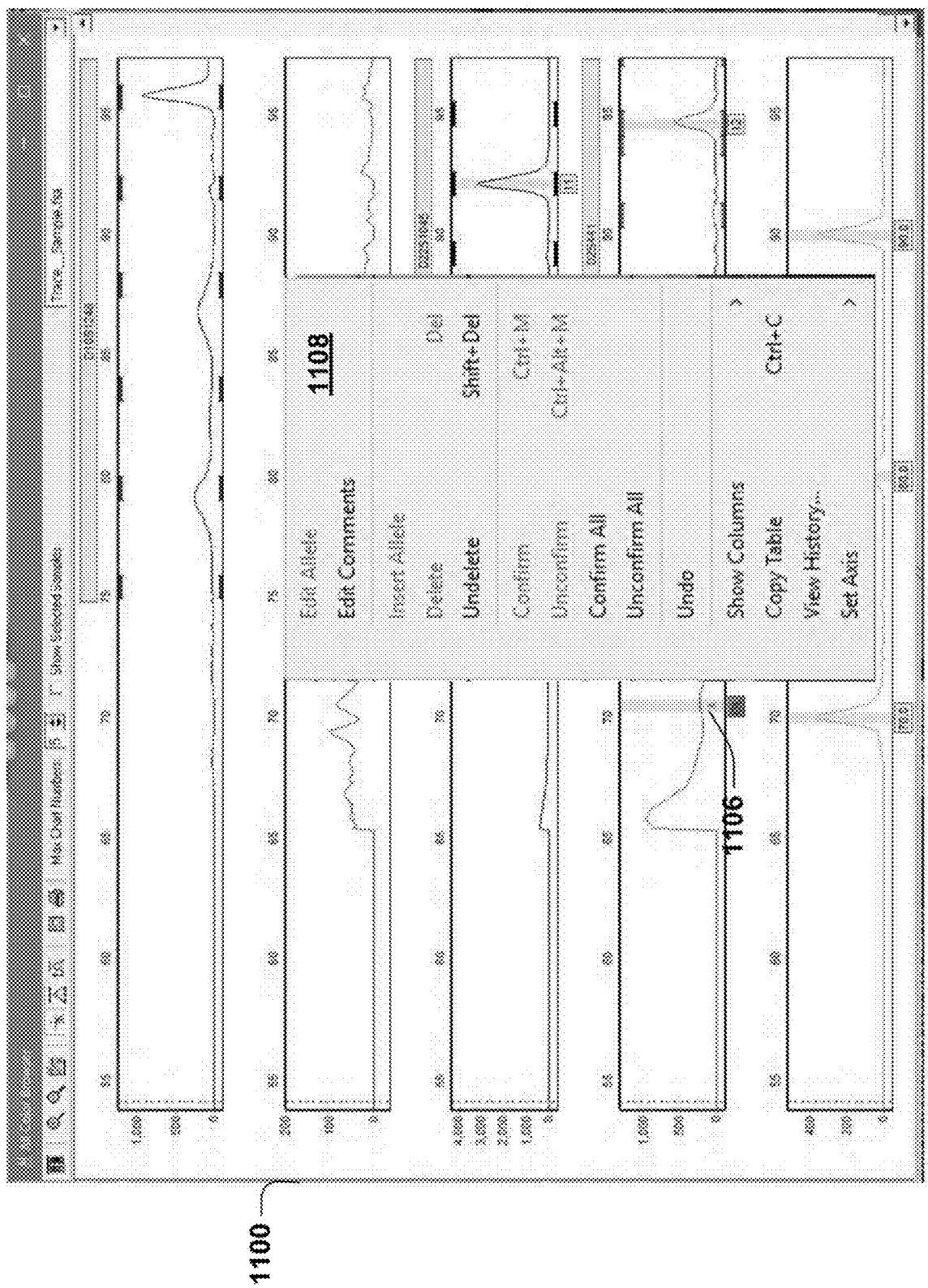
FIG. 11C shows a pop-up window that the user of a graphical user interface may activate to provide input about selected data.

For instance, the expert may activate an interface such as a pop-up window to provide input regarding the potentially unreliable data. FIG. 11C shows a pop-up window 1108 that the user of graphical user interface 1100 may activate to provide input about selected data (such as data at location 1106). For instance, the expert may confirm the data as being acceptable, thereby clearing the unreliable or problematic status of the data. In some implementations, the expert may provide other input such as providing comments or deleting a flag of the data.

Figure 12A:
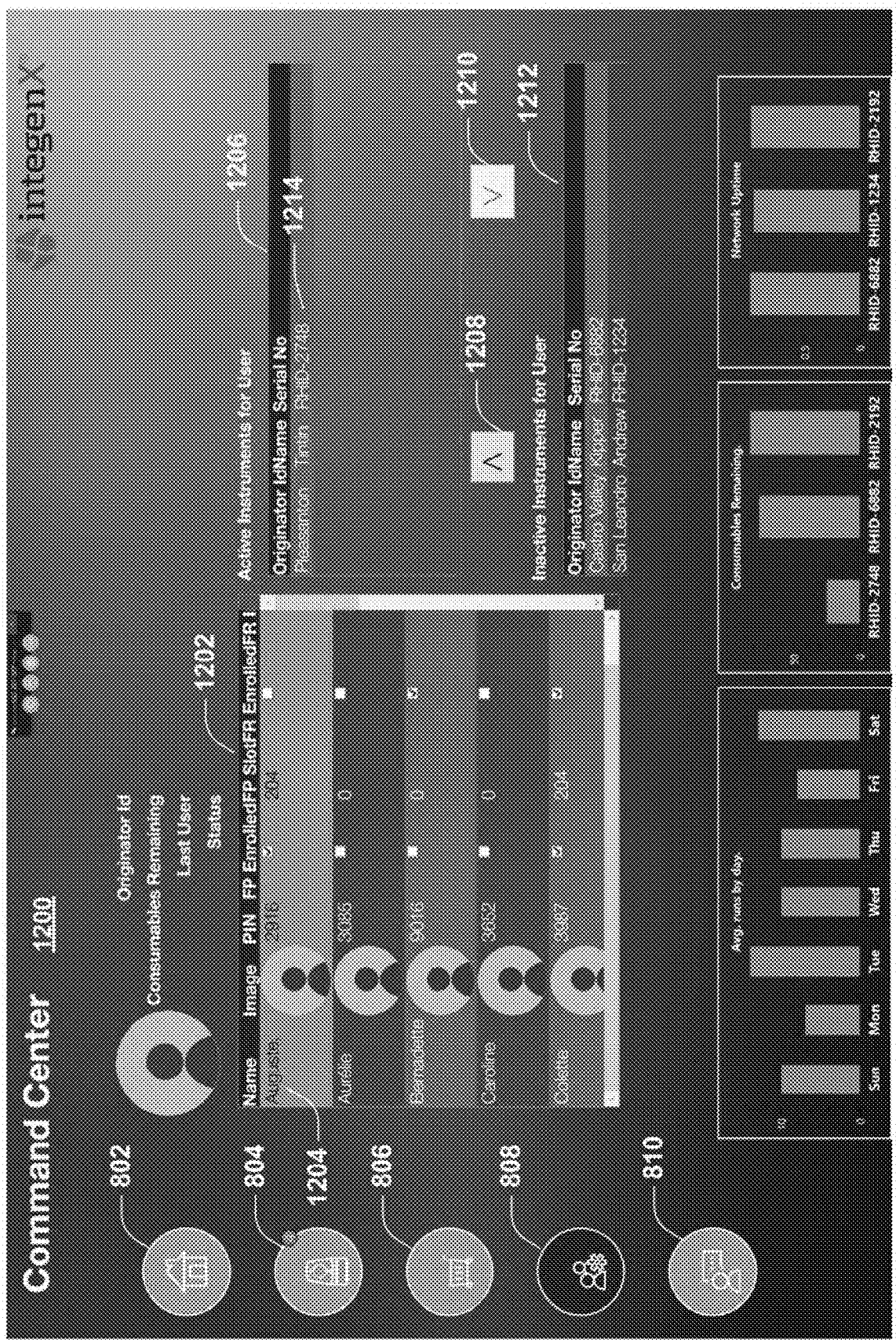
FIG. 12A shows a graphical user interface including information about operators or users of the forensic field test devices.

FIG. 12A shows a graphical user interface 1200 including information about operators or users of the forensic field test devices. In some implementations, the graphical user interface 1200 is activated by a user selecting icon 808. In some implementations, operators of the devices in a particular region may be shown in the graphical user interface 1200.

Operators of the forensic field test devices at sites shown on map 801 in FIG. 8 may be displayed in a graphical element 1202. In other implementations, other sets of operators may be displayed. Element 1202 includes multiple rows of information for operators. Element 1202 also includes multiple columns for displaying different types of information of the operators, including the name, the image, the personal ID number, the enrollment status of fingerprint access to the devices, the fingerprint slot number, and the enrollment status of face recognition of the operator. As shown, element 1202 is implemented as a scrollable window.

Graphical user interface 1200 includes elements 1206 showing active instruments authorized to be used by a particular user and element 1212 showing inactive instruments not authorized to be used by the user. In some implementations, the elements 1206 and element 1212 are activated by selecting a user in 1202. Display element 1206 also shows additional information regarding device 1214, including the originator or location of the device, the name of the device, and the serial number of the device.

Figure 12B:
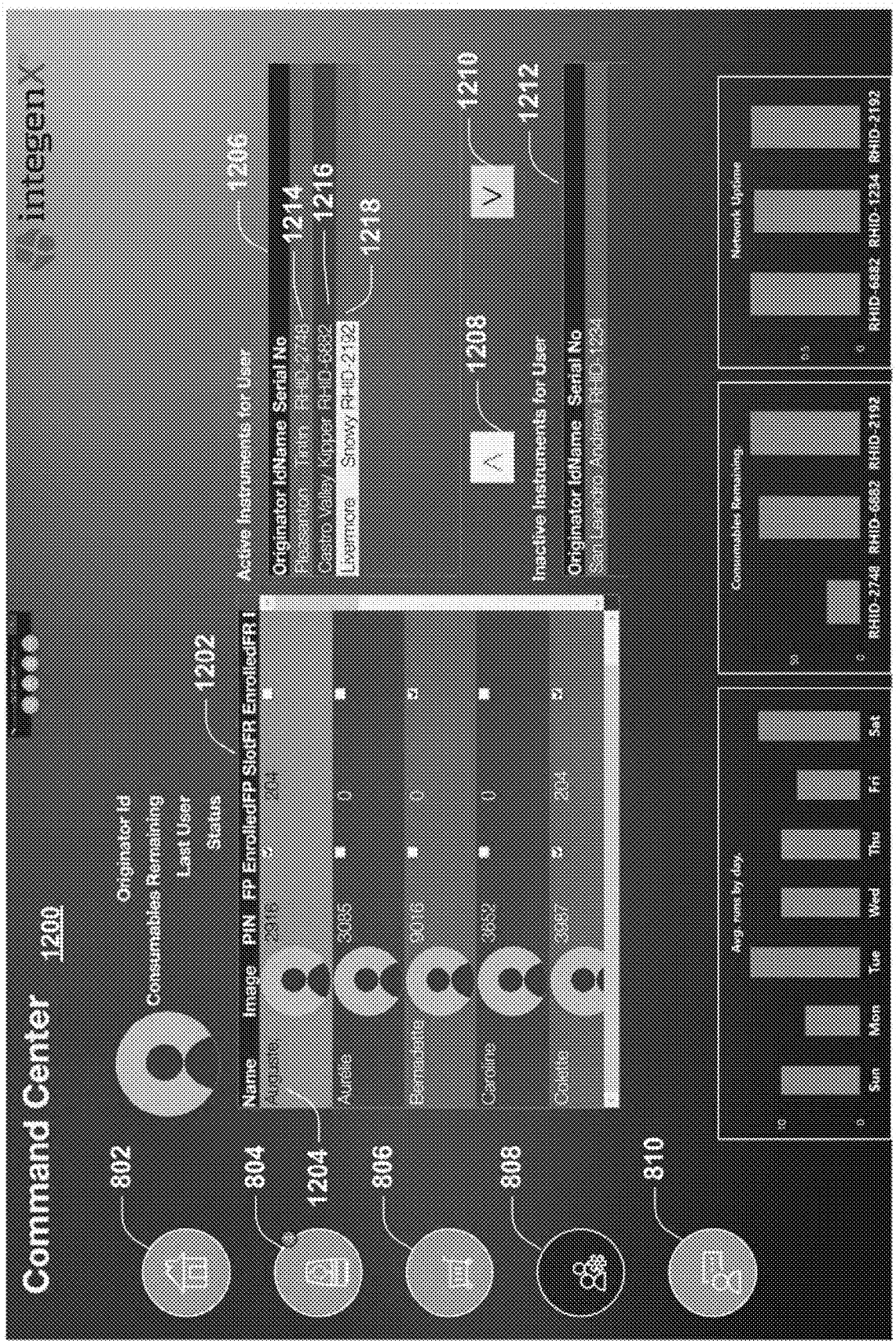
FIG. 12B shows that devices have been assigned to a user.

In some implementations, the active/inactive assignment of the instruments to a user may be changed using graphical elements 1208 and 1210. For instance, FIG. 12A shows that device 1214 is active and authorized to be used by user 1204. In some implementations, the instruments may be assigned or removed for the user using buttons 1208 and 1210. For instance, FIG. 12B shows that devices 1216 and 1218 have been assigned to user 1204 by selecting a device in 1212 and clicking icon 1208. An instrument may be removed or deactivated for a user by selecting the device and clicking icon 1210.

In some implementations, the command center allows management of field test device operator logins across instruments. For example, in some implementations, an operator may be permitted to log in on multiple field test devices, which may be provided in one geographic location or multiple such locations. In some implementations, biometric login information (e.g., fingerprint and facial recognition) of a same operator is synchronized among and/or transferred across multiple devices.

Figure 13:
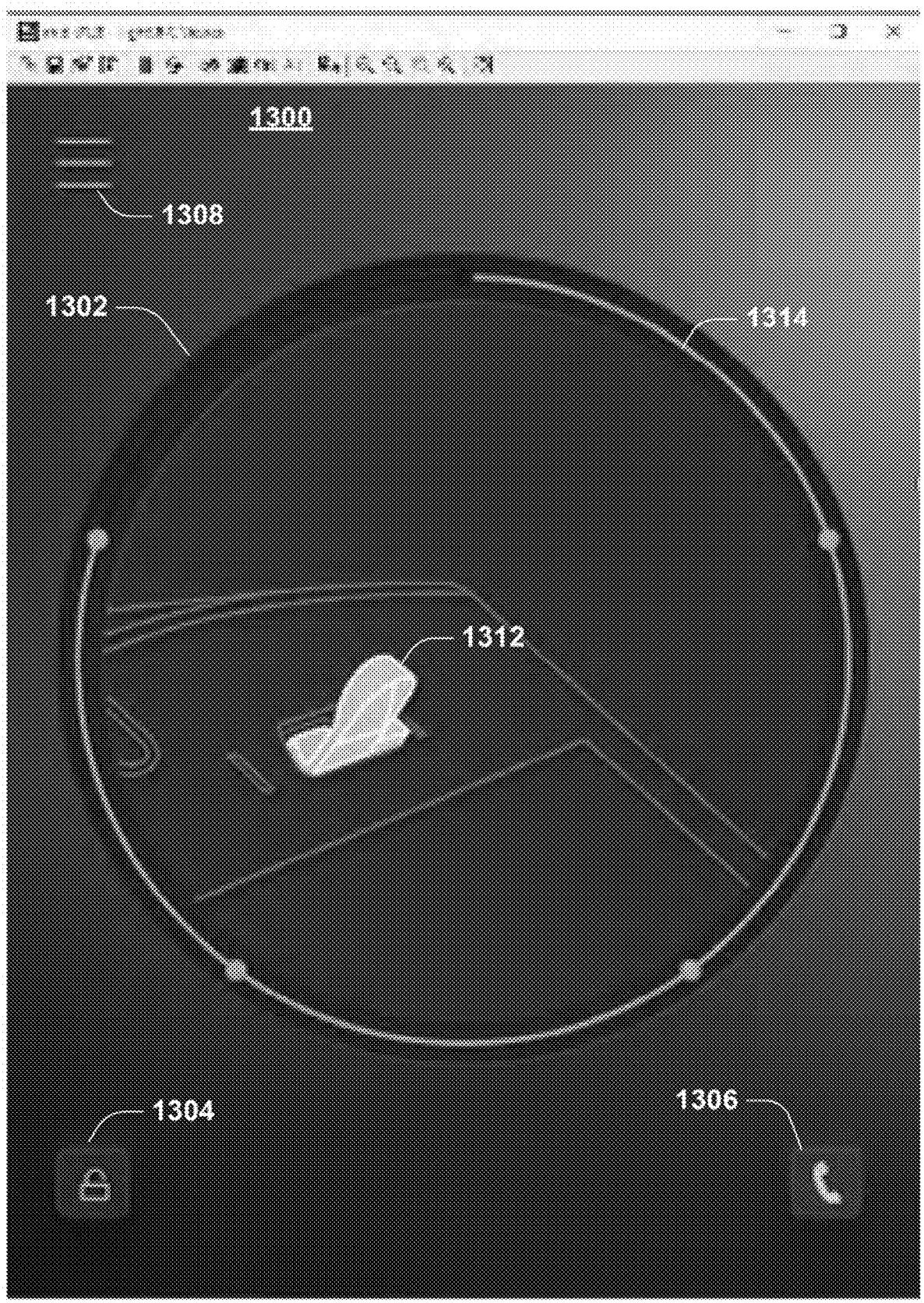
FIG. 13 shows a graphical user interface that depicts the operation and features of the forensic field test device.

FIG. 13 shows a graphical user interface 1300 that depicts the operation and features of a forensic field test device. In some implementations, graphical user interface 1300 is activated by selecting icon 810 in FIG. 8. In some implementations, the information and graphics shown in graphical user interface 1300 mirror that shown on the display of the forensic field test device.

As shown in graphical user interface 1300, the circular graphical element 1302 indicates a test operation of the forensic field test device. Graphical element 1312 indicates that a sample container has been inserted properly into a receiving slot on the forensic field test device. In some implementations, the sample container is configured to contain DNA samples, such as saliva, tissue smear, blood, plasma, bodily fluid, or tissue samples.

In some implementations, the forensic field test device can analyze a DNA sample in about two hours. The circular graphical element 1314 indicates the progress of the sample processing and analysis, with the lighter line completing the circle when the process is complete.

In some implementations, graphical user interface 1300 includes an icon 1304 that a user may select. By selecting icon 1304, the user of the command center can remotely lock the field test device, preventing unauthorized operation of the forensic field test device.

The graphical user interface 1300 also includes an icon 1306. By selecting icon 1306, the user may initiate an audio and/or video communication between the forensic field test device and the command center. In some implementations, selecting icon 1306 activates graphical user interface 1400.

Figure 14:
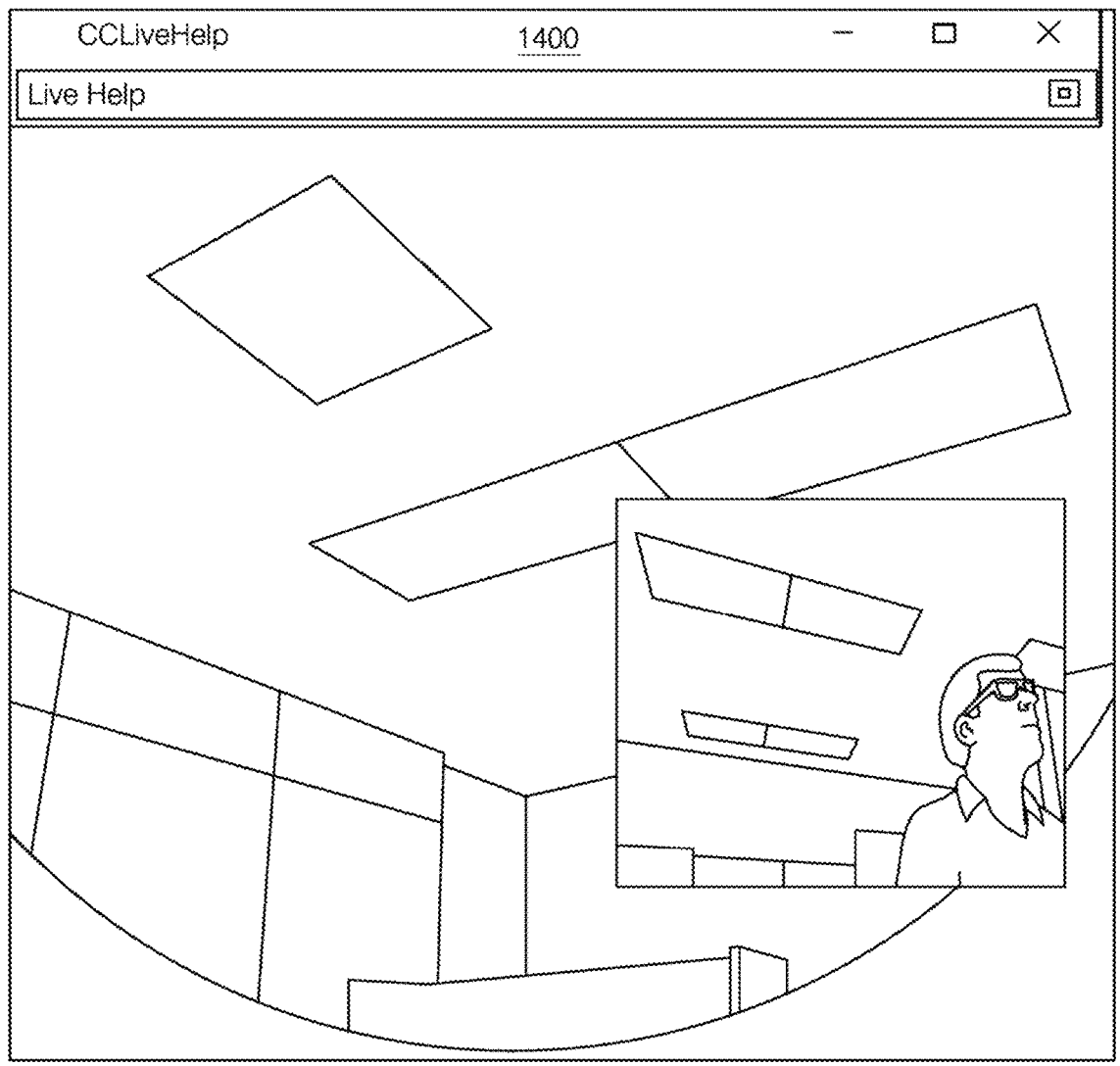
FIG. 14 shows a graphical user interface including live video feeds from the forensic field test device and the command center.

FIG. 14 includes a graphical user interface 1400 including live video feeds from the forensic field test device and the command center. Using the video and associated, an operator at the forensic field test device and the user at the command center may carry out video and audio communications, such as questions and answers, orders and responses.

Returning to FIG. 13, in some implementations, graphical user interface 1300 also includes an icon 1308. By selecting icon 1308, the user can access other information and control operation of the first field test device. Such other information and operation include: user log in, user registration, sample processing operation, system maintenance, turning the device on or off, etc.

Some implementations provide a method, the method including establishing a plurality of two-way communication links between a command center and at least two forensic field test devices. The command center includes a computer. The forensic field test devices include chemical, parametric, or diagnostic digital devices or systems that are located remotely from the command center. The method also involves presenting a plurality of indications of the at least two forensic field test devices in a user interface of the command center.

In some implementations, the method further includes presenting in the user interface data indicating status of one or more of the at least two forensic field test devices. In some implementations, the method also includes receiving at the command center data indicating operations of the forensic field test devices. In some implementations, the method also includes the command center storing data logs of the operational histories of one or more of the forensic field test devices. In some implementations, the method additionally includes presenting at the command center user interface one or more alerts requesting further action or specific attention from the user of the command center.

As shown in FIG. 9, in some implementations, the method involves providing at the command center user interface a plurality of applications related to general forensic topics or forensic service providers 902, and presenting at the user interface a plurality of user selectable indications of the plurality of applications. In some implementations, the method further includes providing, at the user interface, one or more user selectable indications connecting to one or more third-party applications or services 902. In some implementations, the method includes receiving a referral fee or other considerations from the one or more third-party applications or services.

In some implementations, the method further includes, at the command center, connecting to one or more secured forensic field test devices, wherein the secured forensic field test devices or configured such that every operational step of the secured forensic field test devices is time-date stamped and securely transmitted to the command center. In some implementations, data are transmitted from the test devices to the command center via a secure transfer protocol. For example, the data transmission may employ a security certificate or bank-transaction-like security mechanisms. In some implementations, the method also includes securely storing, at the command center, every operational step of the secured forensic field test devices, so that step-by-step operation of the secured forensic field test devices are stored and can be retrieved for purposes of processing operation of the secured forensic field test devices or for validating evidence collection.

In some implementations, the user interface of the command center includes one or more of the following: a graphical display, a one or two-way video interface, a one or two-way audio interface, an interface allowing a forensic command center user to control one or more aspects of a forensic field test device, an interface allowing a forensic command center user to activate one or more indications at a forensic field test device, a voice recognition audio control interface, and a touchscreen or pointing interface.

In some implementations, the command center user interface is configured to exchange data with a forensic field test device user interface. The forensic field test device user interface includes one or more of: a one or two-way video interface, a one or two-way audio interface, an interface allowing the command center user to control one or more aspects of the forensic field test device, and an interface allowing the command center user to activate one or more indications at the forensic field test device.

In some implementations, the command center program classifies users of the command center based on criteria such as level of authority or job. For example, a person with authority to review activity of various field test devices may be able to access run history, STR profiles, links to law enforcement magazines, links to non-STR forensic analysis sites and links to other service or product providers of interest. In contrast, a person with authority in procurement may get access to reagent/consumable levels in units; links to product supply companies, and advertisements to supply chain magazines. The command center program may identify a user by such classification by displaying different icons or other information when representing the user on a display screen.

Some implementations provide a system for processing biochemical or biometric data that includes one or more bidirectional communication systems connected to one or more motor vehicles, airplanes, or drones, and one or more remote quality review station.

In some implementations, the system includes components for communicating test results to test subjects.

In some implementations, the system includes components for conducting financial transactions with test subjects.

Figure 16A:
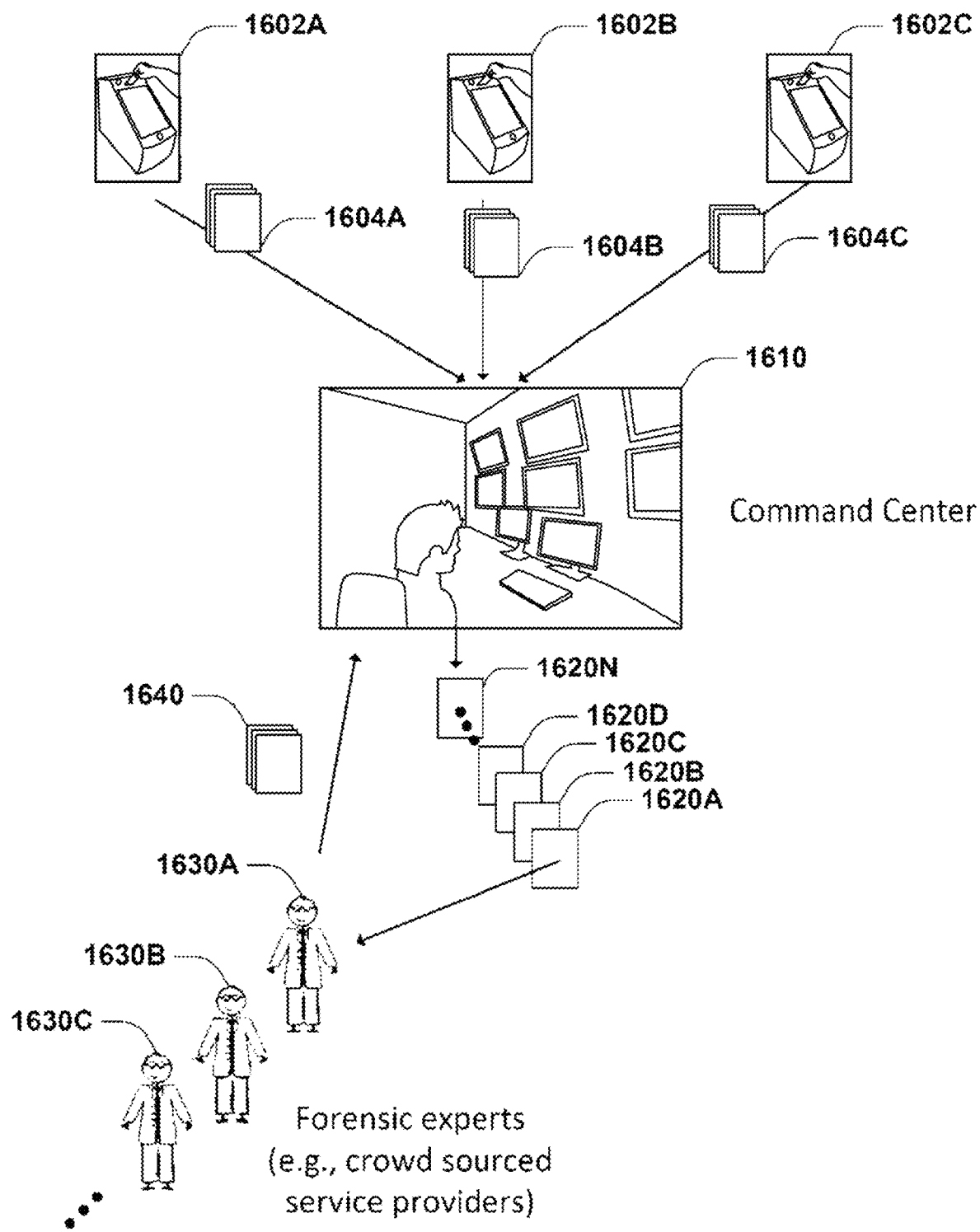
FIG. 16A illustrates system for processing biochemical or biometric data using crowd sourced service providers.

FIG. 16A illustrates system 1600 for processing biochemical or biometric data, such as electropherogram data. System 1600 can be used to implement methods illustrated in FIGS. 16B-16F further described hereinafter. System 1600 is similar to the system illustrated in FIG. 1, but its illustration here emphasizes an embodiment of forensic expert crowd sourcing.

As explained above, the system may employ crowd sourcing to process biochemical or biometric files such as electropherograms.

System 1600 includes a plurality of forensic field test devices 1602A, 1602B, and 1602C. In some implementations, the forensic field test devices are configured to analyze DNA samples as described above. The forensic field test devices are located at a plurality of sites remote from a command center (1610).

The forensic field test devices 1602A, 1602B, and 1602C send biochemical or biometric data files 1604A, 1604B, and 1604C respectively to command center 1610. In some implementations, the data files include electropherogram data and/or other genetic profiles. In some implementations, the command center includes hardware and software as described above.

The command center is also referred to as a central communications hub. In some implementations, the central communications hub comprises one or more processors and at least one network communications interface configured for two-way communications with the forensic field test devices. The command center also includes a user interface that allows personnel at the command center to control various functions of the command center and functions of the forensic field test devices as described herein. The command center and the forensic field test devices provide a networked system for genetic tests having distributed test devices and centralized control capabilities.

In some implementations, a command center has the ability to receive information and queries from, and send information, queries and instructions to, remote devices through a communications network.

In some implementations, command center 1610 can establish two way communications with forensic field test devices 1602A, 1602B, and 1602C. In some implementations, forensic field test devices 1602A, 1602B, and 1602C can process samples to produce electropherograms, and then provide the electropherograms in files 1604A, 1604B, and 1604C to command center 1610. In other implementations, the forensic field test devices provide raw electrophoresis data in 1604A, 1604B, and 1604C to the command center, and the command center then processes the data to obtain electropherograms and/or genetic profiles.

In some implementations, one or more of the forensic experts are selected to review one or more of the electropherograms 1620A-1620N. In some implementations, the one or more forensic experts are selected based on characteristics of the forensic experts. For instance, the forensic experts may be rated by a quality score, and one or more experts having a score meeting a standard are selected. In some implementations, command center 1610 notifies the forensic experts 1630A, 1630B, and 1630C of a task to review one or more of the electropherograms 1620A-1620N.

In some implementations, the forensic experts can indicate their willingness to perform the review. In some implementations, forensic experts are selected to perform the review based on the time when they indicate they are willing to perform the review. For instance, the expert(s) first indicating their willingness to review the files are selected.

In some implementations, electropherograms 1620A-1620N are selected from among electropherograms generated from data 1604A, 1604B, and 1604C. In some implementations, the selected electropherograms have potential problems that need reviewing by an expert. For instance, the selected electropherograms 1620A-1620N can be flagged to have potential problems by a process illustrated in FIG. 16D.

Command center 1610 then provides one or more of the obtained electropherograms (1620A-1620N) to forensic experts such as crowd sourced service providers (1630A, 1630B, and 1630C).

In some implementations, the selected forensic experts are allowed to review the electropherograms 1620A-1620N in an order according to one or more characteristics of the electropherograms. For example, in some implementations, the forensic experts are allowed to review electropherograms 1620A-1620N according to a chronological order in which the electropherograms are obtained by command center 1610. In some implementations, the electropherograms 1620A-1620N are allowed to be reviewed in a chronological order in which the electropherograms are generated at the command center or at the forensic field test devices (16028, 1602B, and 1602C). In another implementation, the electropherograms 1620A-1620N are ranked or sorted according to one or more characteristics of the electropherograms, and they are queued and allowed to be reviewed in the ranked or sorted order—1620A, 1620B, 1620C, 1620D . . . 1620N. For instance, electropherogram 1620A is ranked highest in terms of its the complexity of the problems identified for the electropherogram or a priority or urgency level associated with the electropherogram. Electropherogram 1620A is thus allowed to be reviewed first before other electropherograms in the queue.

Figure 16B:
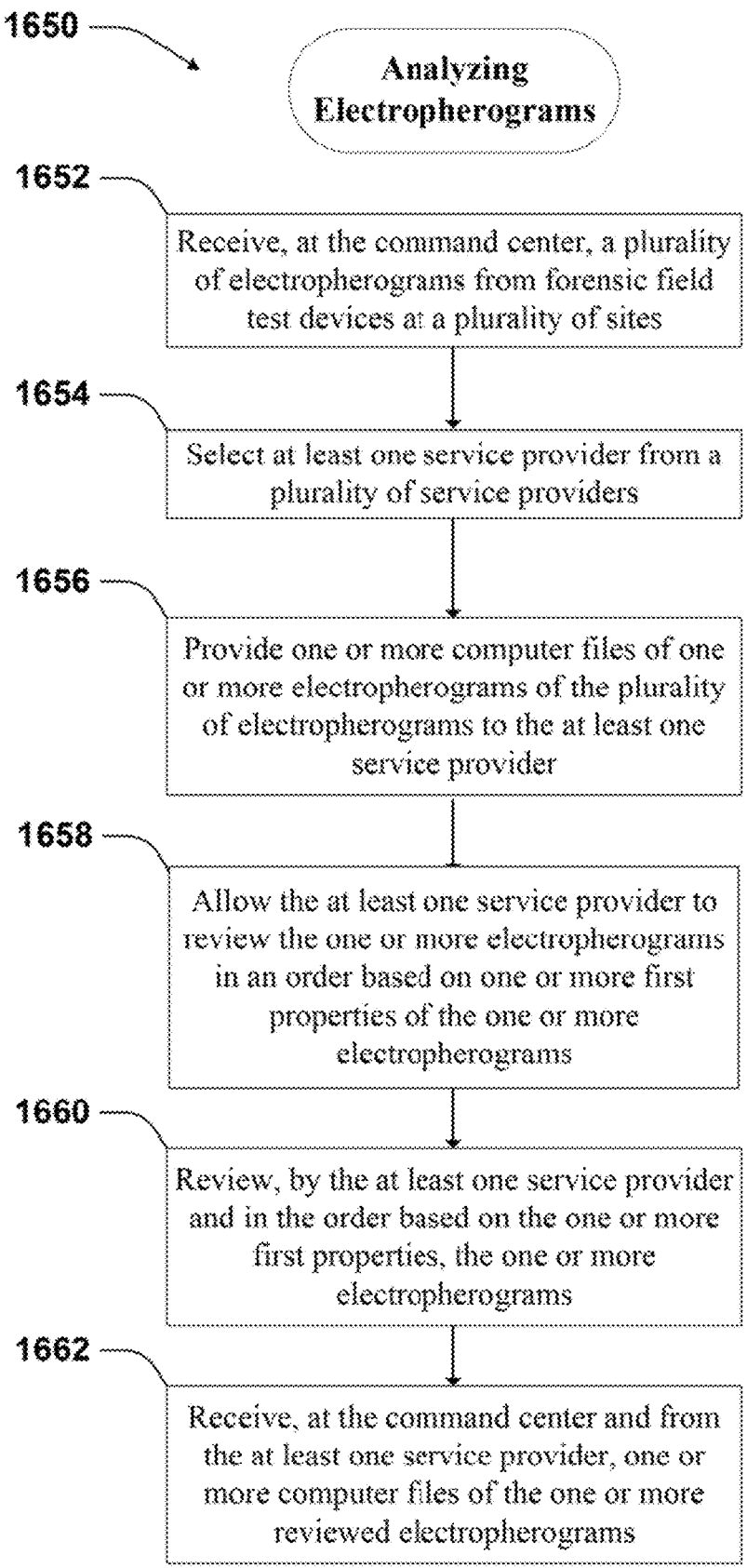
FIG. 16B illustrates a method for processing electropherograms using crowd sourced service providers.
Figure 16C:
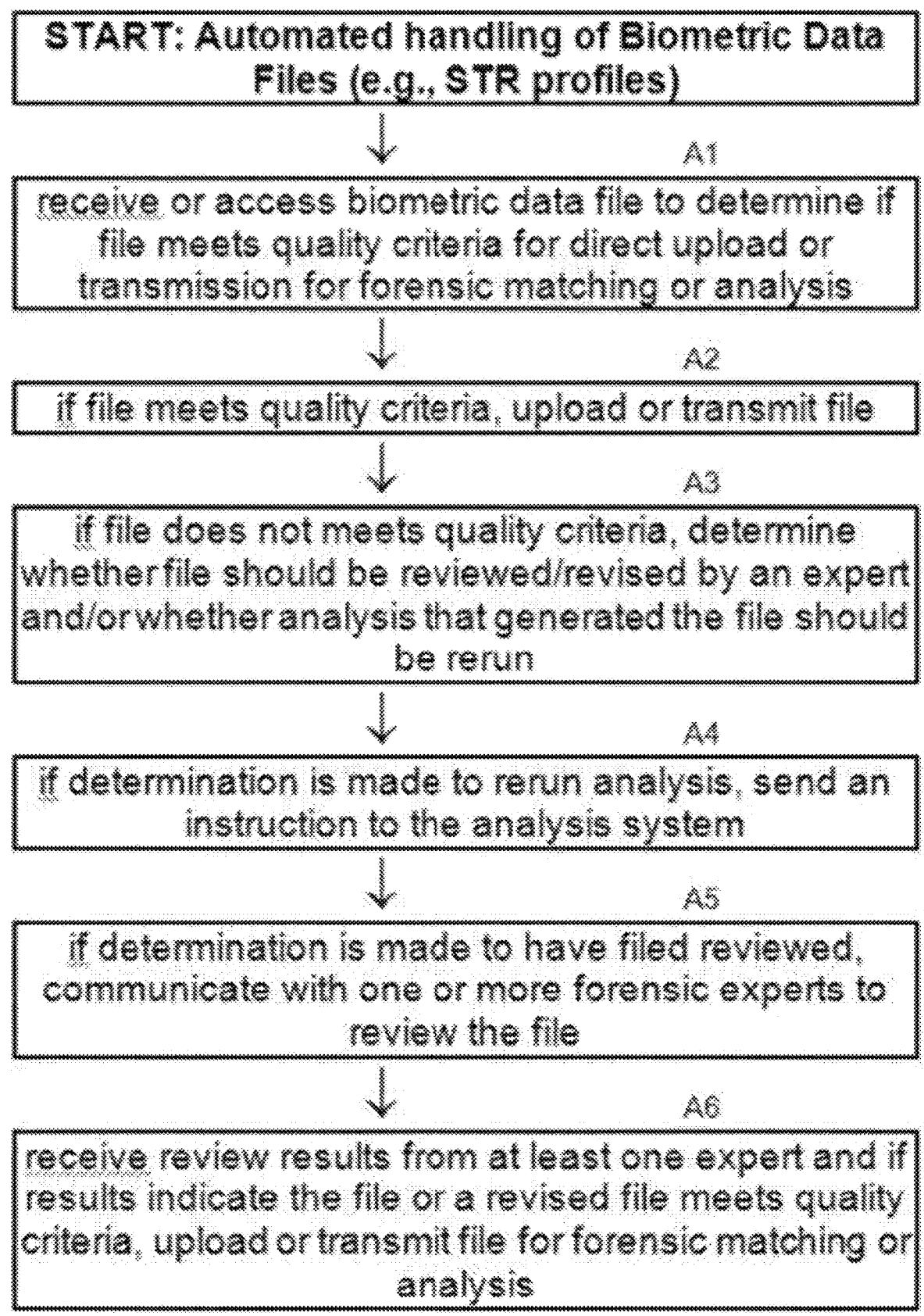
FIG. 16C illustrates a method for handling of a biometric data file by an automated system.
Figure 16D:
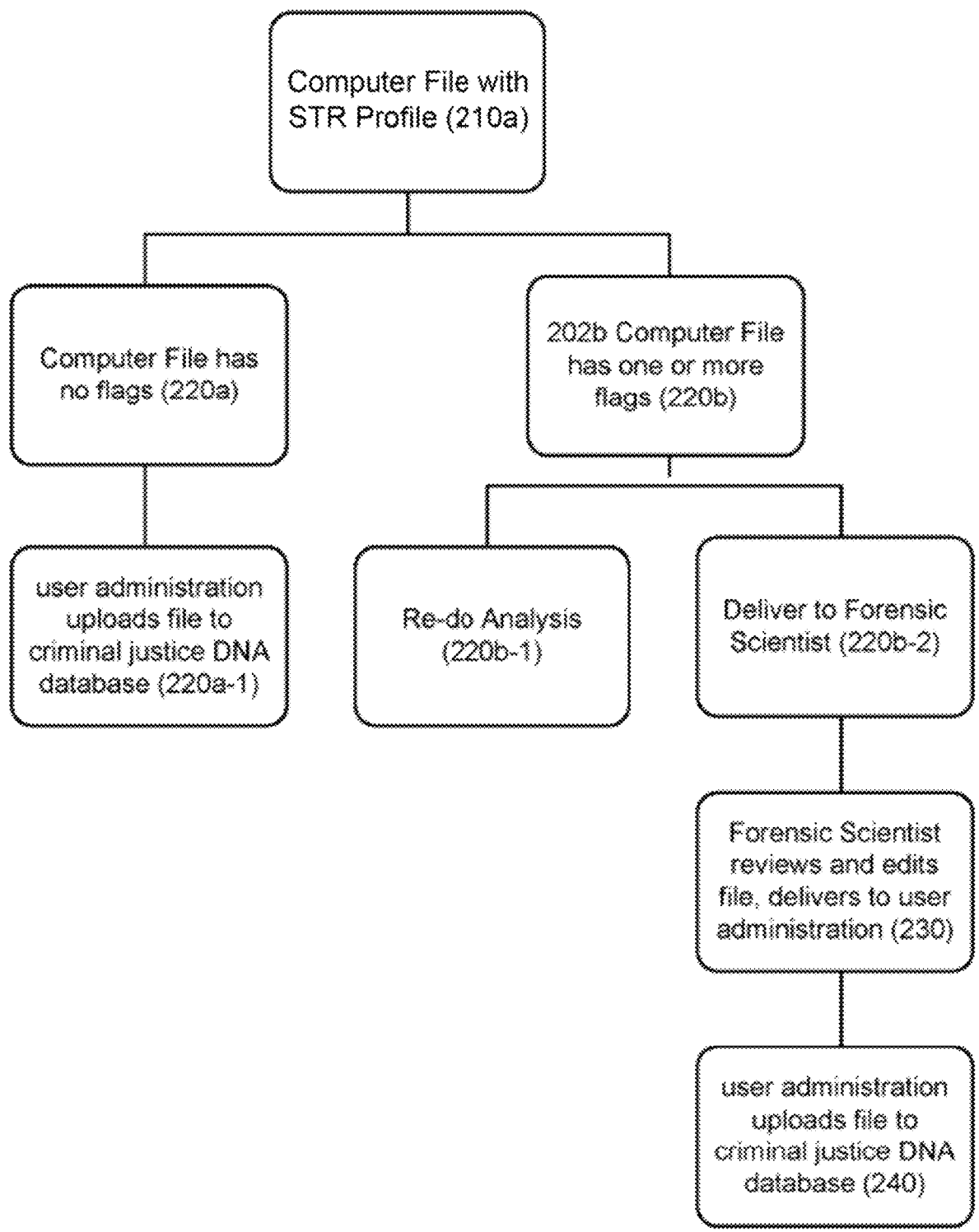
FIG. 16D illustrates a process for flagging and processing electropherograms.
Figure 16E:
FIG. 16E illustrates a process for reviewing an STR profile file or other forensic data file having flagged items.

In some implementations, the forensic experts may revise or edit the electropherograms to generate reviewed electropherograms 1640 by the operations described in FIG. 16E, operation B2.

After the selected forensic expert(s) review or revise the electropherograms in the designated order, they can send the reviewed electropherograms 1640 back to the command center. In some implementations, if an electropherogram among the reviewed electropherogram files 1640 meets a quality criterion, the electropherogram is uploaded or transmitted for forensic matching or analysis, such as using a third party database 112 illustrated in FIG. 1, or by applying step A6 in FIG. 16C.

FIG. 16B illustrates a method 1650 for processing electropherograms 1650. Method 1650 can be implemented using, e.g., system 1600 of FIG. 16A. The method can be used to process electropherogram data provided by forensic field test devices configured to analyze DNA samples at a plurality of sites that are geographically remote from a command center. Process 1650 starts by receiving a plurality of electropherograms or electrophoresis data from the forensic field test devices at the command center. See block 1652. If the command center receives electrophoresis data, the command center processes such data to produce electropherograms.

Process 1650 further involves selecting at least one service provider from a plurality of service providers such as forensic experts. See block 1654. In some implementations, as illustrated in operation C4 in FIG. 16F, one or more service providers are selected based on selection criteria such as the first service provider to respond, the first service provider to respond having a quality rating meeting a criterion, or lowering the criterion if no qualifying experts respond within a certain time. In some implementations, at least one service provider is selected based on one or more properties of the plurality of service providers. In some implementations, the one or more properties of the plurality of service providers include a time when the service provider indicates he or she is available to review the one or more electropherograms. In some implementations, as mentioned above, one or more service providers that respond first are selected. In some implementations, the one or more properties of the plurality of service providers include a quality rank of the service provider. In some implementations, the quality rank is based on accuracy of review, speed of review, level of training or expertise, and/or physical location of the service providers.

Process 1650 proceeds by providing one or more computer files of one or more electropherograms of the plurality of electropherograms to the at least one service provider. See block 1656. The one or more electropherograms are determined as needing review, such as electropherograms that are flagged and delivered to forensic experts as illustrated in FIG. 16D, operations 220b and 220b-2. See also operation A5 in FIG. 16C, and operation 450 in FIG. 16F.

Process 1650 further involves allowing the at least one service provider to review the one or more electropherograms in an order based on one or more first properties of the one or more electropherograms. See block 1658.

In some implementations, the one or more electropherograms are placed in a queue according to the one or more first properties of the electropherograms. The selected forensic experts or service providers are allowed to review the electropherograms in the queue in an order corresponding to the electropherograms' places in the queue. In some implementations, the one or more properties of the one or more electropherograms include complexity of an analysis of the electropherograms. In some implementations, the complexity is based on a number of allele calls that are flagged as potentially problematic. In some implementations, the one or more properties of the one or more electropherograms include a characteristic of a flagged problem in the electropherogram. For instance, the flagged problem may relate to noise in the electropherogram that confounds a signal peak related to an allele or STR. The characteristic may be the noise level, noise distribution, peak signal level, signal to noise ratio, or temporal separation of the peak and the noise. In some implementations, the one or more properties of the one or more electropherograms include a time when the electropherograms are generated. In such implementations, the electropherograms that are first generated are allowed to be reviewed first. In some implementations, the one or more first properties of the one or more electropherograms include a time when the electropherograms are received. In these implementations, electropherograms that are first received are allowed to be reviewed first. In some implementations, two or more of the properties are combined to determine the order of the electropherograms in the queue. For example, the electropherogram that is associated with an urgent label and generated in a specific time (e.g., more than 24 hours ago) is placed in the queue in before other electropherograms in the queue that do not meet both criteria.

Operation 1658 of process 1600 allows the at least one service provider to review the one or more electropherograms in the order based on the one or more properties of the one or more electropherograms. To enable this, in some implementations, a single service provider is selected from the plurality of service providers in operation 1654, and then a single computer file of the electropherogram that is at the front of the queue of the electropherograms is provided to the selected service provider. The process then repeats selection of a service provider and provision of a next electropherogram in the queue.

In some implementations, operation 1658 is optional, such that the plurality of the one or more electropherograms can be reviewed in any order, but the forensic experts are chosen to perform the review according to one or more properties of the service providers as described above.

In an alternative implementation, operation 1654 and 1656 are optional, such that any of the service provider in the plurality of service providers may review the one or more electropherograms in the order based on the one or more first properties of the electropherograms, namely according to the electropherograms places in the queue.

Process 1650 further involves reviewing the one or more electropherograms by the at least one service provider and in the order based on the one or more properties of the electropherograms. See block 1660. In some implementations, the service providers review the electropherograms by performing one or more operations listed in block 320 of FIG. 16E. The service provider may confirm the file meeting a quality criterion, or for at least one flagged peak in the electropherogram, the service provider may confirm a call, change or assign a call, delete a call, etc.

Finally, process 1650 involves receiving one or more computer files of the one or more reviewed electropherograms at the command center from the at least one service provider. See block 1662. See also block A6 of FIG. 16C and block 460 of FIG. 16F.

FIG. 16C illustrates a method for handling of a biometric data file by an automated system. These steps, as with those described in the context of FIG. 16B, can be performed by executable logic incorporated into a system that also performs one or more steps to collect the biometric data or can be performed by a separate logic system that receives biometric data files from an analysis system.

The example method generally begins when a results biometric data file is available. (Step A1) The automated system reads the data file to determine if the file meets quality criteria for submission to the next forensic system, such as a DNA matching system and if the file meets the criteria, the automated system takes steps to initiate the process (Step A2). In the case of DNA matching, these steps can include uploading, emailing, or otherwise transmitting the file to whatever system will provide the final 10 forensic report.

If the file does not meet quality standards, the automated system takes further steps to facilitate rapid forensic processing of the file. Quality standards can be variously configured by an operator or administrator of the automated system and can include various quality scores and/or specific data characteristics such as a number of times an allele call in an STR profile file is flagged. Further handling of the file can also be variously configured by an operator or administrator of the automated system and can include various criteria for taking one or more further handling actions. Thus, based on the criteria, the automated system makes a decision regarding the file (Step A3).

One determination that the automated system according to specific embodiments may make is to rerun the file. (Step A4). Various criteria configured at the system will aid in determining whether it is desirable to rerun the file and can include criteria such as: (1) the particular quality characteristics of the file, (e.g., some files may have so many flags that it is not desirable to have that file reviewed by an outside expert, or other quality characteristics may indicate that the analysis was sub-optimal); (2) the availability of the processing system to reprocess the sample and the expected speed of receiving reprocessing results; (3) the availability of service providers and the expected speed of receiving a corrected file; and (4) other criteria.

Another determination that the automated system according to specific embodiments may make is to request expert review of the file by communicating with one or more service providers. (Step A5). Various criteria configured at the system will aid in determining whether it is desirable to request an external review and how to request the external review can include criteria such as: (1) identities and contact information of one or more service providers stored at the system; (2) performance statistics or scores of one or more service providers stored at the system; (3) other criteria, such as cost, of one or more service providers stored at the system.

Once the decision is made to request expert review of the file, the automated system communicates to one or more experts to have the file reviewed. As discussed elsewhere herein, in specific embodiments, this communication can be multi-step and send out multiple requests that service providers respond to review the file, where the response can include cost and respond time proposals. The automated system can receive the responses and select a reviewer. After expert review is completed, if the resulting file meets criteria, it is uploaded. (Step A6). As discussed further below, a file may be confirmed by an outside expert or the file or part of the file may be corrected by the expert.

An automated system may have two STR profile files that require matching, that is, a determination that the profiles are consistent with having been generated from genetic material from the same person. In some jurisdictions, profiles constitute a match when at least 8 STR alleles are the same. This process is referred to herein as "profile matching". In one embodiment of the disclosure, the automated system communicates with one or more experts for profile matching of the data files. Profiles delivered to the service provider can include electropherograms that do or do not include flags, and can include files in which none, one or both files have previously been reviewed by an expert reviewer. Accordingly, in addition to determining whether the profiles constitute a match, the expert reviewer also can review the files to analyze or re-analyze flagged items, and produce a reviewed or revised file. The service provider delivers to the user a report determining a match or mismatch between the files and, optionally, reviewed and/or revised profiles.

As will be understood in the art of logic systems, various specific actions can be used to implement the general functions described herein. For example, "sending a file" as discussed herein may involve actual transmission of a file via email or download or alternatively can involve sending a link or notification allow an expert to view a file on a local device that remains stored at the original site. Likewise, sending a confirmed or correct file may comprise transmitting a file or may comprise transmitting data indicating that a file is confirmed or transmitting data indicating corrections needed to a file. Furthermore, uploading a corrected file may be completed by the automated system after receiving the file or correction or confirmation data or in some implementations, the automated system can provide an active link or other directions that would allow an service provider to upload the file. Furthermore, a "file" includes one or more files.

Furthermore, an automated system implementing (Step A5) and (Step A6) above can perform numerous steps, as described in more detail below, to crowd source one or more forensic review requests to one or more forensic service providers.

Furthermore, while an automated system may be designed to perform one or more steps without local human interaction, this does not preclude systems that include a user interface allowing a user to confirm, modify, or cancel automated steps or otherwise to monitor or affect the automated process.

Referring to FIG. 16D, in a more specific example, once a system has generated an STR profile file (210*a*), one or more further actions are taken with the file. As described herein, these further actions can be entirely automated, using one or more software components to decide on an action, or alternatively, one or more actions can include options for human intervention or human confirmation. In either case, further actions may be based on whether the file contains no flags (220*a*) or has one or more flags (220*b*). If the file has no flags, the system can upload the file to DNA database for searching (220*a*-1). If the file contains one or more flags, the system can decide between two options. One option (220*b*-1), involves requesting the analysis to be performed again. This can involve, for example, the system taking another sample from a subject and analyzing it with the system, or sending a sample to another facility for analysis. Another option (220*b*-2), involves delivering the file to a service provider for review. After the service provider has completed review and revision to the STR file, the revised file may be uploaded to a DNA database for matching (240). This upload may be done by the service provider or the revised file may first be delivered to the automated system (230), and the automated system may then upload the file to a DNA database for matching (240).

Referring to FIG. 16E, a protocol for having an STR profile file or other forensic data file reviewed can include the following steps: The system delivers computer file bearing flagged item to service provider (310). A service provider in receipt of a computer file containing flags performs a review. Objects of the review include clearing flagged items and/or confirming the file meets a quality control standard. According to specific embodiments, reviewing a computer file containing a flagged peak, the service provider may do any of the following: (i) Confirm the call of the flagged peak made by the software; (ii) Change or assign a call to a flagged peek, (iii) Delete a call made by the software, or (iv) Do nothing (320). Service provider delivers reviewed file to automated system (330) and the automated system uploads reviewed file to a criminal justice DNA database (340).

As described above, a review of a forensic file may be handled by an integrated automated system that performs some or all of the functions of communicating with various service providers, receiving bids or job acceptance requests, and assigns jobs to service provides and receives results. Alternatively or additionally, a review request may be communicated to a crowd-source server as described below that handles some or all communications with service providers.

In either alternative, service providers typically will contract with the system operator to provide the service "on-demand" for certain compensation. Other arrangements to form a contract to perform services may be used, such as one-sided contracting, in which the job is broadcast for performance by anyone. Individuals who contract with the service operator are referred to herein as "service providers". Service providers can be pre-qualified to perform the file review. For example, a service provider may be required to have the requisite skills to perform a review of a forensic file or to have passed a licensing examination. Such a person may already possess such skills, or may be trained, e.g., by the person or entity, to gain such skills.

Service providers can be assigned a quality rank based on desired factors such as accuracy of review, speed of review or physical location. In certain jurisdictions, an STR profile computer file, if it is to be reviewed, must be reviewed by a person physically located in a certain jurisdiction, such as a U.S. state.

Service providers can be compensated for performing a job in any number of ways. These include, for example, a fixed fee per file reviewed, a sliding fee based on difficulty of the file, e.g., number of flags in a file, or speed of turn-around. Such terms may be agreed upon in advance of accepting a particular job. Compensation may be made after each instance of performing a job, or at periodic time periods, such as semi-monthly. Compensation can be arranged electronically, for example by direct deposit to a bank account, or by physical check.

All computational methods described herein may be performed by a computing device, which implements the methods programmatically, that is, through the use of code or computer-executable instructions, e.g., software, executable by one or more processors. These instructions may be carried on a non-transient computer-readable medium.

The system can include processors and computer-readable media including which, when executed, carry out steps of the methods of this disclosure.

In operation, the method can involve some or all of the following steps: receiving notification from a user of a job to be performed, e.g., review of an STR profile computer file, notifying service providers of a job to be performed; receiving an indication from one or more service providers of their willingness to perform the job; selecting a service provider who has indicated their willingness to perform the review; providing access to the computer file to the selected service provider; having the service provider review the file; and receiving from the service provider a reviewed file.

The user can provide the computer file before or after a service provider has been selected to perform the job. The user also can specify qualities desired or necessary in the service provider, such as level of training or expertise, physical location, turn-around time, error rate, etc. The request can be made directly from an expert system that generates the profile and that accesses the communications network directly, or by a person who submits the job.

Service providers agree to receive notifications from the service operator that an STR profile file is available for review. Service providers have the option to respond to a notification indicating their willingness to review the file. If selected to review the file, the selected service provider may review the file and annotate it, for example by addressing flagged items, and provide the reviewed file to the organization.

A service provider can receive an alert through any appropriate computing device. For example, the device can be a smart phone, a tablet, a laptop computer, a desktop computer or a television. These may be provided with network connectivity through cell service, wireless Internet, etc. Processing resources can enable service providers communicate with users or customers over a suitable communications network.

Figure 16F:
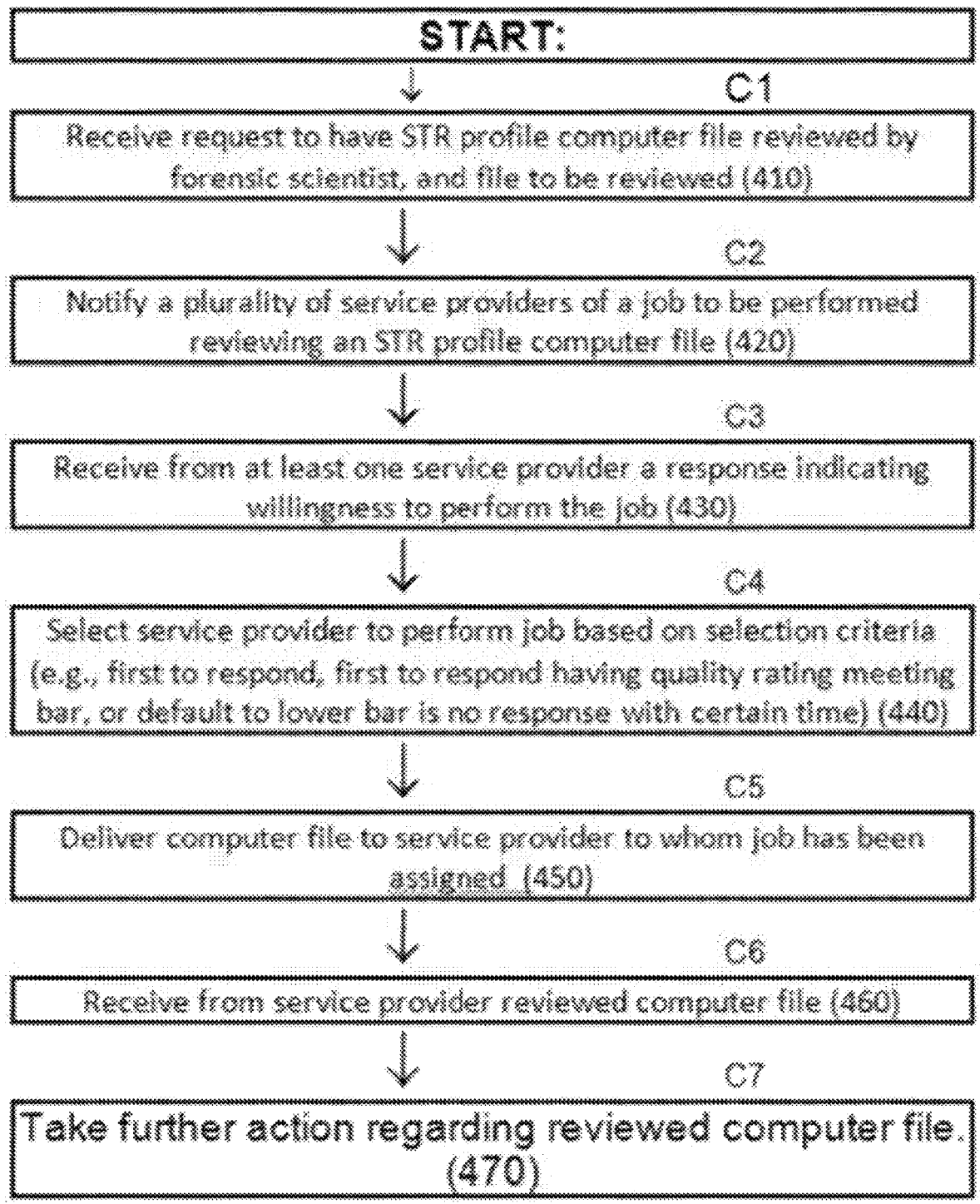
FIG. 16F illustrates a process for processing an STR profile computer files.

In one embodiment, crowd sourcing is used to select a service provider to review an STR profile file, either by an automated forensic system or via a crowd-sourcing server. Referring to FIG. 16F, over a communications network, a request is received to have a job done, e.g., review of a forensic report computer file (410). A plurality of service providers are notified of job to be performed (420).

Any suitable communications network can be used, such as cell or Internet. The notification may be in the form of a phone call, a text message, a mobile device notification, etc. Notification can come through an application designed for a mobile device or a computer. The notification can include a "response time," a time within which a person selected to perform a job must complete the job. Such a time may be no more than any of 10 hours, 2 hours, 1 hour, 30 minutes, 10 minutes or 5 minutes.

Once notified, a service provider can indicate that they are willing to accept the job or reject the job (430). Or, they may simply ignore the notification. The indication can be made over a communications network that can be the same or different than the network that provided the notification. Individuals who indicate they are willing to accept the job are referred to as "bidders".

The system (whether an automated system or crowd sourcing server) can select one or more bidders to perform the job of reviewing the STR profile file (440). Selection can be made based on any number of criteria. In one embodiment, the first service provider to bid for the job is selected. In another embodiment, the first service provider having a specified qualification ranking may be selected, e.g., a certain turn-around time or accuracy score. An individual selected to perform a job is referred to as a "selected service provider". Once a bidder is selected as a selected service provider, the system delivers the computer file to be reviewed to the selected service provider (450). The computer file can be delivered in any number of ways. For example, an application can allow the selected service provider to click through to the file. The selected service provider may be able to enter a website location from which the file can be accessed. Alternatively, the file can be provided by email.

The selected service provider reviews the file, making any changes necessary. The reviewed file can be saved over the original file or as a new file. The selected service provider then delivers the reviewed file to the system (460). Delivery can be by any suitable route, including the route by which the file was delivered to the selected service provider.

Forensic field test devices and other devices for testing genetic profiles (also referred to genetic test devices) may experience errors or inaccuracies, such as system errors or inaccuracies due to malfunctioning of system components, improper calibration of environmental parameters, etc. Also, errors or inaccuracies may result from operator errors.

Some implementations provide a method and a system for automatically detecting conditions that require calibration of the forensic field test devices, or require retraining, recertification, and/or reauthorization of operators of the forensic field test devices. Some implementations provide a method for detecting system or operator errors. In some implementations, the method starts by obtaining a control sample comprising genetic material. The control sample is provided by an individual person or an individual organism that can provide a validation sample for the purpose of validating, at a later time, an operator of the genetic test device is following the proper operational procedure and the genetic test device is functioning properly. In some implementations, the individual person providing the validation sample can be a staff member or a human operator of the device. In various implementations for humans, the genetic material usually comprises DNA. For other organisms, the genetic material in the control sample may comprise RNA. In a different aspect, the genetic material can comprise a gene, a part of a gene, a group of genes, a DNA molecule, a fragment of DNA, a group of DNA molecules, or the entire genome.

The method further involves properly obtaining a control genetic profile using the control sample and the genetic test device. Namely, the genetic profile is obtained when the operator of the genetic test device is following a proper operational procedure and the device is functioning properly.

The method further involves storing the control genetic profile obtained from the control sample in a database. In some implementations, a plurality of control genetic profiles are obtained from a plurality of control individuals. The plurality of control genetic profiles are also stored in the database.

In some implementations, the genetic test device can provide a periodically reminder to initiate a validation procedure that validates an operator of the genetic test device is following the proper operational procedure and the genetic test device is functioning properly.

During a validation procedure, the method involves having a to-be-validated operator operate the genetic test device, which includes supplying a validation sample obtained from the same individual who provided the control sample.

The method further involves processing the validation sample using the genetic test device, thereby obtaining a validation genetic profile.

The method then compares the validation genetic profile to the control genetic profile stored in the database, both profiles having been obtained from the same individual. Based on the comparison, the method determines whether there is a match between the validation genetic profile and control genetic profiles stored in a database. If there is a match, the system validates that the genetic test device is functioning properly and the operator is operating the device properly. On the contrary, if no match is found, the system provides an indication that either the genetic test device is not functioning properly, and/or the operator is not operating the device properly. In some implementations, the system prompts a calibration or troubleshooting of the device. In some implementations, the system prompts to operator to undergo training/retraining to learn how to properly operate the device.

Some implementations provide methods and systems for obtaining a genetic profile from a DNA test sample. The DNA sample may be associated with a person of interest with a known identity (e.g., a sample obtained from a suspect at a booking station) or an unknown identity (sample left at a crime scene). The methods and systems can be automated and standardized. However, these systems and methods are not always completely error proof. Under some circumstances, a genetic test sample can be inadvertently contaminated by genetic material from various sources, such as DNA of a staff member who handles the sample or operates the test device, or DNA of another individual inadvertently coming into contact with the test sample.

In some implementations, the systems and methods provided herein can detect that a DNA sample has been contaminated with DNA materials of other individuals at a testing facility, e.g., staff members at a police station, a booking station, a detention center, a jail, etc. In some implementations, upon detection of the contamination, the methods and systems provide instructions to obtain a new test sample from the person of interest if the person is available. In some implementations, the methods and systems can correct errors that would otherwise result from the contamination and obtain an error-corrected genetic profile of the person of interest.

Figure 17A:
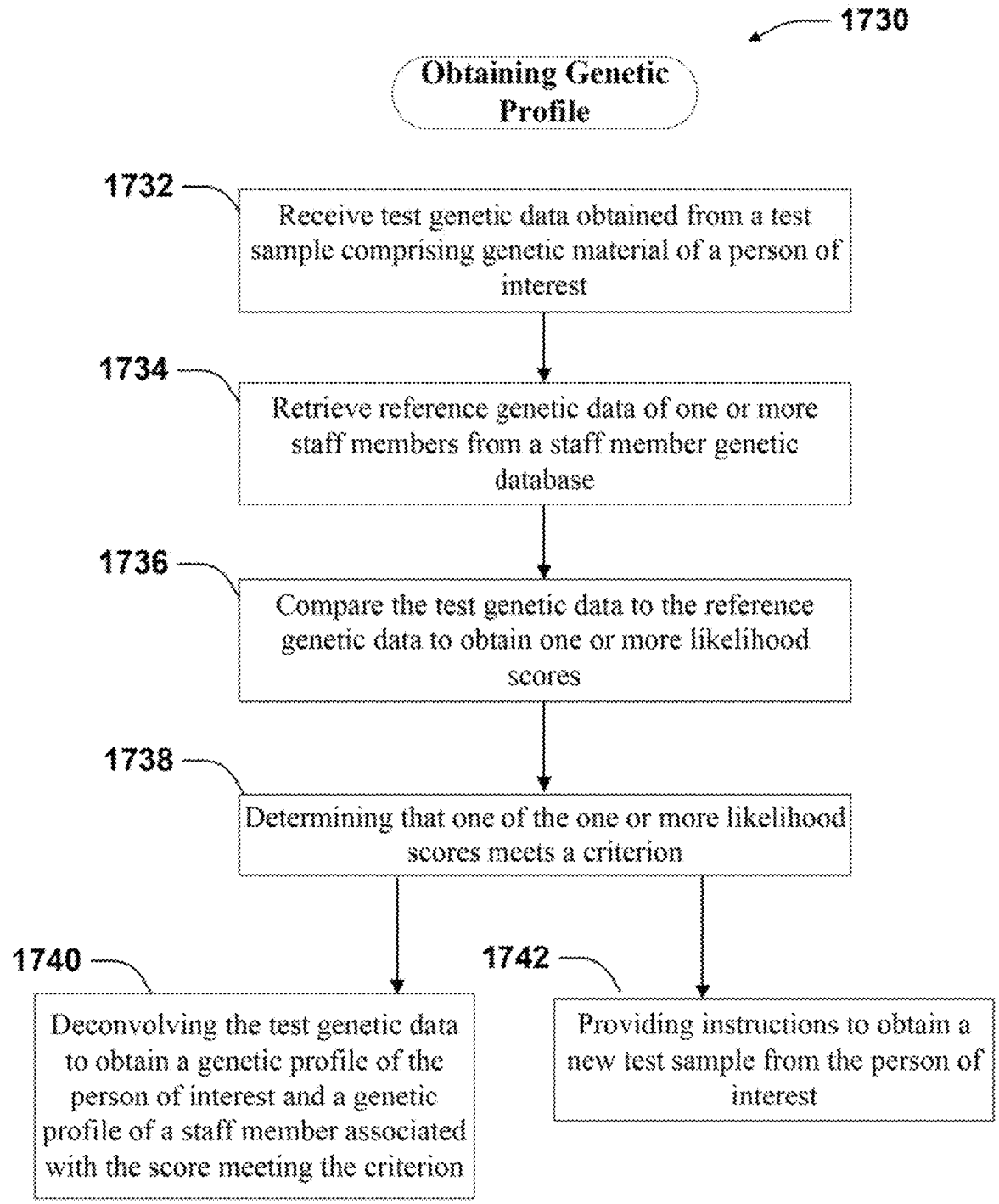
FIG. 17A shows a flowchart illustrating a process for obtaining a genetic profile from a test sample including genetic material of a person of interest.

FIG. 17A shows a flowchart illustrating a process 1730 for obtaining a genetic profile from a test sample including genetic material of a person of interest. Process 1730 involves receiving test genetic data obtained from the test sample comprising genetic material of the person of interest. See block 1732. Genetic data as used herein refers to data obtained from genetic material of a subject or a person. In some implementations, genetic material includes DNA, RNA, cDNA, RNA, mRNA, ribosomal RNA, mitochondrial DNA, and other nucleic acid molecules. In some implementations, the genetic material can comprise a gene, a part of a gene, a group of genes, a DNA molecule, a fragment of DNA, a group of DNA molecules, or the entire genome. The genetic data may be obtained from the genetic material after using various techniques and procedures. In some implementations, the genetic material is subject to amplification, hybridization, extension, and other biochemical reactions, and the reaction products are assayed to provide the genetic data. In some implementations, the genetic data comprise electrophoresis data obtained through electrophoresis reactions. In other implementations, the genetic data comprise sequencing data obtained using sequencing reactions and techniques such as next generation sequencing. In some implementations, electrophoresis data include electropherograms, features thereof, and/or data derived the electropherograms. In some implementations, the genetic data include data regarding various alleles of interest that may be used to uniquely identify individuals. In some implementations, the genetic data include short tandem repeat (STR) data. In some implementations, the genetic data include single nucleotide polymorphism (SNP) data.

The identity of the person of interest may be known or unknown, and the person may be available or unavailable. For example, the person of interest can be unknown and unavailable when the presence biological sample is collected at a crime scene. In another example, the person of interest is known, such as an arrestee, a detainee, or a suspect. In some implementations, the method is implemented on a computer comprising one or more processors and system memory.

In some implementations, the test genetic data includes short tandem repeat (STR) data or SNP data. In some implementations, the SDR data are obtained by performing one or more electrophoresis reactions using the test sample. In some implementations, the genetic profile includes information of SDR alleles at multiple loci.

Process 1730 further involves retrieving reference genetic data of one or more staff members from a staff member genetic database. In some applications, for example, the staff members are staff at a genetic testing facility or members of a law enforcement organization. See block 1734.

Process 1730 further involves comparing the test genetic data to the reference genetic data to obtain one or more likelihood scores. See block 1736. Each of the likelihood scores indicates how likely or probable the test sample includes genetic material of one of the one or more staff members in the staff member genetic database. In some implementations, the likelihood score is calculated based on a likelihood as described herein after. In some implementations, the likelihood score is based on a probability obtained in accordance with the Bayesian theory. In some implementations, the likelihood score is a quantity that correlates with the probability that the test sample includes genetic material of one of the one or more staff members. In some implementations, the comparison of the test genetic data to the reference genetic data can be implemented by a process illustrated in FIG. 17B.

In some implementations, the one or more staff members include staff members in the chain of custody of the test sample. In some implementations, the genetic data obtained from the test sample are compared to reference data of each staff member in the chain of custody of the test sample. A chain of custody refers to a chronological order, documentation, or paper trail, showing the seizure, custody, control, transfer, analysis, disposition, or other handling of the test sample.

In some implementations, the genetic profile includes information of STR alleles at multiple loci. In some implementations, the likelihood score is based on: (i) a number of alleles in loci that each contain at least one STR allele from a staff member's reference genetic data and at least one STR allele from the test genetic data (the loci are also referred to as common loci hereinafter); (ii) a number of alleles detected in both the staff member's reference genetic data and the test genetic data (the alleles are also referred to as match alleles hereinafter); and (iii) a number of alleles detected in the staff member's reference genetic data but not in the test genetic data (the alleles are also referred to as mismatch alleles hereinafter).

In some implementations, likelihood scores maybe obtained using software DNA matching tools such as STR-Mix™ or TrueAllele™.

In some implementations, alleles detected in both the staff members reference genetic data and the test genetic data are weighted differently. In some implementations, the likelihood score L is calculated according to the following formula:

$$L = \frac{\sum_{1}^{i}(w_i \times \beta_i) - \gamma}{\alpha}$$

wherein $\alpha$ is a total number of alleles in common loci, namely loci that each contain at least one STR allele from a staff member's reference genetic data and at least one STR allele from the test genetic data; $\beta_i$ is the $i^{th}$ ranked allele among match alleles, namely the alleles detected in both the staff member's reference genetic data and the test genetic data, wherein the alleles are ranked by a quantity measurement of the alleles, such an amplitude of a peak in an electropherogram or data correlating therewith; $w_i$ is a weight assigned to the $i^{th}$ ranked allele; and $\gamma$ is the number of mismatch alleles, namely alleles detected in the staff member's reference genetic data but not in the test genetic data.

In some implementations, the quantity measurement of the alleles is based on STR allele signal intensity in an electropherogram. In some implementations, the more highly ranked alleles are weighted more heavily. In some implementations, for example, the two highest ranked alleles are given a weight of 1, while other alleles are given a lower weight, e.g., 0.8. Other values of weights may be used depending on applications.

Figure 18C:

FIGS. 18A-18E show graphical user interfaces or a computer tool for comparing electrophoresis data of test samples and staff members. FIG. 18A shows multiple files for multiple test samples, each file of a sample in one row. FIG. 18B shows summary data of a test sample 215M's STR alleles compared to a number of staff members' STR alleles, with each row of the table showing data for a comparison between the test sample an a staff member. The first column from the left shows labeling IDs of the reference samples (e.g., obtained from staff members). The second column shows the numbers of common loci. The second column the third column from the left shows the numbers of match alleles. The fourth column from the left shows the numbers of mismatch alleles.

Figure 17B:
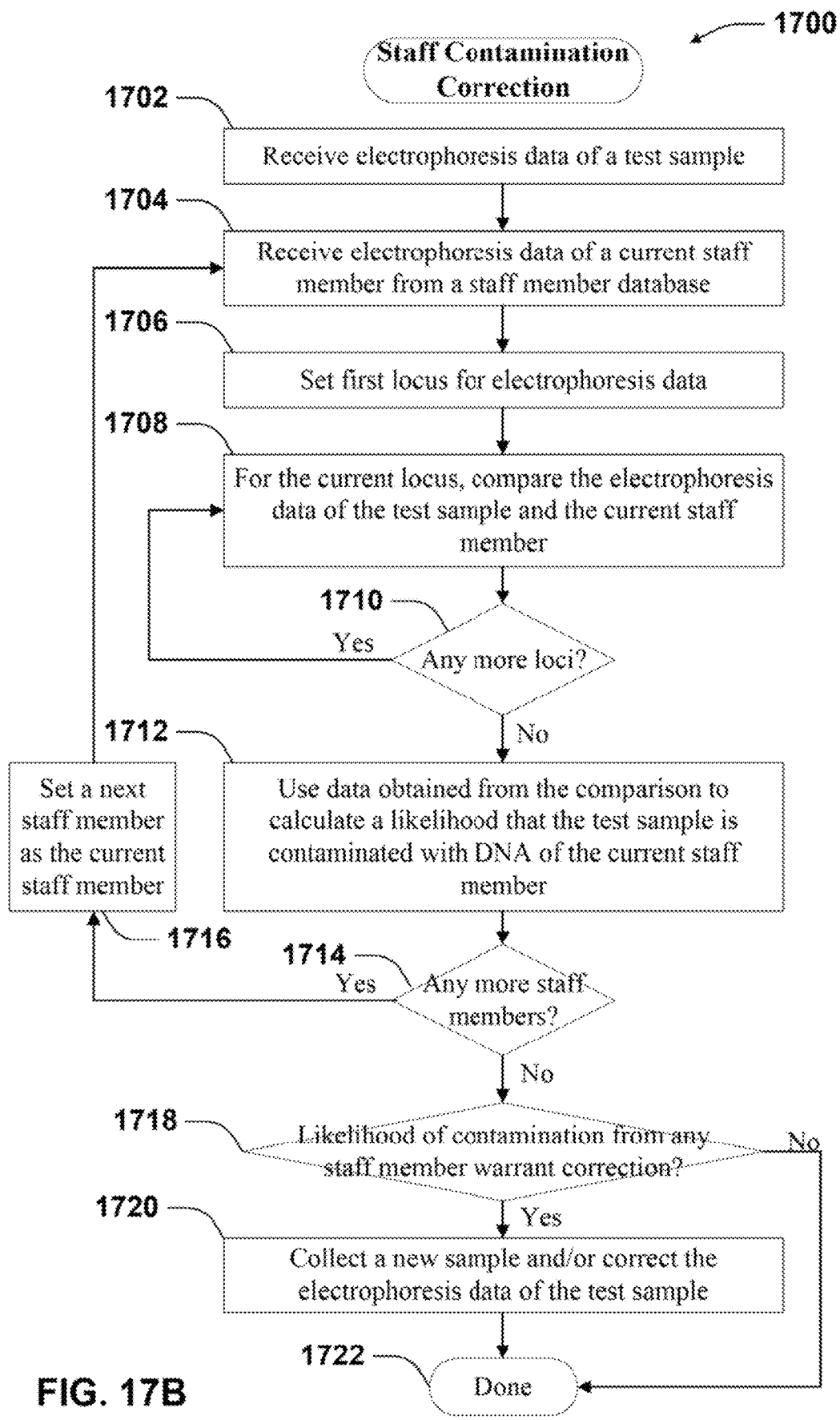
FIG. 17B shows a flowchart illustrating a process for correcting contamination of DNA sample by DNA material of staff member.
Figure 18D:
Figure 18E:

Each figure of FIGS. 18C-18E shows allele information for various loci for one of three reference samples (278M, SED0424, and SED0148) compared to test sample 215M. In these figures, the first column from the left contains the names of the different common loci. The second column from the left contains the names of the alleles at the common loci detected in the test sample, and the third column from the left contains the names of the alleles at the common loci detected in the reference sample. The alleles of the test sample data and reference sample data (staff data) can be compared using the methods described above to obtain the likelihood score L, or using process 1700 described in FIG. 17B below.

In some implementations, the likelihood score of block 1736 can be a direct match probability or a likelihood ratio score.

A direct match probability is calculated under the assumptions of Hardy-Weinberg equilibrium. For heterozygous loci, the frequency of the match in the population can be determined using the formula:

Frequency of $PQ = 2 \times p \times q = 2pq$ where p and q are the frequency of each allele in the population.

For homozygous loci, the frequency of the match in the population is determined using the formula p×p=p2 where p is the frequency of the allele in the population. A correction factor (CF) is often included in homozygous calculations to correct for the possibility of subpopulations. The correction factor formula is:

Correction Factor=$[p(1-p) \times \theta]$

Theta ($\theta$), an estimate of population subdivision, is often assumed to be 0.01.

Frequency of $PP = (p \times p) + $ correction factor $= p2 + [p(1-p) \times 0.01]$ The combined frequency of matching at multiple loci within a racial group is determined by the mathematical product of the frequency of each locus relevant to the match.

Direct match statistics can also be presented as a likelihood ratio. The numerator assumes that the DNA profile of the test sample matches the reference sample, and the denominator assumes the DNA profile of the test sample came from a randomly selected person.

Combined Frequency=Freq($FGA$)×Freq($TPOX$)× Freq($vWA$)× . . .

Likelihood Ratio=1/Combined Frequency

Table 1 provides hypothetical data as an example for calculating a likelihood ratio score.

TABLE 1 hypothetical data for calculating a likelihood ratio score

| Locus | Alleles | Allele 1 Frequency | Allele 2 Frequency | Formula | Locus Frequency |
|---|---|---|---|---|---|
| FGA | 21, 22 | 0.173 | 0.189 | 2 pq | 0.065 |
| TPOX | 8 | 9.544 | | p^2 + CF | 0.298 |
| D851179 | 13, 14 | 0.339 | 0.202 | 2 pq | 0.137 |
| vWA | 18 | 0.222 | | p^2 + CF | 0.051 |

Combined Frequency=0.065×0.298×0.137× 0.051=0.00014

Likelihood Ratio=1/0.00014=7143

The combined frequency can also be stated as:

Approximately 1 in 7143 individuals of the same ethnic group would be expected to match this profile.

The likelihood ratio is properly stated as:

The DNA profiles of the reference and test samples are 7143 times more likely to be found if the test sample came from the reference sample than if the test sample came from a randomly selected, unrelated person.

Returning to process 1730 of FIG. 17A, the process further involves determining that one of the one or more likelihood scores meets a criterion. See block 1738. In some implementations, the criterion may require a likelihood score to exceed or meet a threshold value. In some implementations, the criterion requires a score to be the largest likelihood score and meet the threshold value.

Based on determining that one of the likelihood scores meets a criterion, process 1730 provides, as one option, instructions to an operator of the test device to obtain a new test sample from the person of interest, which is feasible if the person is known and available. See block 1742. In some implementations, process 1730 involves deconvolving the test genetic data to obtain a genetic profile of the person of interest and a genetic profile of a staff member associated with the likelihood score meeting the criterion. The genetic profile of the person of interest obtained by deconvolving the test genetic data effectively remove the contaminating effect of the contaminating DNA, correcting errors due to the contamination, and improving the validity and accuracy of the genetic profile obtained for the person of interest.

Various techniques may be used to deconvolve the test genetic data to obtain two or more genetic profiles. In some implementations, the staff member's genetic data can be subtracted from the test genetic data. In another implementation, the staff member's genetic data can be used by DNA matching tools (e.g., STRMix™) to obtain the genetic profiles of the contributing individuals. However, this is not necessary in some implementations. For example, in some implementations, genetic profile deconvultion methods (e.g., TrueAllele™) can resolve DNA mixture to obtain two or more genetic profiles without prior knowledge of the genetic profiles of the contributors.

FIG. 17B shows a flowchart illustrating a process 1700 for correcting contamination of DNA sample by DNA material of staff member, thereby allowing a more accurate genetic profile to be obtained from the test sample. Process 1700 starts by receiving electrophoresis data of the test sample. See block 1702. The test sample includes genetic material of a person of interest.

Process 1700 further involves receiving electrophoresis data of the current staff member from a staff member database. See block 1704. The staff member database includes electrophoresis data of one or more staff members.

Process 1700 further involves setting a first locus for electrophoresis data. See block 1706. Process 1700 then compares the electrophoresis data of the test sample and the current staff member for the current locus. See block 1708. The electrophoresis data of the test sample and the current staff member can be similar to those illustrated in FIGS. 18C, 18D, and 18E.

Process 1700 then involves deciding whether there are any more loci to consider. See decision block 1710. If so, the process loops back to block 1708 to compare the electrophoresis data of the test sample and the current staff member for the next locus. See the yes branch of decision block 1710.

If no more loci need to be considered, process 1700 proceeds to use data obtained from the comparison to calculate a likelihood that the test sample is contaminated with DNA of the current staff member. See block 1712. In some implementations, the likelihood may be calculated as the likelihood score described above with reference to operation 1736 of process 1730 in FIG. 17A.

Process 1700 then determines whether there are any more staff members to consider. See block 1714. If so, the process sets the next staff member as the current staff member (block 1716) and loops back to block 1704 to receive electrophoresis data of the current staff member from the staff member database. If no more staff members need to be considered, process 1700 proceeds to decide whether a likelihood of contamination from any staff member warrants correction. See block 1718. In some implementations, this decision can be implemented using the same criterion as in block 1738 of process 1730 in FIG. 17A.

If the likelihood of contamination warrants correction, process 1700 proceeds to collect new sample and/or correct the electrophoresis data of the test sample. See block 1720. The correction may be performed by, e.g., deconvolving the electrophoresis data and/or removing the contribution of the contamination contaminating data as described above. The correction process then concludes at block 1722. If the likelihood of contamination does not warrant correction, process 1700 skips operation 1720 and concludes the correction process.

All publications and patent applications mentioned in this specification are herein incorporated by reference to the same extent as if each individual publication or patent application was specifically and individually indicated to be incorporated by reference.

While certain embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method implemented on a command center computer comprising at least one network communications interface, at least one display screen and user interface, and one or more processors, the method comprising:

establishing, through the at least one network communications interface, two-way communications between the command center computer and a plurality of sites remote from the command center computer, wherein each site comprises at least one forensic field test device configured to perform a biological analysis assay on DNA samples to identify individuals using DNA samples from the individuals;

displaying, using the at least one display screen and user interface of the command center computer, aspects of the forensic field test devices of the plurality of sites, wherein at least one of the aspects comprises a site identifier for each of the forensic field test devices and one or more additional aspects selected from the group consisting of: a current status of at least one of the forensic field test devices, a log of operations of at least one of the forensic field test devices, an instrument run list of at least one of the forensic field test devices, a level of consumables of at least one of the forensic field test devices, and operator information of at least one of the forensic field test devices;

receiving, using the display screen and user interface, input from personnel present in the command center for controlling operation of at least one of the forensic field test devices; and remotely controlling operation of the at least one forensic field test device based on the input.

2. The method of claim 1, wherein the displaying comprises displaying a geographical map showing the site identifiers for the plurality of sites comprising the forensic field test devices.

3. The method of claim 2, further comprising receiving user input, using the user interface, the user input comprising selecting one or more of the site identifiers displayed on the geographical map.

4. The method of claim 3, wherein the displaying comprises displaying a log of operations of a forensic field test device at a site associated with a selected site identifier.

5. The method of claim 1, wherein the remotely controlling operation comprises locking the operation of at least one of the forensic field test devices.

6. The method of claim 1, wherein remotely controlling the operation of the at least one forensic field test device comprises adjusting an operation parameter of the at least one forensic field test device.

* * * * *

UNITED STATES PATENT AND TRADEMARK OFFICE
CERTIFICATE OF CORRECTION

PATENT NO. : 12,200,042 B2
APPLICATION NO. : 17/039647
DATED : January 14, 2025
INVENTOR(S) : Robert A. Schueren et al.

Page 1 of 1

It is certified that error appears in the above-identified patent and that said Letters Patent is hereby corrected as shown below:

On the Title Page

Below item (72), insert -- (73) Assignee: IntegenX Inc., Pleasanton, CA (US) --.

Signed and Sealed this
Twenty-ninth Day of April, 2025

Coke Morgan Stewart
*Acting Director of the United States Patent and Trademark Office*